(12) United States Patent
Nakaki et al.

(10) Patent No.: US 10,023,838 B2
(45) Date of Patent: Jul. 17, 2018

(54) METHOD OF INDUCING DIFFERENTIATION FROM PLURIPOTENT STEM CELLS TO GERM CELLS

(71) Applicant: KYOTO UNIVERSITY, Kyoto-shi, Kyoto (JP)

(72) Inventors: Fumio Nakaki, Kyoto (JP); Mitinori Saitou, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 14/771,287

(22) PCT Filed: Feb. 28, 2014

(86) PCT No.: PCT/JP2014/055888
§ 371 (c)(1),
(2) Date: Aug. 28, 2015

(87) PCT Pub. No.: WO2014/133194
PCT Pub. Date: Sep. 4, 2014

(65) Prior Publication Data
US 2016/0010056 A1    Jan. 14, 2016

Related U.S. Application Data

(60) Provisional application No. 61/771,619, filed on Mar. 1, 2013.

(51) Int. Cl.
*C12N 5/071* (2010.01)
*C12N 5/0735* (2010.01)

(52) U.S. Cl.
CPC ...... *C12N 5/0611* (2013.01); *C12N 2501/115* (2013.01); *C12N 2501/16* (2013.01); *C12N 2501/60* (2013.01); *C12N 2506/02* (2013.01); *C12N 2506/025* (2013.01); *C12N 2510/00* (2013.01)

(58) Field of Classification Search
None
See application file for complete search history.

(56) References Cited

U.S. PATENT DOCUMENTS

2008/0300202 A1* 12/2008 Kentros ............ A01K 67/0275
514/44 R
2013/0143321 A1    6/2013 Saitou et al.

FOREIGN PATENT DOCUMENTS

| EP | 2 169 051 A1 | 3/2010 |
|---|---|---|
| WO | WO 2008/056173 A2 | 5/2008 |
| WO | WO 2012/020687 A1 | 2/2012 |

OTHER PUBLICATIONS

Gillich et al. Graphic abstract, supplemental to the publication-Cell Stem Cell 2012;10:425-39, One Page.*
Bao et al. Cell Stem Cell 2012;11:110-7.*
Brons et at., Nature, 448(7150): 191-195 (2007).
Bucay et al., Stem Cells, 27: 68-77 (2009).
Chu et al., Curr. Biol., 21(20): 1759-1765 (2011).
Clark et al., Human Molecular Genetics, 13(7): 727-739 (2004).
D'Amour et al., Nature Biotechnology, 24(11): 1392-1401 (2006).
Daley, George Q., Science, 316(5823): 409-410-(2007).
Geijsen et al., Nature, 427(6970): 148-154 (2004).
Gillich et al., Cell Stem Cell, 10(4): 425-439 (2012).
Grabole et al., EMBO Rep., 14(7): 629-637 (2013).
Guo et al., Development, 136(7): 1063-1069 (2009).
Hayashi et al., Cell, 146(4): 519-532 (2011).
Hayashi et al., Development, 136(21): 3549-3556 (2009).
Hayashi et al., Science, 338(6109): 971-975 (2012).
Hubner et al., Science, 300(5623): 1251-1256 (2003).
James et al., Development, 132(6): 1273-1282 (2005).
John et al., Exp. Cell. Res., 315(7): 1077-1084 (2009).
Jung et al., Stem Cells, 23: 689-698 (2005).
Kee et al., Stem Cells and Development, 15: 831-837 (2006).
Kee et al., Nature, 462: 222-225 (2009).
Kurimoto et al., Genes & Development, 22(12): 1617-1635 (2008).
Kurimoto et al., Cell Cycle, 7(22): 3514-3518 (2008).
Lawson et al., Genes Dev., 13(4): 424-436 (1999).
Leitch et al., Nat. Struct. Mol. Biol., 20(3): 311-316 (2013).
Magnusdottir et al., Nat. Cell Biol., 15(8): 905-915 (2013).
Mathews et al., Cell Stem Cells, 5: 11-14 (2009).
Morita-Fujimura et al., Develop. Growth. Differ., 51: 567-583 (2009).
Nakaki et al., Nature, 501(7466): 222-226 (2013).
Nagamatsu et al., J. Biol. Chem., 286(12): 10641-10648 (2011).
Nayernia et al., Developmental Cell, 11(1): 125-132 (2009).
Ohinata et al., Cell, 137(3): 571-584 (2009).
Ohinata et al., Nature, 436: 207-213 (2005).
Park et al., Stem Cells, 27: 783-795 (2009).
Pearson et al., Development, 135(8): 1525-1535 (2008).
Saitou et al., Reproduction, 139(6): 931-942 (2010).
Tesar et al., Nature, 448(7150): 196-199 (2007).
Tilgner et al., Stem Cells, 26: 3075-3085 (2008).
Toyooka et al., Proc. Natl. Acad. Sci. USA, 100(20): 11457-11462 (2003).
Vincent et al., Development, 132(6): 1315-1325 (2005).
West et al., Nature, 460: 909-913 (2009).
Yamaji et al., Nature Genetics, 40(8): 1016-1022 (2008).

(Continued)

*Primary Examiner* — Janice Li
(74) *Attorney, Agent, or Firm* — Leydig, Voit & Mayer, Ltd.

(57) ABSTRACT

This invention provides a method of producing a primordial germ cell-like cell (PGCLC) from an epiblast isolated from an embryo or an epiblast-like cell (EpiLC) induced from a pluripotent stem cell (PSC), which comprises allowing the epiblast or EpiLC to express exogenous transcription factor(s) selected from the group consisting of: (i) Blimp1, Prdm14 and Tfap2c; ii) Blimp1 and Prdm14; (iii) Blimp1 and Tfap2c; (iv) Prdm14 and Tfap2c; and (v) Prdm14; thereby inducing the epiblast or EpiLC into a PGC state without acquiring transient mesodermal program.

17 Claims, 10 Drawing Sheets
(10 of 10 Drawing Sheet(s) Filed in Color)

(56) References Cited

OTHER PUBLICATIONS

European Patent Office, Extended European Search Report in European Patent Application No. 11816353.4 (dated Mar. 19, 2014).
Japanese Patent Office, International Search Report in International Patent Application No. PCT/JP2011/067816 (dated Nov. 8, 2011).
Japanese Patent Office, International Search Report in International Patent Application No. PCT/JP2014/055888 (dated May 27, 2014).
Gillich et al., "Epiblast Stem Cell-Based System Reveals Reprogramming Synergy of Germline Factors," *Cell Stem Cell*, 10(4): 425-439 and supplemental information (2012).
U.S. Appl. No. 13/816,681, filed Feb. 21, 2013.
Buta et al., *Stem Cell Research*, 11: 552-562 (2013).
Gomez et al., *Theriogenology*, 74: 498-515 (2010).
Jean et al., *Development, Growth Differentiation*, 55: 41-51 (2013).
Umass Medical School, *International Stem Cell Registry*, hES Cell Line: H9 (WA09), summary information (2016) [downloaded from www.iscr-admin.com/Default.aspx?Action=viewsc&StemCell-Line=89].

\* cited by examiner

US 10,023,838 B2

METHOD OF INDUCING DIFFERENTIATION FROM PLURIPOTENT STEM CELLS TO GERM CELLS

CROSS-REFERENCE TO RELATED APPLICATIONS

This patent application is the U.S. national phase of International Patent Application No. PCT/JP2014/055888, filed Feb. 28, 2014, which claims the benefit of U.S. Provisional Patent Application No. 61/771,619, filed on Mar. 1, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 113,811 bytes ASCII (Text) file named 721764CorrectedSequenceListing created Aug. 31, 2017.

TECHNICAL FIELD OF THE INVENTION

The present invention relates to a method of inducing primordial germ cell-like cells from epiblast-like cells using transcription factor(s), a reagent therefor containing the transcription factor(s), a cell population containing primordial germ cell-like cells obtained from the method and a method of inducing cells belonging to the germ cell lineage from the cell population.

BACKGROUND OF THE INVENTION

The germ cell lineage ensures the continuity of life through the generation of male and female gametes, which unite to form a totipotent zygote. Germ cell specification and development are vital in reproduction and heredity. In mice, primordial germ cells (PGCs), precursors both for spermatozoa and oocytes, arise in the epiblasts in response to cytokines, including, most importantly, bone morphogenetic protein 4 (BMP4), from extraembryonic tissues (non-patent documents 1 and 2). We have recently established a culture system to induce embryonic stem cells (ESCs)/induced pluripotent stem cells (iPSCs) into epiblast-like cells (EpiLCs) using cytokines including activin A (ActA) and basic fibroblast growth factor (bFGF), and then into primordial germ cell-like cells (PGCLCs) using cytokines including BMP4 (patent document 1, non-patent documents 3 and 4). Male and female PGCLCs bear full potential for spermatogenesis and oogenesis, and thus may have potential for unveiling the mechanism of and regulating the germ-cell specification pathway and subsequent development in vitro (patent document 1, non-patent documents 3 and 4).

In replace of cytokines, forced expression of exogenous transcription factors (TFs) may activate endogenous key transcription circuitry for PGC specification. However, our previous studies revealed that PGC specification involves complex regulation of a large number of genes, while some key TFs were identified (non-patent document 5). Accordingly, the TFs sufficient for the induction of germ cell fate and the precise mechanism of action of key TFs remain unknown.

PRIOR ART REFERENCES CITED

Patent Documents

1. WO 2012/020687

Non-Patent Documents

1. Lawson, K. A. et al. Bmp4 is required for the generation of primordial germ cells in the mouse embryo. *Genes Dev* 13, 424-436. (1999).
2. Ohinata, Y. et al. A signaling principle for the specification of the germ cell lineage in mice. *Cell* 137, 571-584 (2009).
3. Hayashi, K., Ohta, H., Kurimoto, K., Aramaki, S. & Saitou, M. Reconstitution of the mouse germ cell specification pathway in culture by pluripotent stem cells. *Cell* 146, 519-532 (2011).
4. Hayashi, K. et al. Offspring from oocytes derived from in vitro primordial germ cell-like cells in mice. *Science* 338, 971-975 (2012).
5. Kurimoto, K. et al. Complex genome-wide transcription dynamics orchestrated by Blimp1 for the specification of the germ cell lineage in mice. *Genes Dev* 22, 1617-1635 (2008).

SUMMARY OF THE INVENTION

Therefore, an object of the present invention is to provide a method of inducing PGCLCs, which are competent for generating normal germ cells and healthy offsprings, from epiblasts of culture equivalents thereof (i.e., EpiLCs) with high efficiency and reproducibility, without cytokines, but using forced expression of exogenous TFs. It is another object of the present invention to provide a reagent for inducing PGCLCs from epiblasts or EpiLCs containing the TFs that allow epiblasts/EpiLCs to activate endogenous key transcription circuitry for PGC specification, or nucleic acids encoding the same.

To this end, we set out to explore TFs whose forced expression may be sufficient to confer the PGC fate onto EpiLCs, based on the system for recapitulating the mammalian germ-cell specification pathway in vitro we reported previously (patent document 1, non-patent documents 3 and 4, supra). We decided to focus on three TFs, Blimp1 (also known as Prdm1), Prdm14 and Tfap2c (also known as AP2γ), since these factors are expressed in epiblasts/EpiLCs stimulated by BMP4 (see for example, FIG. 2b). First, we derived ESCs expressing mVenus and ECFP under the control of Blimp1 and stella (also known as Dppa3/Pgc7) regulatory elements (BVSC), respectively (Reproduction 136, 503-514 (2008)), and reverse tetracycline transactivator (rtTA) under the control of the constitutively active Rosa26 locus (Cell 121, 465-477 (2005))(BVSCR26rtTA ESCs) (FIG. 1a). During development, Blimp1 expression signifies the onset of PGC specification, whereas stella begins expression in the established PGCs (Nature 436, 207-213 (2005); Nature 418, 293-300 (2002); Mech Dev 113, 91-94. (2002)), and the BVSC expression is a faithful indicator for PGC specification and development both in vivo and in vitro (Cell 146, 519-532 (2011); Science 338, 971-975 (2012); Reproduction 136, 503-514 (2008)). Next, we constructed piggyBac transposon-based vectors expressing Blimp1, Prdm14 or Tfap2c under the control of tetracycline regulatory elements (TREs) (FIG. 5d) and infected the BVSCR26rtTA ESCs (XY karyotype) (FIG. 5a-c) with these vectors to isolate BVSCR26rtTA ESCs bearing transgenes for all three TFs (BVSCR26rtTA BP14A cells), two of the three TFs (BVSCR26rtTA BP14, BA and P14A cells), or one of the three TFs (BVSCR26rtTA B, P14, and A cells) (FIG. 1a, FIG. 5d, e).

We induced the TF-infected BVSCR26rtTA ESCs into EpiLCs using ActA and bFGF (Cell 146, 519-532 (2011); Science 338, 971-975 (2012)), and then cultured in the absence of cytokines relevant to PGCLC induction (BMP4, LIF, SCF, BMP8b and EGF; Cell 146, 519-532 (2011); Science 338, 971-975 (2012)) with doxycycline (Dox). As a result, simultaneous over-expression of three TFs (Blimp1, Prdm14 and Tfap2c; BP14A) or two of the three TFs (BP14, BA and P14A) directs EpiLCs swiftly and highly efficiently into a PGC state with endogenous transcription circuitry. The induction of the PGC state on EpiLCs minimally requires Prdm14 (P14) but not Blimp1 (B) or Tfap2c (A).

Quantitative PCR (Q-PCR) and global gene expression analyses revealed that the TF-induced PGC state reconstitutes key transcriptome and epigenetic reprogramming in PGCs, but bypasses a mesodermal program that accompanies PGC specification in vivo and in vitro by cytokines including BMP4.

Importantly, the TF-induced PGCLCs robustly contribute to spermatogenesis and fertile offspring.

We conducted further investigations based on these findings, and have developed the present invention.

Accordingly, the present invention provides the following.

[1] A method of producing a primordial germ cell-like cell (PGCLC) from an isolated epiblast or epiblast-like cell (EpiLC), which comprises allowing the epiblast or EpiLC to express exogenous transcription factor(s) selected from the group consisting of:
(i) Blimp1, Prdm14 and Tfap2c;
(ii) Blimp1 and Prdm14;
(iii) Blimp1 and Tfap2c;
(iv) Prdm14 and Tfap2c; and
(v) Prdm14;
thereby inducing the epiblast or EpiLC into a PGC state without acquiring transient mesodermal program.

[2] The method according to [1] above, wherein the exogenous transcription factor(s) or nucleic acid(s) encoding the same is/are introduced into the epiblast or EpiLC.

[3] The method according to [1] above, wherein the nucleic acid(s) encoding the exogenous transcription factor(s) has/have been introduced into the epiblast or EpiLC, in a form capable of being conditionally expressed, prior to the induction of the epiblast or EpiLC.

[4] The method according to [3] above, wherein the epiblast or EpiLC is cultured under conditions which the nucleic acid(s) encoding the exogenous transcription factor(s) is/are expressed for 1 to 5 days.

[5] The method according to any one of [1] to [4] above, wherein the EpiLC is obtained by culturing a pluripotent stem cell (PSC) in the presence of activin A (ActA), optionally in the presence of further basic fibroblast growth factor (bFGF) and/or Knockout™ Serum Replacement (KSR).

[6] The method according to [5] above, wherein the PSC is an embryonic stem cell (ESC) or induced pluripotent stem cell (iPSC).

[7] The method according to any one of [1] to [6] above, wherein the nucleic acid(s) encoding the exogenous transcription factor(s) is in a form capable of disappearing from the PGCLC.

[8] The method according to [7] above, wherein the nucleic acid(s) is/are carried on vector(s) selected from the group consisting of plasmid, episomal vector, transposon, adenoviral vector and Sendai viral vector.

[9] The method according to any one of [1] to [8] above, wherein the EpiLC is derived from mouse or human.

[10] A reagent for inducing an isolated epiblast or EpiLC into a PGCLC comprising transcription factor(s) selected from the group consisting of:
(i) Blimp1, Prdm14 and Tfap2c;
(ii) Blimp1 and Prdm14;
(iii) Blimp1 and Tfap2c;
(iv) Prdm14 and Tfap2c;
(v) Prdm14; or nucleic acid(s) encoding the transcription factor(s).

[11] The reagent according to [10] above, wherein the nucleic acid(s) encoding the transcription factor(s) is/are in a form capable of being conditionally expressed in the epiblast or EpiLC.

[12] An isolated epiblast or EpiLC comprising nucleic acid(s) encoding exogenous transcription factor(s) selected from the group consisting of:
(i) Blimp1, Prdm14 and Tfap2c;
(ii) Blimp1 and Prdm14;
(iii) Blimp1 and Tfap2c;
(iv) Prdm14 and Tfap2c; and
(v) Prdm14;
wherein the nucleic acid(s) is/are in a form capable of being conditionally expressed in the epiblast or EpiLC.

[13] An isolated PSC comprising nucleic acid(s) encoding exogenous transcription factor(s) selected from the group consisting of:
(i) Blimp1, Prdm14 and Tfap2c;
(ii) Blimp1 and Prdm14;
(iii) Blimp1 and Tfap2c;
(iv) Prdm14 and Tfap2c; and
(v) Prdm14;
wherein the nucleic acid(s) is/are in a form capable of being conditionally expressed in an EpiLC differentiated from the PSC.

[14] A kit for inducing an isolated epiblast or EpiLC into a PGCLC comprising the epiblast or EpiLC according to [12] above; and a reagent that allows the epiblast or EpiLC to express the exogenous transcription factor(s).

[15] A kit for inducing an isolated PSC into a PGCLC comprising the PSC according to [13] above; a reagent for inducing the PSC into an EpiLC comprising ActA and optionally bFGF and/or KSR;
and a reagent that allows the EpiLC to express the exogenous transcription factor(s).

[16] A method of producing a PGCLC from a PSC, which comprises the following steps I) and II):
I) the step for producing an EpiLC by culturing a PSC in the presence of ActA, optionally in the presence of further bFGF and/or KSR;
II) the step for inducing the EpiLC obtained in the step I) into a PGCLC by the method according to any one of [1] to [9] above.

[17] The method according to [16] above, which further comprises:
III) the step for selecting a Blimp1-positive cell from the cells obtained in the step II).

[18] A method of producing a variety of cell types derived from epiblast which comprises utilizing the PGCLC cell population obtained by the method according to [16] or [17] above as a cell source.

Here we show that, without cytokines including BMP4, simultaneous over-expression of three TFs, Blimp1, Prdm14 and Tfap2c, directs EpiLCs swiftly and highly efficiently into a PGC state with endogenous transcription circuitry. Furthermore, the TF-induced PGCLCs robustly contribute to spermatogenesis and fertile offspring. In view of clinical application (e.g., fertility treatment), it is highly desirable to prepare germ cells under serum-free and xeno-free conditions. Since human recombinant cytokines are expensive, the present invention contributes to reduce the cost of germ cell production for human therapy.

Our findings provide not only a novel insight into the transcriptional logic that creates a germ cell state, but also a foundation for the TF-based reconstitution and regulation of mammalian gametogenesis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1a, Scheme for the BVSCR26rtTA cells and the piggyBac transposon-based vectors with tetracycline-responsive promoters driving transcription factor and β-geo expression. FIG. 1b, Induction of BVSC with (top) or without (bottom) Dox (1.5 µg/ml) in floating aggregates of EpiLCs induced from BVSCR26rtTA BP14A cells during the 6-day observation period. Bar, 200 µm. FIG. 1c, FACS analysis of BVSC induction by Dox (1.5 µg/ml) in floating aggregates of EpiLCs induced from BVSCR26rtTA BP14A cells (Line 3~3) (top) or parental BVSCR26rtTA cells (bottom). FIG. 1d, Expression of the indicated genes measured by Q-PCR in TF (BP14A)- or cytokine-induced BV-positive cells (red and orange, respectively) or in the whole aggregates of EpiLCs from parental BVSCR26rtTA cells with Dox (grey) during the 4-day observation period. For each gene, the ΔCt from the average Ct values of two independent housekeeping genes, Arbp and Ppia, is shown on the log 2 scale. For each gene, mean value of two independent experiments with two technical replicates is shown. FIG. 1e, Efficiencies of BVSC induction at d2 plotted against whole exogenous TF transcript levels 12 hrs after induction in a number of independent clones of the indicated cells.

FIG. 2a, Induction of BVSC at day 2 by Dox (1.5 µg/ml) in BVSCR26rtTA BP14A (Line 3-3)-derived EpiLCs or by BMP4 (500 ng/ml) in parental BVSCR26rtTA-derived EpiLCs without or with an inhibitor for ALK2/3, LDN193189 (120 pM). Negative controls without induction are shown on the right. Bar, 200 µm. FIG. 2b, Expression of the indicated genes at day 2 in whole EpiLC aggregates induced by Dox (BVSCR26rtTA BP14A cells) or BMP4 (BVSCR26rtTA cells) without or with LDN193189. For each gene, the ΔCt from the average Ct values of two independent housekeeping genes, Arbp and Ppia, is shown on the log 2 scale. FIG. 2c, Induction of BVSC at day 2 with or without Dox in floating aggregates of BVSCR26rtTA BP14A ESCs (top) or EpiLCs (bottom). Bar, 200 µm. FIG. 2d, FACS analysis of BVSC induction in the cells shown in FIG. 2c.

FIG. 3a, PCA of the indicated cells. FIG. 3b, Immunofluorescence analysis of H3K9me2 (top) or H3K27me3 (bottom) levels (red) in d4 BV-positive TF (BP14A)-PGCLCs (GFP-positive, delineated by dotted lines, Line 3-3) compared to those in EpiLCs (DNMT3B-positive, Line 3~3). DAPI staining is shown on the left. Bar, 20 µm. FIG. 3c, Bisulfite sequence analysis of methylated cytosine in the differentially methylated regions (DMRs) of the imprinted genes in EpiLCs and d4 BV-positive TF (BP14A, Line 3-3)-PGCLCs. White and black circles represent unmethylated and methylated cytosines.

FIG. 4a, FACS of BV-positive TF (BP14A, Line 3-10)-PGCLCs for injection into seminiferous tubules. FIG. 4b, Seminiferous tubules of a W/W$^v$ mouse injected by TF-PGCLCs showing spermatogenesis. An arrow indicates an empty tubule. Bar, 500 µm. FIG. 4c, Hematoxylin-eosin staining of a section of a W/W$^v$ mouse testis injected with TF-PGCLCs showing apparently normal spermatogenesis. The asterisk indicates an empty tubule. Bar, 50 µm. FIG. 4d, Spermatozoa (arrows) from TF-PGCLCs. Bar, 50 µm. FIG. 4e, Zygotes at pronuclear stages generated by injection of TF-PGCLC-derived sperm into wild-type oocytes by ICSI. Bar, 50 µm. FIG. 4f, 2-cell embryos from zygotes in FIG. 4e. Bar, 50 µm. FIGS. 4g and 4h, Apparently normal offspring (g, h) and placenta (g) derived from TF-PGCLC-derived sperm. FIG. 4i, Genotyping of the offspring from TF-PGCLC-derived sperm by exogenous TFs, BVSC, and R26rtTA. FIG. 4j, A fertile female derived from TF-PGCLC-derived sperm. FIG. 4k, Spermatogenesis by TF (BP14A)- or Ck-PGCLCs.

FIG. 5a, Chimeras generated by parental BVSCR26rtTA ESCs. FIG. 5b, Rate for the birth of chimeric offspring with parental BVSCR26rtTA ESCs. FIG. 5c, Germline transmission in chimeras of parental BVSCR26rtTA ESCs. FIG. 5d, Schematic representation of the piggyBac transposon-based vector bearing a tetracycline responsive promoter driving the expression of a cloned gene together with β-geo. Blimp1, Prdm14, and Tfap2c were cloned between attB1 and attB2 and are expressed together with β-geo through IRES (internal ribosomal entry sequence). FIG. 5e, Southern blot analysis for the estimation of the copy number of the integrated piggyback transposon vector in each BVSCR26rtTA transfectant. A fragment of β-geo downstream of the BamHI site indicated by the black bar was used as a probe. The estimated copy number for each transfectant is indicated at the bottom.

FIG. 6a, Scheme for the induction of key TFs by Dox in floating aggregates of EpiLCs induced from ESCs. Since the parental BVSCR26rtTA ESC-derived EpiLCs induced for 36 hrs exhibited the most efficient PGCLC induction by cytokines, we consistently used EpiLCs induced for 36 hrs from the transfectants of the BVSCR26rtTA ESCs for the induction of key TFs by Dox. FIG. 6b, Expression levels of the indicated genes in BV-positive cells of the floating aggregates of EpiLCs from BVSCR26rtTA BP14A cells (Line 3-3) induced by Dox for 12 hrs. For each gene, the ΔCT from the average CT values of two independent housekeeping genes, Arbp and Ppia, is shown on the log 2 scale. For each gene, mean value of two independent experiments with two technical replicates is shown. See also FIG. 8. FIG. 6c, β-galactosidase staining of dissociated single cells of floating aggregates of EpiLCs from BVSCR26rtTA BP14A cells with or without Dox for 12 hrs. Bar, 20 µm. See also FIG. 8. FIG. 6d, Dox-dose-dependent induction of BVSC in floating aggregates of EpiLCs induced from BVSCR26rtTA BP14A ESCs (Line 3-10). Bright field (BF) images and immunofluorescence images for BV and SC of floating aggregates of EpiLCs treated with the indicated concentrations of Dox (μg/ml) or the cytokines [BMP4 (500 ng/ml), LIF (1000 U/ml), BMP8A (500 ng/ml), SCF (100 ng/ml), EGF (50 ng/ml)] for 2 days are shown. Bar, 200 μm. FIG. 6e, Percentage of BV- and BVSC-positive cells determined by FACS in the floating aggregates of EpiLCs shown in FIG. 6d. FIG. 6f, Cytokine-induced BVSC expression during the 6-day period in floating aggregates of EpiLCs from parental BVSCR26rtTA ESCs. Bar, 200 μm.

FIG. 7a, Induction of BVSC at day 2 with (left) or without (right) Dox (1.5 μg/ml) in floating aggregates of EpiLCs induced from BVSCR26rtTA BP14A, BP14, BA, P14A, B, P14, and A cells and from the parental BVSCR26rtTA cells. Results of three independent clones from each cell type are shown. Bar, 200 μm. FIG. 7b, Induction of BVSC at day 2 and 4 analyzed on FACS in floating aggregates of EpiLCs induced from BVSCR26rtTA BP14, BA, P14A, B, P14, and A cells. The clone numbers used for the analysis are shown in parentheses. FIG. 7c, Percentage of BVSC-positive cells determined by FACS in floating aggregates of EpiLCs shown in FIG. 7a. Mean values with value ranges from at least two independent experiments for each line are shown. FIG. 7d, Expression of the indicated genes measured by Q-PCR in TF (BP14A, BP14, BA, P14A, P14)- or cytokine-induced BV-positive cells or in the whole aggregates of EpiLCs from parental BVSCR26rtTA cells with Dox during the 4-day period. For each gene, the ΔCT from the average CT values of two independent housekeeping genes, Arbp and Ppia, is shown on the $\log_2$ scale. For each gene, mean value of two independent experiments with two technical replicates is shown.

FIG. 8a, Quantification of the amplification efficiencies of primer pairs used for the amplification of the indicated sequences. FIG. 8b, Expression levels measured by Q-PCR of the exogenous and endogenous Blimp1, Prdm14, and Tfap2c in whole floating aggregates of EpiLCs from the BVSCR26rtTA BP14A cells or the parental BVSCR26rtTA cells induced by Dox, or from the parental BVSCR26rtTA cells induced by the cytokines during the course of 48 hrs. For each gene, the ΔCT from the average CT values of two independent housekeeping genes Arbp and Ppia is shown on the $\log_2$ scale. For each gene, mean value of two independent experiments with two technical replicates is shown. FIG. 8c, Percentage of β-galactosidase-positive cells in dissociated single cells of floating aggregates of EpiLCs from BVSCR26rtTA BP14A, BP14, BA, P14A, B, P14, and A cells with or without Dox for 12 hrs. FIG. 8d, 8e, 8f, 8g, Measurements of the expression levels of β-galactosidase (reflecting whole exogenous TF transcript levels, d), exogenous Blimp1 (e), Prdm14 (f), and Tfap2c (g) in whole floating aggregates of EpiLCs from BVSCR26rtTA BP14A (clones 3-3, 3-6, 3-10), BP14 (clones 4-2, 4-6, 4-7), BA (clones 5-3, 5-4, 5-10), P14A (clones 6-1, 6-2, 6-4, 6-5), B (clones 2-1, 2-4, 2-6), P14 (clones 7-1, 7-5, 7-8), and A (clones 8-2, 8-4, 8-7) cells induced by Dox for 12 hrs. The mean values with standard deviations (SDs) from at least two independent experiments for each line are shown. Note that the whole exogenous transcript levels measured by β-galactosidase are nearly equal to the sum of the levels of each exogenous TF measured by specific primers for each TF expressed in each clone.

FIG. 9a, FACS of the cells used for global transcription analysis by the microarray shown in FIG. 3a. The BV-positive cells delineated by red squares were used for the microarray analysis. FIG. 9b, (top) Genes up-regulated in d2 TF(BP14A)-PGCLCs in comparison to those in EpiLCs/control EpiLCs without exogenous TFs but treated with Dox ("core PGC genes"). (bottom) Genes up-regulated in d2 Ck-PGCLCs but not in d2 TF-PGCLCs in comparison to those in EpiLCs ("somatic mesodermal genes"). The expression levels defined by the microarray analysis are represented by a graded color code as shown at the bottom. The symbols for key genes are shown on the right. At least two independent samples were used for the analysis. FIG. 9c, FACS analysis of EpiLCs and d4 BV-positive TF (BP14A, Line 3-3)-PGCLCs used in FIG. 3b.

FIG. 10a, A testis (right) transplanted with the SC-positive cells induced by activation of BP14A in ESCs. As a control, an untransplanted testis is shown on the left. Bar, 1 mm. FIG. 10b, A histological section stained by hematoxylin-eosin of a testis bearing the SC-positive cell-derived teratoma. The areas delineated in black squares in the left panel are magnified in the right panels. (right, top) A ciliated endoderm-like cell lining and bone with bone marrow bearing hematopoietic cells are formed. (right, bottom) Well-differentiated neurons and neural fibers are eminent. Bars: (the left panel), 100 μm, (the right panels), 100 μm. FIG. 10c, Development of embryos derived from TF (BP14A)- and Ck-PGCLC-derived spermatozoa. FIG. 10d, Growth of offspring derived from TF (BP14A)- and Ck-PGCLC-derived spermatozoa. FIG. 10e, Fertility of mice (indicated by numbers, FIG. 4i) derived from TF (BP14A)-derived spermatozoa.

DETAILED DESCRIPTION OF THE INVENTION

Figure 1:
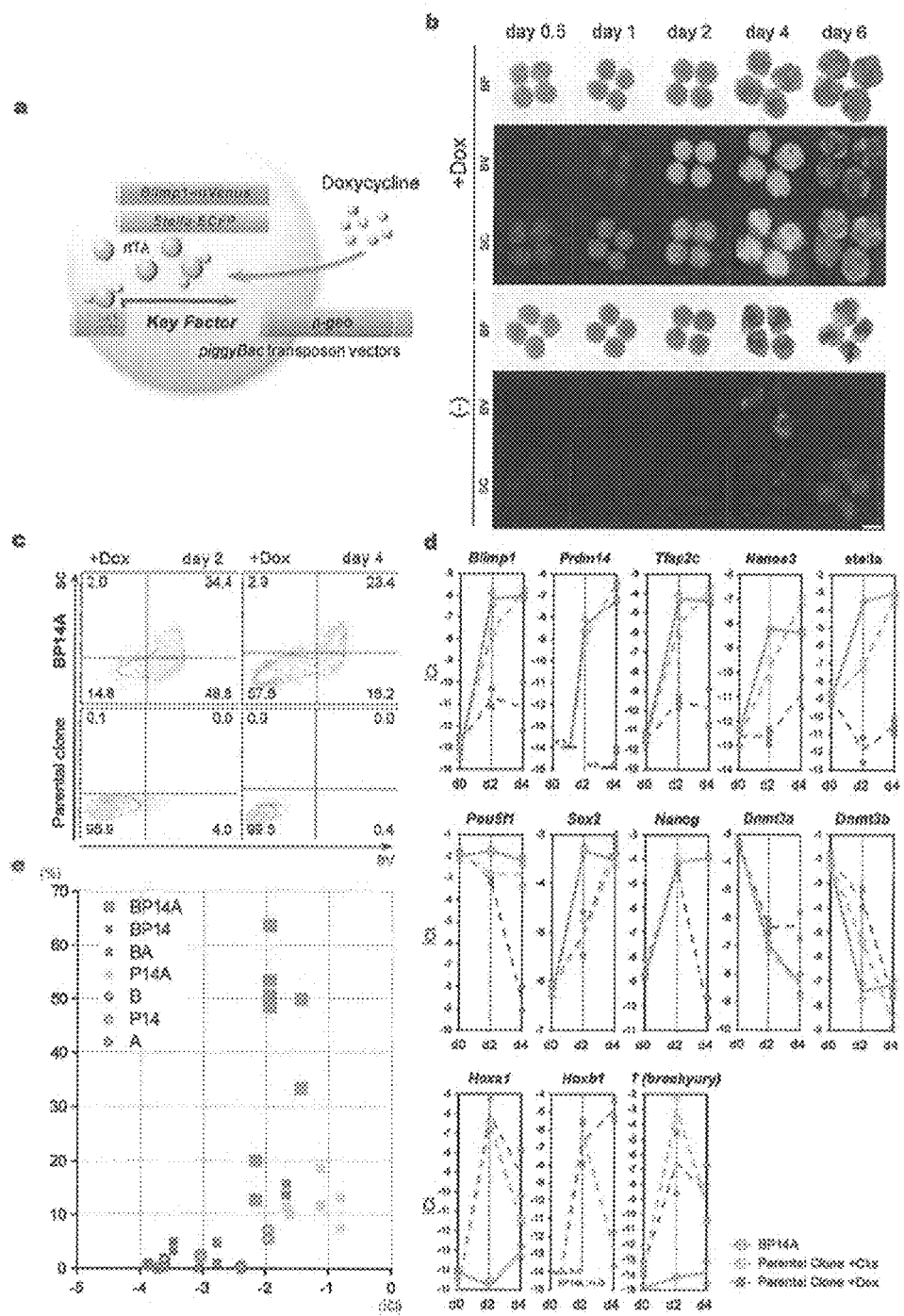
FIG. 1 shows an induction of a PGC-like state by transcription factors.

(I) Method of Producing PGCLCs from Epiblasts or EpiLCs

The present invention provides a method of producing PGCLCs from isolated epiblasts or EpiLCs, which comprises allowing the epiblasts or EpiLCs to express certain exogenously introduced TF(s) that show specific expression in PGCs, without cytokines such as BMP4, LIF, SCF, BMP8b and EGF.

(Ia) Epiblasts and Preparation Thereof

The "epiblast" for use as the starting material is a pre-gastrulating epiblast cell (in mice, from embryonic day (E) 5.5 to E6.0 but not those later than E6.25) derived from inner cell mass of a mammalian (e.g., mouse, human, monkey, rat, rabbit, bovine, horse, porcine, canine, sheep, goat, etc., preferably mouse and human) blastocyst. The epiblasts used in the present invention can be prepared by isolating mammalian embryos in an appropriate buffer, treating the embryos with trypsin/pancreatin, removing visceral endoderm (VE) by pipetting and cutting off extraembryonic ectoderm (ExE) by a glass needle. Isolated epiblasts can be cultured in a serum-free medium supplemented with 10-20% KSR and the like.

(Ib-1) EpiLCs

The "epiblast-like cell (EpiLC)" for use as the starting material is a culture equivalent of pre-gastrulating epiblast cell derived from a pluripotent stem cell (PSC). To be specific, the EpiLC is defined as a cell having ether or both of the following properties:
(1) elevated gene expression of at least one selected from Fgf5, Wnt3 and Dnmt3b compared to the PSC before inducing differentiation;
(2) reduced gene expression of at least one selected from Gata4, Gata6, Sox17 and Blimp1 compared to the PSC before inducing differentiation.

More preferably, the EpiLC of the present invention has the following properties:
(1) continuous gene expression of Oct3/4;
(2) reduced gene expression of Sox2 and Nanog compared to the PSC before inducing differentiation;
(3) elevated gene expression of Fgf5, Wnt3 and Dnmt3b compared to the PSC before inducing differentiation; and
(4) reduced gene expression of Gata4, Gata6, Sox17 and Blimp1 compared to the PSC before inducing differentiation.

(Ib-2) Induction of Differentiation from PSCs to EpiLCs

The EpiLC of the present invention can be prepared from a PSC as previously described (WO 2012/020687; *Cell* 146, 519-532 (2011); *Science* 338, 971-975 (2012)).

(Ib-2(i)) PSCs and Preparation Thereof

The "pluripotent stem cell (PSC)" for use as the starting, material may be any undifferentiated cell possessing a "self-renewal" that enables it to proliferate while retaining the undifferentiated state, and "pluripotency" that enables it to differentiate into all the three primary germ layers of the embryo. Examples include embryonic stem (ES) cell, embryonic stem cell derived from a cloned embryo obtained by nuclear transplantation (ntES cell), germline stem cell ("GS cell"), embryonic germ cell ("EG cell"), induced pluripotent stem (iPS) cell, cultured fibroblast- or myeloid stem cell-derived pluripotent cell (Muse cell) and the like. Preferable pluripotent stem cells are ES cell, ntES cell and iPS cell.

(A) Embryonic Stem Cell

ES cell is a stem cell having pluripotency and proliferation potency based on self-renewal, which is established from an inner cell mass of an early-stage embryo (for example, blastocyst) of a mammal such as human, mouse and the like.

ES cell is an embryo-derived stem cell derived from an inner cell mass of blastocyst, which is an embryo after morula at 8-cell stage of a fertilized egg, and has an ability to differentiate into any cell constituting an adult body, i.e., pluripotent differentiation potency, and proliferation potency based on self-renewal. The ES cell was discovered in mouse in 1981 (M. J. Evans and M. H. Kaufman (1981), Nature 292:154-156) and thereafter ES cell lines were also established in primates such as human, monkey and the like (J. A. Thomson et al. (1998), Science 282:1145-1147; J. A. Thomson et al. (1995), Proc. Natl. Acad. Sci. USA, 92: 7844-7848; J. A. Thomson et al. (1996), Biol. Reprod., 55: 254-259; J. A. Thomson and V. S. Marshall (1998), Curt. Top. Dev. Biol., 38:133-165).

ES cell can be established by removing an inner cell mass from the blastocyst of a fertilized egg of a target animal, and culturing the inner cell mass on fibroblast feeder cells. In addition, the cells can be maintained by passage culture using a culture medium added with substances such as leukemia inhibitory factor (LIF), basic fibroblast growth factor (bFGF) and the like. The methods of establishment and maintenance of human and monkey ES cells are described in, for example, U.S. Pat. No. 5,843,780; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; H. Kawasaki et al. (2002), Proc. Natl. Acad. Sci. USA, 99:1580-1585; Klimanskaya I, et al. (2006), Nature. 444:481-485 and the like.

Using, as a culture medium for preparing ES cells, for example, a DMEM/F-12 culture medium supplemented with 0.1 mM 2-mercaptoethanol, 0.1 mM nonessential amino acids, 2 mM L-glutamic acid, 20% KSR and 4 ng/ml bFGF, human ES cells can be maintained under wet atmosphere at 37° C., 2% $CO_2$/98% air (O. Fumitaka et al. (2008), Nat. Biotechnol., 26:215-224). In addition, ES cells require passage every 3-4 days, and the passage in this case can be performed using, for example, 0.25% trypsin and 0.1 mg/ml collagenase IV in PBS containing 1 mM $CaCl_2$ and 20% KSR.

ES cells can be generally selected by the Real-Time PCR method using the expression of a gene marker such as alkaline phosphatase, Oct-3/4, Nanog and the like as an index. Particularly, for selection of human ES cell, expression of a gene marker such as OCT-3/4, NANOG, ECAD and the like can be used as an index (E. Kroon et al. (2008), Nat. Biotechnol., 26:443-452).

As for human ES cell line, for example, WA01(H1) and WA09(H9) are available from WiCell Research Institute, and KhES-1, KhES-2 and KhES-3 are available from Institute for Frontier Medical Sciences, Kyoto University (Kyoto, Japan).

(B) Germline Stem Cell

Germline stem cell is a pluripotent stem cell derived from the testis, which becomes the origin for spermatogenesis. This cell can be differentiation induced into various lines of cells, like ES cells and shows properties of, for example, generation of a chimeric mouse by transplantation into a mouse blastocyst and the like (M. Kanatsu-Shinohara et al. (2003) Biol. Reprod., 69:612-616; K. Shinohara et al. (2004), Cell, 119:1001-1012). It is self-renewable in a culture medium containing a glial cell line-derived neurotrophic factor (GDNF), can produce a germline stem cell by repeating passages under culture conditions similar to those for ES cells (Masanori Takehashi et al., (2008), Experimental Medicine, Vol. 26, No. 5(Suppl.), pp. 41-46, YODOSHA (Tokyo, Japan)).

(C) Embryonic Germ Cell

Embryonic germ cell is a cell having pluripotency similar to that of ES cells, which is established from a primordial germ cell at the prenatal period. It can be established by culturing a primordial germ cell in the presence of a substance such as LIF, bFGF, a stem cell factor and the like (Y. Matsui et al. (1992), Cell, 70:841-847; J. L. Resnick et al. (1992), Nature, 359:550-551).

(D) Induced Pluripotent Stem Cell

Induced pluripotent stem (iPS) cell is an artificial stem cell derived from a somatic cell, which can be produced by introducing a specific reprogramming factor in the form of a DNA or protein into a somatic cell, and show almost equivalent property (e.g., pluripotent differentiation and proliferation potency based on self-renewal) as ES cells (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO2007/069666). The reprogramming factor may be constituted with a gene specifically expressed by ES cell, a gene product or non-coding RNA thereof, a gene playing an important role for the maintenance of undifferentiation of ES cell, a gene product or non-coding RNA thereof, or a low molecular weight compound. Examples of the gene contained in the reprogramming factor include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, TbX3, Glis1 and the like. These reprogramming factors may be used alone or in combination. Examples of the combination of the reprogramming factors include combinations described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, WO2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), Stem Cells. 28:713-720, and Maekawa M, et al. (2011), Nature. 474:225-9.

Examples of the above-mentioned reprogramming factor include, but are not limited to, factors used for enhancing the establishment efficiency, such as histone deacetylase (HDAC) inhibitors [e.g., low-molecular inhibitors such as valproic acid (VPA), trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], MEK inhibitor (e.g., PD184352, PD98059, U0126, SL327 and PD0325901), Glycogen synthase kinase-3 inhibitor (e.g., Bio and CHIR99021), DNA methyl transferase inhibitors (e.g., 5-azacytidine), histone methyl transferase inhibitors [for example, low-molecular inhibitors such as BIX-01294, and nucleic acid-based expression inhibitors such as siRNAs and shRNAs against Suv39h1, Suv39h2, SetDB1 and G9a], L-channel calcium agonist (for example, Bayk8644), butyric acid, TGFβ inhibitor or ALK5 inhibitor (e.g., LY364947, SB431542, 616453 and A-83-01), p53 inhibitor (for example, siRNA and shRNA against p53), ARID3A inhibitor (e.g., siRNA and shRNA against ARID3A), miRNA such as miR-291-3p, miR-294, miR-295, mir-302 and the like, Wnt Signaling (for example, soluble Wnt3a), neuropeptide Y, prostaglandins (e.g., prostaglandin E2 and prostaglandin J2), hTERT, SV40LT, UTF1, IRX6, GLIS1, PITX2, DMRTB1 and the like. In the present specification, these factors used for enhancing the establishment efficiency are not particularly distinguished from the reprogramming factor.

When the reprogramming factor is in the form of a protein, it may be introduced into a somatic cell by a method, for example, lipofection, fusion with cell penetrating peptide (e.g., TAT derived from HIV and polyarginine), microinjection and the like.

When the reprogramming factor is in the form of a DNA, it may be introduced into a somatic cell by the method using, for example, vector of virus, plasmid, artificial chromosome and the like, lipofection, liposome, microinjection and the like. Examples of the virus vector include retrovirus vector, lentivirus vector (Cell, 126, pp. 663-676, 2006; Cell, 131, pp. 861-872, 2007; Science, 318, pp. 1917-1920, 2007), adenovirus vector (Science, 322, 945-949, 2008), adeno-associated virus vector, Sendai virus vector (vector of Hemagglutinating Virus of Japan) (WO 2010/008054) and the like. Examples of the artificial chromosome vector include human artificial chromosome (HAC), yeast artificial chromosome (YAC), bacterial artificial chromosome (BAC, PAC) and the like. As the plasmid, plasmids for mammalian cells can be used (Science, 322:949-953, 2008). The vector can contain regulatory sequences of promoter, enhancer, ribosome binding sequence, terminator, polyadenylation site and the like so that a nuclear reprogramming substance can be expressed and further, where necessary, a selection marker sequence of a drug resistance gene (for example, kanamycin resistance gene, ampicillin resistance gene, puromycin resistance gene and the like), thymidine kinase gene, diphtheria toxin gene and the like, a reporter gene sequence of green fluorescent protein (GFP), β glucuronidase (GUS), FLAG and the like, and the like. Moreover, the above-mentioned vector may have a LoxP sequence before and after thereof to simultaneously cut out a gene encoding a reprogramming factor or a gene encoding a reprogramming factor bound to the promoter, after introduction into a somatic cell.

When in the form of RNA, for example, it may be introduced into a somatic cell by means of lipofection, microinjection and the like, and RNA incorporating 5-methylcytidine and pseudouridine (TriLink Biotechnologies) may be used to suppress degradation (Warren L, (2010) Cell Stem Cell. 7:618-630).

Examples of the culture medium for inducing iPS cell include 10-15% FBS-containing DMEM, DMEM/F12 or DME culture medium (these culture media can further contain LIF, penicillin/streptomycin, puromycin, L-glutamine, nonessential amino acids, β-mercaptoethanol and the like as appropriate) or a commercially available culture medium [for example, culture medium for mouse ES cell culture (TX-WES culture medium, Thromb-X), culture medium for primate ES cell (culture medium for primate ES/iPS cell, Reprocell), serum-free medium (mTeSR, Stemcell Technologies)] and the like.

Examples of the culture method include contacting a somatic cell with a reprogramming factor on 10% FBS-containing DMEM or DMEM/F12 culture medium at 37° C. in the presence of 5% $CO_2$ and culturing for about 2-7 days, thereafter reseeding the cells on feeder cells (e.g., mitomycin C-treated STO cells, SNL cells etc.), and culturing the cells in a bFGF-containing culture medium for primate ES cell from about 10 days after the contact of the somatic cell and the reprogramming factor, whereby iPS-like colonies can be obtained after about 30-about 45 days or longer from the contact.

Alternatively, the cells are cultured on feeder cells (e.g., mitomycin C-treated STO cells, SNL cells etc.) at 37° C. in the presence of 5% 002 in a 10% FBS-containing DMEM culture medium (which can further contain LIF, penicillin/ streptomycin, puromycin, L-glutamine, nonessential amino acids, β-mercaptoethanol and the like as appropriate), whereby ES-like colonies can be obtained after about 25-about 30 days or longer. Desirably, a method using a somatic cell itself to be reprogrammed, or an extracellular substrate (e.g., Laminin-5 (WO2009/123349) and Matrigel (BD)), instead of the feeder cells (Takahashi K, et al. (2009), PLoS One. 4:e8067 or WO2010/137746), can be mentioned.

Besides the above, a culture method using a serum-free medium can also be recited as an example (Sun N, et al. (2009), Proc Natl Acad Sci USA. 106:15720-15725). Furthermore, to enhance establishment efficiency, an iPS cell may be established under hypoxic conditions (oxygen concentration of not less than 0.1% and not more than 15%) (Yoshida Y, et al. (2009), Cell Stem Cell. 5:237-241 or WO2010/013845).

The culture medium is exchanged with a fresh culture medium once a day during the above-mentioned cultures, from day 2 from the start of the culture. While the cell number of the somatic cells used for nuclear reprogramming is not limited, it is about $5\times10^3$-about $5\times10^6$ cells per 100 $cm^2$ culture dish.

The iPS cell can be selected based on the shape of the formed colony. When a drug resistance gene which is expressed in association with a gene (e.g., Oct3/4, Nanog) expressed when a somatic cell is reprogrammed is introduced as a marker gene, an established iPS cell can be selected by culturing in a culture medium (selection culture medium) containing a corresponding drug. When the marker gene is a fluorescent protein gene, iPS cell can be selected by observation with a fluorescence microscope, when it is a luminescent enzyme gene, iPS cell can be selected by adding a luminescent substrate, and when it is a chromogenic enzyme gene, iPS cell can be selected by adding a chromogenic substrate.

The term "somatic cell" used in the present specification means any animal cell (preferably, cells of mammals inclusive of human) excluding germ line cells and totipotent cells such as ovum, oocyte, ES cells and the like. Somatic cell unlimitatively encompasses any of somatic cells of fetuses, somatic cells of neonates, and mature healthy or pathogenic somatic cells, and any of primary cultured cells, passage cells, and established lines of cells. Specific examples of the somatic cell include (1) tissue stem cells (somatic stem cells) such as neural stem cell, hematopoietic stem cell, mesenchymal stem cell, dental pulp stem cell and the like, (2) tissue progenitor cell, (3) differentiated cells such as lymphocyte, epithelial cell, endothelial cell, myocyte, fibroblast (skin cells etc.), hair cell, hepatocyte, gastric mucosal cell, enterocyte, splenocyte, pancreatic cell (pancreatic exocrine cell etc.), brain cell, lung cell, renal cell and adipocyte and the like, and the like.

The choice of mammal individual as a source of somatic cells is not particularly limited; however, when the PGC-like cells as a final product are to be used for the treatment of diseases such as infertility in humans, it is preferable, from the viewpoint of prevention of graft rejection and/or GvHD, that somatic cells are patient's own cells or collected from another person having the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressor and the like. For example, it includes an HLA type wherein major HLAs (the three major loci of HLA-A, HLA-B and HLA-DR or four loci further including HLA-Cw) are identical (hereinafter the same meaning shall apply) and the like. When the PGC-like cells are not to be administered (transplanted) to a human, but used as, for example, a source of cells for screening for evaluating a patient's drug susceptibility or adverse reactions, it is likewise necessary to collect the somatic cells from the patient or another person with the same genetic polymorphism correlating with the drug susceptibility or adverse reactions.

(E) Naive Human ES and iPS Cells

Conventional human ES cells derived from blastocyst-stage embryos have very different biological (morphological, molecular and functional) properties from mouse ES cells. Mouse pluripotent stem cells can exist in two functionally distinct states, LIF-dependent ES cells and bFGF-dependent epiblast stem cells (EpiSCs). Molecular analyses suggest that the pluripotent state of human ES cells is similar to that of mouse EpiSCs rather than that of mouse ES cells. Recently, human ES and iPS cells in a mouse ES cell-like pluripotent state (also refereed to as naive human ES and iPS cells) have been established by ectopic induction of Oct3/4, Sox2, Klf4, c-Myc and Nanog in the presence of LIF (see Cell Stem Cells, 6: 535-546, 2010), or ectopic induction of Oct3/4, Klf4 and Klf2 combined with LIF and inhibitors of GSK3β and ERK1/2 pathway (see Proc. Natl. Acad. Sci. USA, online publication doi/10.1073/pnas.1004584107). These naive human ES and iPS cells may be preferable starting materials for the present invention due to their pluripotent more immature compared to that of conventional human ES and iPS cells.

(F) ES Cells Derived from Cloned Embryo by Nuclear Transplantation nt ES cell is an ES cell derived from a cloned embryo prepared by a nuclear transplantation technique, and has almost the same property as the ES cell derived from a fertilized egg (T. Wakayama et al. (2001), Science, 292:740-743; S. Wakayama et al. (2005), Biol. Reprod., 72:932-936; J. Byrne et al. (2007), Nature, 450:497-502). That is, an ES cell established from an inner cell mass of a blastocyst derived from a cloned embryo obtained by substituting the nucleus of an unfertilized egg with the nucleus of a somatic cell is an nt ES (nuclear transfer ES) cell. For production of an nt ES cell, a combination of the nuclear transplantation technique (J. B. Cibelli et al. (1998), Nature Biotechnol., 16:642-646) and the ES cell production technique (mentioned above) is used (Kiyoka Wakayama et al., (2008), Experimental Medicine, Vol. 26, No. 5(Suppl.), pp. 47-52). In nuclear transplantation, reprogramming can be performed by injecting the nucleus of a somatic cell to an enucleated unfertilized egg of a mammal, and culturing for a few hours.

(G) Multilineage-Differentiating Stress Enduring Cell (Muse Cell)

Muse cell is a pluripotent stem cell produced by the method described in WO2011/007900. In more detail, it is a cell having pluripotency, which is obtained by subjecting a fibroblast or a bone marrow stromal cell to a trypsin treatment for a long time, preferably 8 hr or 16 hr, and thereafter culturing the cells in a suspended state, and positive for SSEA-3 and CD105.

(Ib-2(ii)) Induction of Differentiation from PSCs to EpiLCs

Basal media for differentiation induction include, but are not limited to, Neurobasal medium, Neural Progenitor Basal medium, NS-A medium, BME medium, BGJb medium, CMRL 1066 medium, minimal essential medium (MEM), Eagle MEM, αMEM, Dulbecco's modified Eagle medium (DMEM), Glasgow MEM, Improved MEM Zinc Option medium, IMDM medium, 199 medium, DMEM/F12 medium, Ham's medium, RPMI1640 medium, Fischer's medium, and mixtures thereof.

The medium can be a serum-containing or serum-free medium. Preferably, a serum-free medium can be used. The serum-free medium (SFM) refers to media with no unprocessed or unpurified serum and accordingly, can include media with purified blood-derived components or animal tissue-derived components (such as growth factors). The concentration of serum (for example, fetal bovine serum (FBS), human serum, etc.) can be 0-20%, preferably 0-5%, more preferably 0-2%, most preferably 0% (i.e., serum-free). The SFM may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thioglycerol, or equivalents thereto. The alternatives to serum can be prepared by the method disclosed in WO 98/30679, for example. Alternatively, any commercially available materials can be used for more convenience. The commercially available materials include Knockout™ Serum Replacement (KSR), Chemically-defined Lipid concentrated, and Glutamax (Invitrogen).

The medium can also contain other additives known per se. The additive is not subject to limitation, as long as EpiLCs equivalent to pre-gastrulating epiblast cells can be produced by the method of the present invention; for example, growth factors (for example, insulin and the like), polyamines (for example, putrescine and the like), minerals (for example, sodium selenate and the like), saccharides (for example, glucose and the like), organic acids (for example, pyruvic acid, lactic acid and the like), amino acids (for example, non-essential amino acids (NEAA), L-glutamine and the like), reducing agents (for example, 2-mercaptoethanol and the like), vitamins (for example, ascorbic acid, d-biotin and the like), steroids (for example, [beta]-estradiol, progesterone and the like), antibiotics (for example, streptomycin, penicillin, gentamycin and the like), buffering agents (for example, HEPES and the like), nutritive additives (for example, B27 supplement, N2 supplement, StemPro-Nutrient Supplement and the like) and the like can be mentioned. It is preferable that each of the additives be contained in a concentration range known per se.

In the method of producing EpiLCs of the present invention, pluripotent stem cells may be cultured in the presence or absence of feeder cells. The feeder cells are not subject to limitation, as long as EpiLCs can be produced by the method of the present invention; feeder cells known per se for use in culturing pluripotent stem cells such as ESCs and iPSCs can be used; for example, fibroblasts (mouse embryonic fibroblasts, mouse fibroblast cell line STO and the like) can be mentioned. The feeder cells are preferably inactivated by a method known per se, for example, radiation (gamma rays and the like), treatment with an anticancer agent (mitomycin C and the like) and the like. However, in a preferable embodiment of the present invention, pluripotent stem cells are cultured under feeder-free conditions.

The medium for inducing differentiation from pluripotent stem cells to EpiLCs (medium A) contains activin A as an essential additive in the basal medium. The activin A concentration is, for example, about 5 ng/ml or more, preferably about 10 ng/ml or more, more preferably about 15 ng/ml or more, and is, for example, about 40 ng/ml or less, preferably about 30 ng/ml or less, more preferably 25 ng/ml or less.

The medium A preferably further contains bFGF and/or KSR. Basic FGF and KSR remarkably increase the induction efficiency for EpiLCs when present in a range of effective concentrations. The bFGF concentration is, for example, about 5 ng/ml or more, preferably about 7.5 ng/ml or more, more preferably about 10 ng/ml or more, and is, for example, about 30 ng/ml or less, preferably about 20 ng/ml or less, more preferably about 15 ng/ml or less. The KSR concentration is, for example, about 0.1 w/w % or more, preferably about 0.3 w/w % or more, more preferably about 0.5 w/w % or more, and is, for example, about 5 w/w % or less, preferably about 3 w/w % or less, more preferably about 2 w/w % or less.

In a particularly preferred embodiment, the medium A contains activin A, bFGF and KSR in addition to the basal medium. Appropriate concentrations of these ingredients can be chosen over the range of about 10-30 ng/ml, preferably 15-25 ng/ml for activin A, about 7.5-20 ng/ml, preferably about 10-15 ng/ml for bFGF, and about 0.3-3 w/w %, preferably about 0.5-2 w/w % for KSR.

The activin A and bFGF contained in the medium A are not subject to limitation as to the source thereof, may be isolated and purified from cells of any mammals (for example, human, mouse, monkey, swine, rat, dog and the like). It is preferable to use activin A and bFGF homologous to the pluripotent stem cells subjected to the culture. The activin A and bFGF may also be chemically synthesized or biochemically synthesized using a cell-free translation system, or produced from a transformant bearing a nucleic acid encoding each of the proteins. The recombinant products of activin A and bFGF are commercially available.

A culture vessel used for inducing pluripotent stem cells into EpiLCs can include, but is particularly not limited to, flask, flask for tissue culture, dish, petri dish, dish for tissue culture, multi dish, micro plate, micro-well plate, multi plate, multi-well plate, micro slide, chamber slide, schale, tube, tray, culture bag, and roller bottle. The culture vessel can be cellular adhesive. The cellular adhesive culture vessel can be coated with any of substrates for cell adhesion such as extracellular matrix (ECM) to improve the adhesiveness of the vessel surface to the cells. The substrate for cell adhesion can be any material intended to attach pluripotent stem cells or feeder cells (if used). The substrate for cell adhesion includes collagen, gelatin, poly-L-lysine, poly-D-lysine, poly-L-orthinine, laminin, and fibronectin and mixtures thereof for example Matrigel, and lysed cell membrane preparations (Klimanskaya I et al 2005. *Lancet* 365: p 1636-1641).

In this cultivation, pluripotent stem cells are plated onto the culture vessel mentioned above to obtain a cell density of, for example, about $10^4$-$10^5$ cells/cm$^2$, preferably about 2 to $8 \times 10^4$ cells/cm$^2$, and cultured in an incubator under atmospheric conditions of 1-10% $CO_2$/99-90% air at about 30-40° C., preferably about 37° C., for less than 3 days, preferably about 2 days (e.g., 48±12 hours, preferably 48±6 hours). As a result of the culture, cells with flattened epiblast-like structure uniformly emerge.

The fact of differentiation into EpiLCs can be confirmed by, for example, analyzing the expression levels of EPiLC- and/or pluripotent stem cell-marker genes using RT-PCR. As mentioned above, EpiLC is defined as a cell with (1) elevated gene expression of at least one selected from Fgf5, Wnt3 and Dnmt3b compared to the PSC before inducing differentiation and (2) reduced gene expression of at least one selected from Gata4, Gata6, Sox17 and Blimp1 compared to the PSC before inducing differentiation. Therefore, the fact of differentiation into EpiLCs can be confirmed by determining the expression levels of at least one selected from Fgf5, Wnt3 and Dnmt3b and/or at least one selected from Gata4, Gata6, Sox17 and Blimp1 in the cells obtained by the culture, and comparing the expression levels with those in the pluripotent stem cells before inducing differentiation.

(Ic) Induction of Differentiation from Epiblasts or EpiLCs to PGCLCs

By allowing thus-obtained epiblasts or EpiLCs to express certain exogenously introduced TF(s) that show specific expression in PGCs, it is possible to induce the epiblasts or EpiLCs into PGC-like cells (PGCLCs) without cytokines including BMP4.

The combinations of TF(s) capable of inducing the epiblasts or EpiLCs into PGLCs include the following (i) to (v):
(i) Blimp1, Prdm14 and Tfap2c;
(ii) Blimp1 and Prdm14;
(iii) Blimp1 and Tfap2c;
(iv) Prdm14 and Tfap2c; and
(v) Prdm14.

Hereinafter these TFs are also referred to as "the PGCLC inducer of the present invention". The PGCLC inducer of the present invention may be introduced in a form of protein or nucleic acid encoding same into an epiblast or EpiLC.

As the PGCLC inducer of the present invention, for example, a Blimp1, Prdm14 or Tfap2c protein derived from any mammal (e.g., human, mouse, rat, monkey, bovine, horse, swine, dog etc.) or a nucleic acid encoding the same and the like can be used. A species of the same derivation as the target epiblast or EpiLC is preferable.

Examples of the Blimp1 to be used in the present invention include human B-lymphocyte-induced maturation protein 1 (BLIMP1) consisting of the amino acid sequence shown by SEQ ID NO: 2 (registered as NCBI accession number: NP_001189.2), mouse Blimp1 consisting of the amino acid sequence shown by SEQ ID NO: 4 (registered as NCBI accession number: NP_031574.1), and an ortholog thereof in other mammal (see GeneCards® human gene database), a polymorphic variant thereof (e.g., G74S (db-SNP No.: rs2185379), D203E (dbSNP No.: rs811925), a splicing variant thereof (e.g., O75626-2, O75626-3; see UniProtKB/Swiss-Prot database) and the like. Alternatively, it may be a protein having an amino acid identity of not less than 90%, preferably not less than 95%, more preferably not less than 97%, even more preferably not less than 98%, most preferably not less than 99%, with any of the above-mentioned proteins, and having a function equivalent to that of said protein (e.g., transcription activation of PGC-specific promoter and the like). The identity of the amino acid sequence as mentioned herein can be calculated using the blastp program of the NCBI BLAST (National Center for Biotechnology Information Basic Local Alignment Search Tool) under the following conditions (expectancy=10; gap allowed; matrix=BLOSUM62; filtering=OFF).

Examples of Prdm14 to be used in the present invention include human PR domain containing 14 (PRDM14) consisting of the amino acid sequence shown by SEQ ID NO: 6 (registered as NCBI accession number: NP_078780.1), mouse Prdm14 consisting of the amino acid sequence shown by SEQ ID NO: 8 (registered as NCBI accession number: NP_001074678.1), and an ortholog thereof in other mammal (see GeneCards® human gene database), a polymorphic variant thereof, a splicing variant thereof and the like. Alternatively, it may be a protein having an amino acid identity m of not less than 90%, preferably not less than 95%, more preferably not less than 97%, even more preferably not less than 98%, most preferably not less than 99%, with any of the above-mentioned proteins, and having a function equivalent to that of said protein (e.g., transcription activation of PGC-specific promoter and the like). Here, the identity of the amino acid sequence can be calculated in the same manner as in the above.

Examples of Tfap2c to be used in the present invention include human transcription factor AP-2 gamma (TFAP2C) consisting of the amino acid sequence shown by SEQ ID NO: 10 (registered as NCBI accession number: NP_003213.1), mouse Tfap2c consisting of the amino acid sequence shown by SEQ ID NO: 12 (registered as NCBI accession number: NP_033361.1), and an ortholog thereof in other mammal (see GeneCards® human gene database), a polymorphic variant thereof (e.g., K244E; see *Genome Res.* 14:2121-2127(2004)), a splicing variant thereof and the like. Alternatively, it may be a protein having an amino acid identity of not less than 90%, preferably not less than 95%, more preferably not less than 97%, even more preferably not less than 98%, most preferably not less than 99%, with any of the above-mentioned proteins, and having a function equivalent to that of said protein (e.g., transcription activation of PGC-specific promoter and the like). Here, the identity of the amino acid sequence can be calculated in the same manner as in the above.

Blimp1, Prdm14 or Tfap2c may be a fusion protein of any of the above-mentioned proteins and a cell penetrating peptide (e.g., TAT derived from HIV and polyarginine).

Examples of the nucleic acid encoding Blimp1 include human B-lymphocyte-induced maturation protein 1 (BLIMP1) cDNA consisting of the nucleotide sequence shown by SEQ ID NO: 1 (registered as NCBI accession number: NM_001198.3), mouse Blimp1 cDNA consisting of the nucleotide sequence shown by SEQ ID NO: 3 (registered as NCBI accession number: NM_007548.2), and an ortholog thereof in other mammal, a transcription variant thereof, a splicing variant thereof and the like. Alternatively, it may be a nucleic acid encoding a protein having a nucleotide identity of not less than 90%, preferably not less than 95%, more preferably not less than 97%, even more preferably not less than 98%, most preferably not less than 99%, with any of the above-mentioned nucleic acids, and having a function equivalent to that of a protein encoded by said nucleic acid (e.g., transcription activation of PGC-specific promoter and the like). The identity of the nucleotide sequence as mentioned herein can be calculated using the blastn program of the NCBI BLAST (National Center for Biotechnology Information Basic Local Alignment Search Tool) under the following conditions (expectancy=10; gap allowed; filtering-ON; match score=1; mismatch score=-3). Alternatively, it may have a plus strand in a complementary relationship of the level permitting hybridization with the complementary strand of any of the above-mentioned nucleic acids under stringent conditions. The stringent conditions herein can be determined based on the melting temperature (Tm) of the nucleic acid binding to a complex or probe, as taught in Berger and Kimmel (1987, Guide to Molecular Cloning Techniques Methods in Enzymology, Vol. 152, Academic Press, San Diego Calif.). For example, wash conditions after hybridization generally include about "1×SSC, 0.1% SDS, 37° C.". The complementary strand is preferably one that maintains hybridization state with the target plus strand even when washed under such conditions. Although not particularly limited, more stringent hybridization conditions include wash conditions of about "0.5×SSC, 0.1% SDS, 42° C.", more stringent wash conditions of about "0.1×SSC, 0.1% SDS, 65° C.", which permit the plus strand and the complementary strand to maintain hybridization state even after washing.

Examples of the nucleic acid encoding Prdm14 include human PR domain containing 14 (PRDM14) cDNA consisting of the nucleotide sequence shown by SEQ ID NO: 5 (registered as NCBI accession number: NM_024504), mouse Prdm14 cDNA consisting of the nucleotide sequence shown by SEQ ID NO: 7 (registered as NCBI accession number: NM_001081209), and an ortholog thereof in other mammal, a transcription variant thereof, a splicing variant thereof and the like. Alternatively, it may be a nucleic acid encoding a protein having a nucleotide identity of not less than 90%, preferably not less than 95%, more preferably not less than 97%, even more preferably not less than 98%, most preferably not less than 99%, with any of the above-mentioned nucleic acids, and having a function equivalent to that of a protein encoded by said nucleic acid (e.g., transcription activation of PGC-specific promoter and the like). The identity of the nucleotide sequence as mentioned herein can be calculated in the same manner as mentioned above. Alternatively, it may have a plus strand in a complementary relationship of the level permitting hybridization with the complementary strand of any of the above-mentioned nucleic acids under stringent conditions. The stringent conditions as mentioned herein are as defined above.

Examples of the nucleic acid encoding Tfap2C include human transcription factor AP-2 gamma (TFAP2C) cDNA consisting of the nucleotide sequence shown by SEQ ID NO: 9 (registered as NCBI accession number: NM_003222), mouse Tfap2C cDNA consisting of the nucleotide sequence shown by SEQ ID NO: 11 (registered as NCBI accession number: NM_009335), and an ortholog thereof in other mammal, a transcription variant thereof, a splicing variant thereof and the like. Alternatively, it may be a nucleic acid encoding a protein having a nucleotide identity of not less than 90%, preferably not less than 95%, more preferably not less than 97%, even more preferably not less than 98%, most preferably not less than 99%, with any of the above-mentioned nucleic acids, and having a function equivalent to that of a protein encoded by said nucleic acid (e.g., transcription activation of PGC-specific promoter and the like). The identity of the nucleotide sequence as mentioned herein can be calculated in the same manner as mentioned above. Alternatively, it may have a plus strand in a complementary relationship of the level permitting hybridization with the complementary strand of any of the above-mentioned nucleic acids under stringent conditions. The stringent conditions as mentioned herein are as defined above.

The nucleic acid encoding Blimp1, Prdm14 or Tfap2c may be DNA, RNA or DNA/RNA chimera. In addition, the nucleic acid may be a single strand, double stranded DNA, double stranded RNA or DNA:RNA hybrid. Preferred is a double stranded DNA or single stranded RNA. As said RNA, RNA incorporating 5-methylcytidine and pseudouridine (TriLink Biotechnologies), or a modified RNA obtained by a phosphatase treatment may be used for the suppression of degradation.

Blimp1, Prdm14 and Tfap2c, and nucleic acids encoding them can be obtained by easily isolating a nucleic acid encoding each protein or, where necessary, producing a recombinant protein or chemically synthesizing the same based on, for example, the cDNA sequence information of the above-mentioned human or mouse Blimp1, Prdm14 and Tfap2c.

While the method of expressing a PGCLC inducer of the present invention in an epiblast or EpiLC is not particularly limited, for example, the following method can be used. Here, "expression" means that, when the PGCLC inducer is nucleic acid encoding Blimp1, Prdm14 or Tfap2c, a Blimp1, Prdm14 or Tfap2c protein is produced by intracellular (transcription and) translation from the nucleic acid, and when the PGCLC inducer is a Blimp1, Prdm14 or Tfap2c protein, it means the same as an intracellular introduction of the protein.

When the aforementioned PGCLC inducer is in the form of a DNA, for example, a vector such as virus, plasmid, artificial chromosome and the like may be introduced into an epiblast or EpiLC by a method such as lipofection, liposome, microinjection and the like. Examples of the viral vector include retroviral vector, lentiviral vector, adenoviral vector, adeno-associated viral vector, Sendai viral vector and the like. Examples of the artificial chromosome vector include human artificial chromosome (HAC), yeast artificial chromosome (YAC), bacterial artificial chromosome (BAC, PAC) and the like. Examples of the plasmid include plasmids for mammalian cells. The vector can contain regulatory sequences of promoter, enhancer, ribosome binding sequence, terminator, polyadenylation site and the like so that a DNA encoding Blimp1, Prdm14 or Tfap2c can be expressed and further, where necessary, selectable marker sequences such as a drug resistance gene (for example, kanamycin resistance gene, ampicillin resistance gene, puromycin resistance gene and the like), thymidine kinase gene, diphtheria toxin gene and the like, a reporter gene sequence such as fluorescent protein, β-glucuronidase (GUS), FLAG and the like, and the like. As a promoter, SV40 promoter, LTR promoter, CMV (cytomegalovirus) promoter, RSV (Rous sarcoma virus) promoter, MoMuLV (Moloney mouse leukemia virus) LTR, HSV-TK (herpes simplex virus thymidine kinase) promoter, EF-α promoter, CAG promoter and TRE promoter (minimal CMV promoter having a Tet response element with continuous 7 tetO sequences). When a TRE promoter is used, a fusion protein of tetR and VP16AD or a fusion protein of reverse tetR (rtetR) and VP16AD is desirably expressed simultaneously in the same cell. Here, a vector having a TRE promoter and capable of expressing a fusion protein of reverse tetR (rtetR) and VP16AD is referred to as a drug responsive inducible vector. In addition, to introduce an expression cassette comprising a promoter and a DNA encoding Blimp1, Prdm14 or Tfap2c operably linked thereto into a chromosome of an epiblast or EpiLC and cut it out as necessary therefrom, the above-mentioned vector may have a transposon sequence before and after the expression cassette. While the transposon sequence is not particularly limited, piggyBac can be mentioned. In another embodiment, it may have a LoxP sequence before and after the expression cassette to remove the expression cassette.

When the aforementioned PGCLC inducer is in the form of an RNA, it may be introduced into an epiblast or EpiLC by a method such as electroporation, lipofection, microinjection and the like. When the PGCLC inducer is in the form of a protein, it may be introduced into an epiblast or EpiLC by a method such as lipofection, fusion with cell penetrating peptide (e.g., TAT derived from HIV and polyarginine), microinjection and the like.

An exogenous PGCLC inducer may be expressed in an epiblast or EpiLC at least within 3 days from the start of the culture of the epiblast or EpiLC for PGCLC induction (i.e., culture in the absence of cytokines including BMP4), desirably within 1 day from the start of the culture, more desirably immediately after the start of the culture. When a PGCLC inducer is expressed after 3 days from the start of the culture for PGCLC induction, the PGCLC induction efficiency may decrease. While the period when the expression of an exogenous PGCLC inducer is maintained is not particularly limited, it is desirably not less than 1 day and preferably not more than 10 days (e.g., 1, 2, 3, 4, 5, 6, 7, 8, 9 or 10 days), more preferably 1 to 6 days, even more preferably 1 to 5 days, most preferably 2 to 4 days (e.g., 2, 3 or 4 days). While the method of maintaining the expression is not particularly limited, when the PGCLC inducer is a non-integrated and non-episomally replicable molecule such as plasmid, RNA or protein, the introduction can be performed plural times during a desired period (for example, once every 2 days for plasmid introduction, once everyday for RNA or protein direct introduction). In another embodiment, a PGCLC inducer in the form of DNA (e.g., viral or non-viral vectors) may be introduced into an epiblast or EpiLC in a form capable of being conditionally expressed in the cell. For example, when a drug (Tet)-responsive inducible vector is used, a method of maintaining expression by addition of tetracycline of a derivative thereof such as doxycycline to the medium during a desired period; when a vector having a transposon sequence is used, a method including, after lapse of a desired period, introducing transposase to remove the PGCLC inducer from the cell; and when a vector having LoxP sequences are used, a method including, after lapse of a desired period, introducing Cre recombinase to remove the PGCLC inducer from the cell and the like can be recited as examples. Instead of Tet-responsive inducible vector, other inducible vectors known in the art, such as a vector containing metallothionein promoter, may also be used.

When a PGCLC inducer in the form of DNA is introduced into an epiblast or EpiLC in a form capable of being conditionally expressed, the PGCLC inducer may also be introduced into the epiblast or EpiLC prior to the induction of the epiblast or EpiLC. For example, the PGCLC inducer can be introduced into a PSC before inducing differentiation into EpiLC. When the PSC as the starting material for EpiLC induction is an iPS cell, the PGCLC inducer can also be co-introduced into a somatic cell with reprogramming factors. Alternatively, when the PGCLC of interest is a non-human animal cell such as mouse, an epiblast can be isolated from an embryo of transgenic animal having the PGLC inducer in a form capable of being conditionally expressed in the epiblast. Likewise, a non-human animal PSC can be prepared from an appropriate cell source derived from the transgenic animal.

In view of clinical application to human therapy, it is preferable that the PGCLC inducer is not integrated into the genome of the epiblast or EpiLc nor stably maintained outside chromosome in order to avoid a risk of tumorigenesis. Therefore, in a preferable embodiment, the PGCLC inducer is in a form capable of disappearing from the PGCLC generated rapidly. As the PGCLC inducer for this purpose, a plasmid, RNA or protein may be exemplified. When the PGCLC inducer is in the form of DNA, non-integrated vector such as plasmid, adenoviral vector, Sendai viral vector, episomal vector may be used preferably. Since Sendai viral vector or episomal vector may be maintained outside chromosome for a relatively long period, it is more preferable to use a Sendai viral vector removable from PGCLC by siRNA or an episomal vector removable from PGCLC by Cre-loxP system. Alternatively, when the PGCLC inducer is introduced into an epiblast or EpiLC in a form of integrated vector such as retroviral vector, lentiviral vector and transposon, the vector is preferably designed such that it may be removed from chromosome of the PGCLC generated by Cre-loxP system of transposases.

The culture of epiblasts or EpiLCs into which the PGCLC inducer has been introduced for PGCLC induction may be performed as described in WO 2012/020687, Cell 146, 519-532 (2011) or *Science* 338, 971-975 (2012) except not adding cytokines including at least BMP4 in an amount effective for inducing epiblasts or EpiLCs into a PGC state (i.e., less than 100 ng/ml, preferably less than 50 ng/ml, more preferably less than 10 ng/ml). Most preferably, the medium lacks a detectable amount of BMP4.

As the basal medium for PGCLC induction, the basal media exemplified for the use in the EpiLC induction mentioned above (see Ib-2(ii)) are likewise preferably used. The medium may contain the same additives as those exemplified for the use in the EpiLC induction, as long as PGCLCs capable of contributing to normal spermatogenesis can be produced without going through transient mesodermal program by the method of the present invention.

The medium can be a serum-containing or serum-free medium (SFM). Preferably, a serum-free medium can be used. The concentration of serum (for example, fetal bovine serum (FBS), human serum, etc.) can be 0-20%, preferably 0-5%, more preferably 0-2%, most preferably 0% (i.e., serum-free). The SFM may contain or may not contain any alternatives to serum such as KSR.

The medium for PGCLC induction of the present invention can contain cytokines other than BMP4, including LIF, SCF, BMP8b and EGF, as long as PGCLCs capable of contributing to normal spermatogenesis can be produced without going through transient mesodermal program by the method of the present invention. Preferably, the medium contains no or a low amount of LIF (e.g., less than 300 U/ml, more preferably less than 100 U/ml). More preferably, the medium further contains no or low amounts of SCF and/or BMP8b and/or EGF (e.g., less than 30 ng/ml, more preferably less than 10 ng/ml for SCF; less than 100 ng/ml, more preferably less than 50 ng/ml for BMP8b; less than 10 ng/ml, more preferably less than 5 ng/ml for EGF). Most preferably, the medium lacks detectable amounts of BMP4, LIF, SCF, BMP8b and EGF.

In PGCLC induction culture of the present invention, epiblasts or EpiLCs are seeded to a cellular non-adhesive or low-adhesive culture vessel known per se to obtain a cell density of, for example, about 3 to $10 \times 10^4$ cells/mL, preferably about 4 to $8 \times 10^4$ cells/mL, and cultured in an incubator in an atmosphere of 1-10% $CO_2$/99-90% air at about 30-40° C., preferably about 37° C., for a period for expressing the introduced PGC inducer, for example, 1 to 10 days, preferably 1 to 6 days, more preferably 1 to 5 days, most preferably 2 to 4 days (e.g., 2, 3 or 4 days).

The fact of differentiation into PGCLCs can be confirmed by, for example, analyzing the expression of Blimp1 by RT-PCR and the like. As required, furthermore, the expression of other genes and cell surface antigens can also be examined. Examples of other genes include Stella. When epiblasts or EpiLCs (or embryos or PSCs as source thereof) bearing genes encoding fluorescent proteins under the control of Blimp1- and/or Stella-promoters are used as a starting material, the fact of differentiation into PGCLCs can be confirmed by FACS analysis. When the starting cells bear no appropriate transgenic reporter, such as ESCs or iPSCs derived from human, it is preferable to confirm the fact of differentiation into PGCLCs by FACS analysis and the like using one or more cell surface antigens specifically expressed on PGCLCs. As the cell surface antigens, preferably SSEA-1 and integrin-$\beta$3 are exemplified.

The method of producing PGCLCs from epiblasts isolated from embryos or EpiLCs induced from PSCs such as ES cells and iPS cells of the present invention is characterized in that it bypasses a mesodermal program that accompanies PGC specification in vivo and in vitro by cytokines including BMP4. As a result, according to the method of the present invention, PGCLCs can be obtained for a shorter period than that in the case using the cytokines. Importantly, the PGCLCs obtained by the method of the present invention robustly contribute to spermatogenesis and fertile offspring equal to or greater than the cytokine-induced PGCLCs, in spite of not going through a mesodermal program different from the PGC specification in vivo.

(II) Kit for Production of PGCLC from EpiLC

In another aspect, the present invention provides a kit for production of a PGCLC from an EpiLC. The kit can contain the aforementioned PGCLC inducer of the present invention, i.e., a PGCLC cell inducer containing the following TF(s):
(i) Blimp1, Prdm14 and Tfap2c;
(ii) Blimp1 and Prdm14;
(iii) Blimp1 and Tfap2c;
(iv) Prdm14 and Tfap2c;
(v) Prdm14; or
nucleic acid(s) encoding any of the TF(s) or (i) to (v) above (e.g., alcohol precipitate, frozen TE solution, lyophilizate and the like of a nucleic acid; lyophilizate of a protein, a frozen liquid dissolved in a suitable buffer, and the like), and the above-mentioned vector, cells, reagent and culture medium for introduction of said factor. This kit may further contain a protocol or instructions describing the step of induction into PGCLC.

In a preferable embodiment, the kit for production of a PGCLC from an epiblast or EpiLC of the present invention contains an isolated epiblast or EpiLC comprising nucleic acid(s) encoding exogenous transcription factor(s) selected from the group consisting of:
(i) Blimp1, Prdm14 and Tfap2c;
(ii) Blimp1 and Prdm14;
(iii) Blimp1 and Tfap2c;
(iv) Prdm14 and Tfap2c; and
(v) Prdm14;
wherein the nucleic acid(s) is/are in a form capable of being conditionally expressed in the epiblast or EpiLC. The kit can further contain a reagent for inducing the expression of the PGCLC inducer. As said reagent, doxycycline (Dox) for Tet-responsive inducible vectors, metal ion for vectors under the control of a metallothionein promoter may be exemplified.

In another preferable embodiment, the kit for production of a PGCLC from a PSC of the present invention contains an isolated PSC comprising nucleic acid(s) encoding exogenous transcription factor(s) selected from the group consisting of:

(i) Blimp1, Prdm14 and Tfap2c;
(ii) Blimp1 and Prdm14;
(iii) Blimp1 and Tfap2c;
(iv) Prdm14 and Tfap2c; and
(v) Prdm14;
wherein the nucleic acid(s) is/are in a form capable of being conditionally expressed in an EpiLC differentiated from the PSC. The kit can further contain a reagent for inducing the PSC into an EpiLC comprising ActA and optionally bFGF and/or KSR; and the above-mentioned reagent for inducing the expression of the PGCLC inducer.

In this context, the present invention also provides a method of producing a PGCLC from a PSC, which comprises the following steps I) and II):
I) the step for producing an EpiLC by culturing a PSC in the presence of ActA, optionally in the presence of further bFGF and/or KSR;
II) the step for inducing the EpiLC obtained in the step I) into a PGCLC by any of the methods described above. The method can further comprise the step III):
III) the step for selecting a Blimp1-positive cell from the cells obtained in the step II). As selection markers for FACS, surface antigens specific to PGCLC, SSEA-1, integrin-$\beta$3 and the like may also be used.

(III) Cell Population Containing PGCLCs Derived from Epiblasts or EpiLCs

The present invention also provides a cell population containing PGCLCs derived from epiblasts isolated from embryos or EpiLCs induced from PSCs, produced by the foregoing steps. The cell population may be a purified population of PGCLCs, and 1 kind or more of cells other than PGCLCs may be co-present. Here, "PGC-like cell (PGCLC)" is defined as a cell that shows elevated expression of Blimp1 and/or Stella compared to the EpiLC before inducing differentiation, is capable of contributing to normal spermatogenesis, and does not form teratoma when transplanted into an immunodeficient mouse. As stated above, when PGCLCs are induced using embryos or PSCs bearing genes encoding fluorescent proteins under the control of Blimp1- and/or Stella-promoters as a starting material, the Blimp1- and/or Stella-positive PGCLCs can be easily isolated and purified by sorting out the cell population obtained in the foregoing step using a cell sorter. The PGCLCs can also be isolated and purified by FACS using a reporter under the control of gene whose expression increases along with Blimp1 and Stella (e.g., Nanog) as a marker.

(IV) Use of PGCLCs Derived from Puluripotent Stem Cells

The PGCLCs derived from epiblasts isolated from embryos or EpiLCs induced from PSCs of the present invention can be used for varied purposes. For example, since the PGCLCs transplanted into a testis of a recipient animal can robustly contribute to spermatogenesis in the testis and the generation of healthy offspring, they can be used for the treatment of infertility or hereditary diseases of reproductive tissues.

The transplantation of the PGCLCs into a testis can be performed by using the PGCLCs in the same manner as described in WO 2012/020687 or Cell 146, 519-532 (2011).

The PGCLCs of the present invention can also be used for oogenesis (see Science 338, 971-975 (2012)).

The PGCLCs (including a cell population containing PGCLCs; the same applies below) of the present invention are produced as a parenteral preparation, preferably as an injection, suspension, or drip infusion, in a mixture with a pharmaceutically acceptable carrier, by a conventional means. Examples of the pharmaceutically acceptable carrier that can be contained in the parenteral preparation include aqueous liquids for injection, such as physiological saline and isotonic solutions containing glucose and other auxiliary drugs (e.g., D-sorbitol, D-mannitol, sodium chloride and the like). The agent of the present invention may be formulated with, for example, a buffering agent (e.g., phosphate buffer solution, sodium acetate buffer solution), a soothing agent (e.g., benzalkonium chloride, procaine hydrochloride and the like), a stabilizer (e.g., human serum albumin, polyethylene glycol and the like), a preservative, an anti-oxidant and the like.

When the agent of the present invention is prepared as an aqueous suspension, PGCLCs are suspended in one of the aforementioned aqueous liquids to obtain a cell density of about $1.0 \times 10^6$ to about $1.0 \times 10^7$ cells/ml.

The agent of the present invention can be cryopreserved under conditions typically used for the cryopreservation of stem cells, and thawed immediately before use.

Because the preparation thus obtained is stable and less toxic, it can be safely administered to mammals such as humans. Although the method of administration is not particularly limited, the preparation is preferably administered by injection or drip infusion into a seminiferous tube when used for spermatogenesis. For a male infertility patient, for example, it is usually convenient to administer the agent in an amount of about $1.0 \times 10^5$ to about $1 \times 10^7$ cells, based on the amount of PGCLCs per dose, once or 2-10 times at about 1- to 2-week intervals. The present invention is hereinafter described in further detail by means of the following examples, to which, however, the invention is never limited.

EXAMPLES

Methods

1. Animals

All animal experiments were conducted according to the Guidelines for Animal Experiments of Kyoto University. The BVSC transgenic mice (C57BL/6 background, Acc. No. BV, CDB0460T; SC CDB0465T: www.cdb.riken.jp/arg/TG%20mutant%20mice%20list.html) were established as reported previously (Reproduction 136, 503-514 (2008)). B6;129-Gt(ROSA)26Sor$^{tm1(rtTA*M2)Jae}$Col1a1$^{tm2(tetO-Pou5f1)Jae}$/J mice (Cell 121, 465-477 (2005)) (stock number: 006911) were purchased from the Jackson Laboratory. WBB6F1-W/W$^v$ mice were purchased from SLC (Shizuoka, Japan).

2. Establishment of ESCs

Mice homozygous for the Rosa26-rtTA knock-in allele were obtained by crossing B6; 129-Gt(ROSA) 26Sor$^{tm1(rtTA*M2)Jae}$Col1a1$^{tm2(tetO-Pou5f1)Jae}$/J mice heterozygous for both loci. They were mated with BVSC transgenic mice and blastocysts were recovered at embryonic day (E) 2.5. BVSC-R26rtTA ESCs were selected by PCR genotyping, established and maintained under the N2B27 "2i+LIF" condition (Nature 453, 519-523 (2008)). A male cell line was used in this study.

3. Chimera Formation Assay

BVSC-R26rtTA ESCs were trypsinized and a single cell suspension was prepared. Approximately 15 ESCs/embryo were injected into blastocoels of E3.5 blastocysts obtained from ICR (albino) female mice with a piezo-actuating micromanipulator. Injected embryos were transferred into uteri of E2.5 pseudopregnant ICR female mice. Chimeric mice were delivered by Caesarean section at E18.5. Chimerism was determined by coat-colour. They were subjected to test breeding with ICR female mice to confirm the germline contribution.

4. Vector Construction

The mouse Blimp1 coding sequence (CDS) (from ATG in exon 3) and Tfap2c variant 1 (Accession number: NM_009335.2) CDS were cloned by PCR flanked with SalI-AviTag-XhoI and NotI sites and NotI and EcoRI sites, respectively. The Prdm14 CDS was obtained from AG-P14 (*Cell Stem Cell* 12, doi: 10.1016/j.stem.2012.12.012 (2013)).

The SalI-Kosak-Avi-Blimp1-NotI cassette was subcloned into XhoI/NotI sites of the pPyCAG-cHA-IP plasmid (*Mol Cell Biol* 22, 1526-1536 (2002)), and this cassette was subcloned again into the EcoRI/NotI sites of the pENTR1A Dual Selection Vector (Invitrogen). For Prdm14 and Tfap2c, KpnI-Kosak-3×FLAG-XhoI-G4S_Linker-SpeI and BamEI-Kosak-V5-G4S_Linker-NotI fragments, respectively, were attached to the N termini by PCR or synthesized oligonucleotide linker ligation. 3×FLAG-Prdm14 and V5-Tfap2c cassettes were subcloned into the KpnI/NotI and BamHI/EcoRI sites of pENTR1A, respectively. Lastly, they were shuttled into the PB-TET destination vector (Addgene) (*Nature* 458, 766-770 (2009)) with LR clonase II Enzyme Mix (Invitrogen). To construct pPBCAG-hph, a CAG promoter fragment from pCAGGS plasmid obtained by digestion of SpeI and EcoRI (filled) was inserted into the GG131 vector (*Development* 137, 3185-3192 (2010); *Gene* 108, 193-199 (1991)) digested with SpeI/MscI. All sequences engineered by PCR or oligonucleotide synthesis were confirmed. All attached sequences are shown in Table 1 and primer sequences for cloning are listed in Table 2.

TABLE 1

```
SalI-Kosak-AviTag-XhoI-(Blimp1 Exon3 ATG)
GTCGACGCCACCATGTCCGGCCTGAACGACATCTTCGGCGCTCAGAAAAT
CGAATGGCACGAACTCGAG-ATG) (SEQ ID NO: 13)

KpnI-Kosak-3xFLAG-XhoI-G4S_Linker-SpeI-
(Prdm14 ATG)
GGTACCGCCACCATGGACTACAAGGACCACGACGGAGATTATAAGGATCA
CGATATCGACTATAAGGATGACGACGATAAGCTCGAGTCTGGTGGCGGTG
GCTCGGGCGGAGGTGGGTCGGGTGGCGGCGGATCAACTAGT-(ATG)
(SEQ ID NO: 14)

BamHI-Kosak-V5-G4S_Linker-NotI-(Tfap2c ATG)
GGATCCGCCACCATGGGCAAGCCCATCCCTAACCCTCTGCTGGGCCTGGA
CAGCACCTCTGGTGGCGGTGGCTCGGGCGGAGGTGGGTCGGGTGGCGGCG
GATCAAGCGGCCGC-(ATG) (SEQ ID NO: 15)
```

TABLE 2

| | |
|---|---|
| SalI-Kosak+A11+A2:B19+ A2:C21+A2:819 | GCGGTCGACGCCACCATGTCCGGCC TGAACGACATCTTCGGCGCTCAGAA AATCGAATGGCACGAACTCGAGATG AAAATGGACATG (SEQ ID NO: 16) |
| Blimp1-2568TAG-NotI_R2 | GCGGGGCCGCCTAAGGATCCATCGG TTCAACTGTC (SEQ ID NO: 17) |
| NotI_Tcfap2c_var1_F | AAAGCGGCCGCATGTTGTGGAAAAT AAC (SEQ ID NO: 18) |

TABLE 2 -continued

| | |
|---|---|
| Tfap2c_var1_EcoRI_R | ATAGAATTCTTACTTCCTGTGCTTTT (SEQ ID NO: 19) |
| Avi-Blimp1_qF1 | TGGTGCCTGTAAAGGTCAAAC (SEQ ID NO: 20) |
| Avi-Blimp1_AttB2_qR1 | GGCGGAATTAGCTTATCGAC (SEQ ID NO: 21) |
| 3xFLAG-Prdm14_qF1 | TCCTGGATCAAGAGGCTTTC (SEQ ID NO: 22) |
| 3xFLAG-Prdm14_AttB2_qR2 | ACTAGCTAGAGCGGCCATCAC (SEQ ID NO: 23) |
| V5-Tfap2c_qF1 | ATTCCAGCAAGACGATGGAG (SEQ ID NO: 24) |
| V5-Tfap2c_AttB2_qR1 | GGCGGAATTAGCTTATCGAC (SEQ ID NO: 25) |
| b-geo_qF1 | GCTTGCCGAATATCATGGTG (SEQ ID NO: 26) |
| b-geo_qR1 | CTTCAGCAATATCACGGGTAGC (SEQ ID NO: 27) |
| Blimp1_CDS_qF1 | GCCCACCTGCAGAAACACTAC (SEQ ID NO: 28) |
| Blimp1_CDS_qR1 | CCAGAATGCAATCGAAGGTG (SEQ ID NO: 29) |
| Prdm14_CDS_qF1 | CTTCCAGCCTGAACAAGCAC (SEQ ID NO: 30) |
| Prdm14_CDS_qR1 | GGAGTATGCTGGAGGCAGTG (SEQ ID NO: 31) |
| Tfap2c_CDS_qF1 | CCACGCGGAAGAGTATGTTG (SEQ ID NO: 32) |
| Tfap2c_CDS_qR1 | GTTGTTCCCGTTGGGTGTC (SEQ ID NO: 33) |

5. Transfection and Selection of Subclones

BVSC-R26rtTA ESCs were transfected with PB-TET vectors containing key factors, pPBCAG-hph, and pCA-GGS-mPB using Lipofectamine2000 (Invitrogen) on feeder cells (mouse embryonic fibroblasts) in a 60 mm dish under a "2i+LIF" condition. The total amount of vector DNA was below 8 μg. Transfectants were selected with Hygromycin B (150 μg/ml) (Sigma) and genotyped with PCR for transgenes. The primer sequences for the genotype are shown in Table 3.

TABLE 3

| Genotype | |
|---|---|
| Avi-Blimp1_F3 | AAATCGAATGGCACGAACTC (SEQ ID NO: 34) |
| Avi-Blimp1_R2 | GCATCCAGTTGCTTTTCTCC (SEQ ID NO: 35) |
| 3xFLAG-Prdm14_F2 | ATCGACTATAAGGATGACGAC (SEQ ID NO: 36) |
| 3xFLAG-Prdm14_R1 | GAGGTTCCTAAAGTGACTGTAG (SEQ ID NO: 37) |
| V5-Tfap2c_F1 | ATGGGCAAGCCCATCCCTAACCCT (SEQ ID NO: 38) |
| V5-Tfap2c_R3 | AAGGAGGCGGCTGGTACTCTGCAAC (SEQ ID NO: 39) |
| Blimp1-mVenus_F | ACTCATCTCAGAAGAGGATCTG (SEQ ID NO: 40) |
| Blimp1-mVenus_R | CACAGTCGAGGCTGATCTCG (SEQ ID NO: 41) |
| Stella-ECFP_F | CGAGCTAGCTTTTGAGGCTT (SEQ ID NO: 42) |

TABLE 3 -continued

| Genotype | |
|---|---|
| Stella-ECFP_R | AACTTGTGGCCGTTTACGTC (SEQ ID NO: 43) |
| Rosa-rtTA | |
| o1MR8545_F | AAAGTCGCTCTGAGTTGTTAT (SEQ ID NO: 44) |
| o1MR8546_R | GGAGCGGGAGAAATGGATATG (SEQ ID NO: 45) |
| o1MR8052_R | GCGAAGAGTTTGTCCTCAACC (SEQ ID NO: 46) |

6. Southern Blotting

Eight micrograms of genomic DNA was isolated and digested with BamHI. DNA fragments were electrophoresed in 0.7% agarose gel, transferred to Hybond N+ (GE healthcare) and UV-crosslinked. The β-geo probe was obtained by digestion of PB-TET with RsrII/SmaI, labeled with $^{32}$P (PerkinElmer) by a Random Primer DNA Labeling Kit Ver. 2.0 (TaKaRa) and purified with an Illustra ProbeQuant spin column (GE Healthcare). Radioisotope images were captured with a BAS system (Fujifilm).

7. TF- and Ck-PGCLCs

Transfected ESCs were adapted to a feeder-free condition prior to induction. EpiLC differentiation was performed as reported previously (*Cell* 146, 519-532 (2011)). After 36 hrs of differentiation, cells were harvested and cultured in a Lipidure-Coat 96-well plate (NOF) to be aggregated (started with 2,000 cells/well) in GK15 with 1.5 μg/ml of Dox (Clonetech). PGCLCs were induced by BMP4 (500 ng/ml), BMP8A (500 ng/ml), SCF (100 ng/ml), LIF (1000 U/ml) and EGF (50 ng/ml) as previously described (*Cell* 146, 519-532 (2011)). LDN193189 (120 pM; Stemgent) was added concurrently with Dox or Cks. Aggregates from ground-state ESCs were also cultured in GK15 with Dox as described above.

8. Reverse Transcription (RT) and Q-PCR

Figure 7:
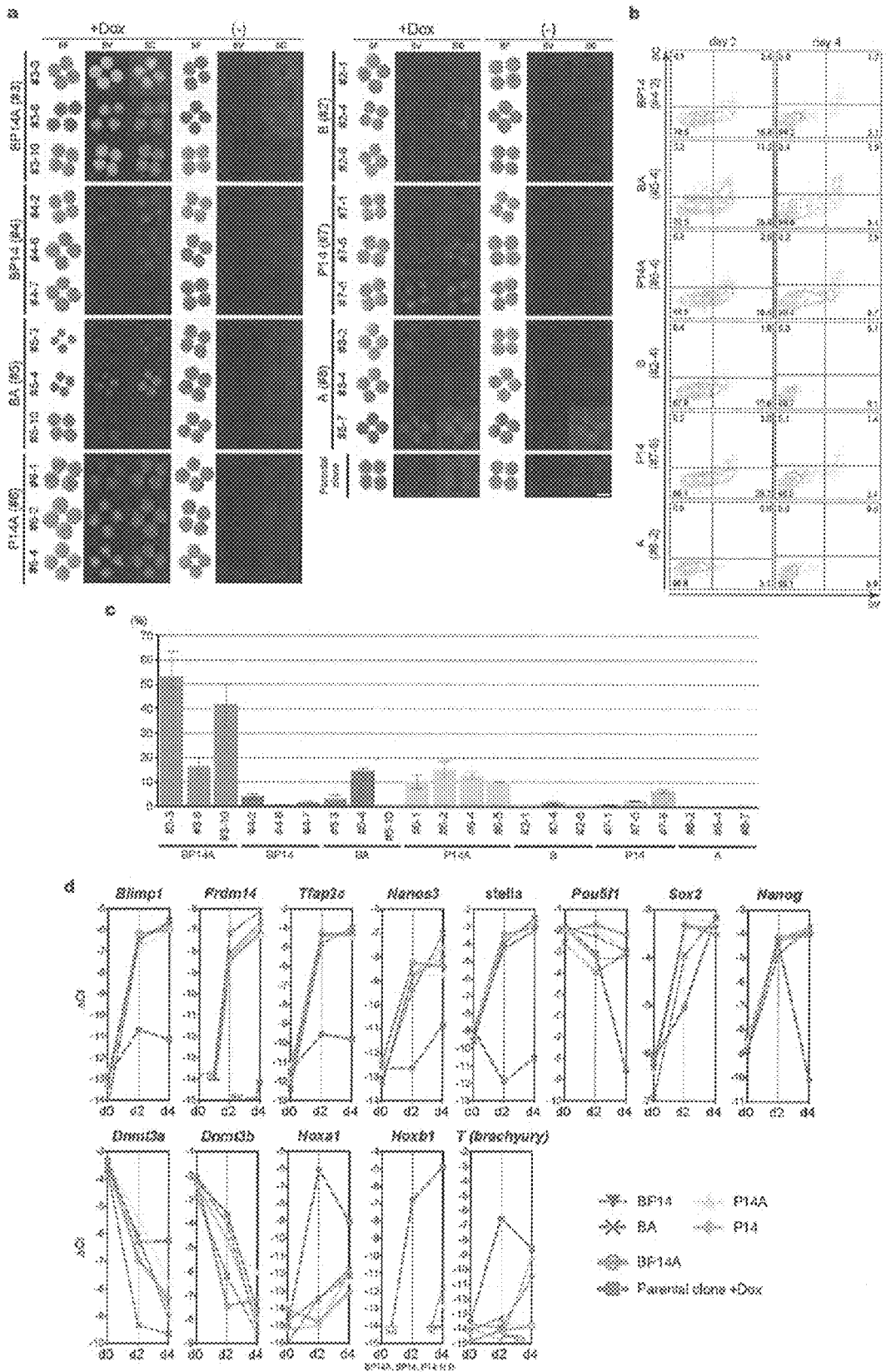
FIG. 7 shows an induction of a PGC-like state by one or two TFs.
Figure 9:
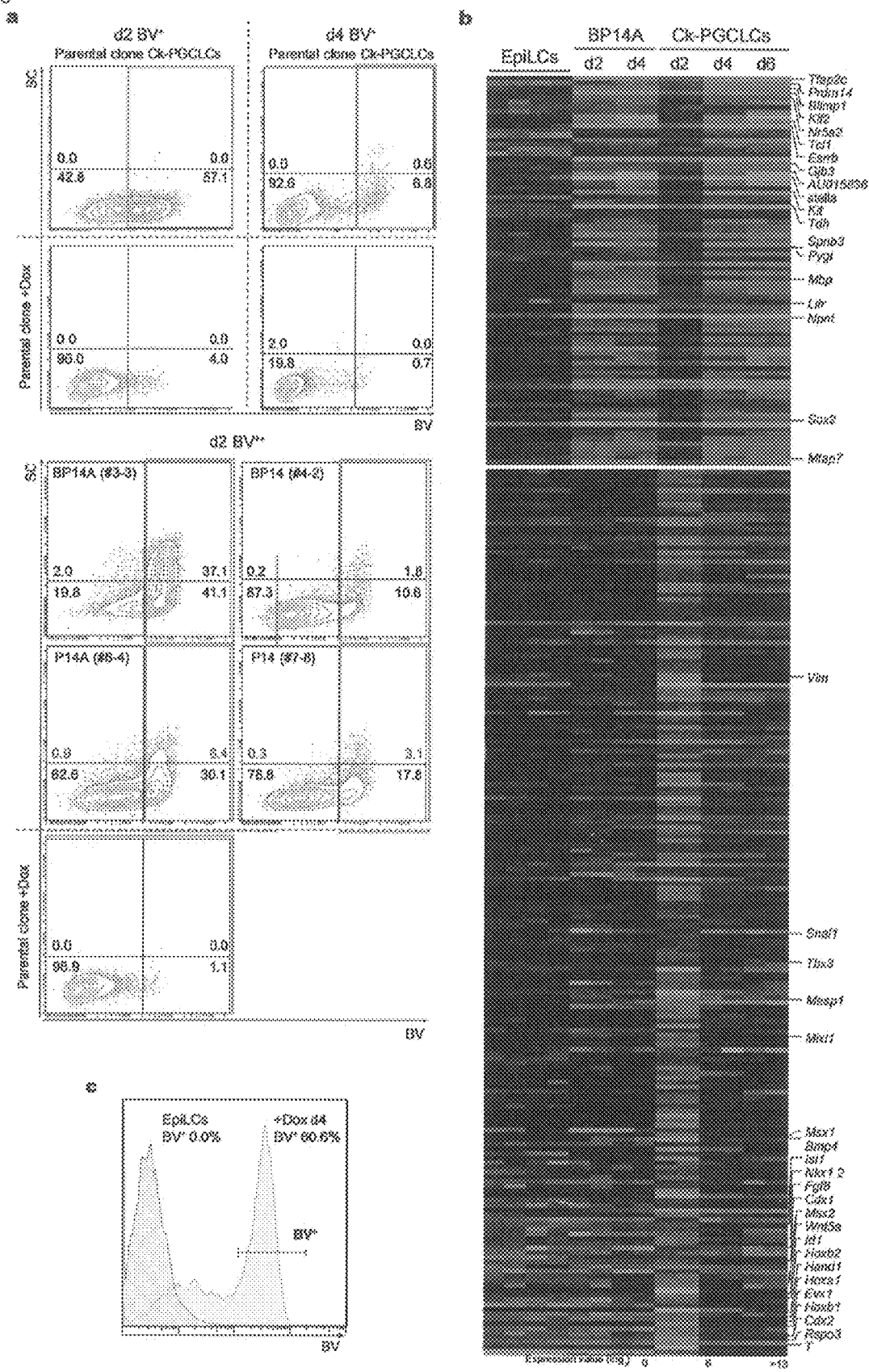
FIG. 9 shows FACS of the cells for microarray analysis and for epigenetic profiling, and "core PGC genes" and "somatic mesodermal genes".

For evaluating endogenous transcripts, TF-induced BV-positive cells were FACS-sorted on d2 and d4 with the gates shown in FIG. 1c and FIG. 7b. The sorting gates used for d2 and d4 CK-PGCLCs are shown in FIG. 9a. Aggregates were trypsinized and lysed as a whole unless otherwise specified. Total RNA was purified with RNeasy micro (QIAGEN) and RT was performed with SuperScriptIII (Invitrogen) primed with oligo-dT primer according to the manufacturer's protocol. Real-time PCR was performed with Power SYBR (Applied Biosystems) and CFX384 (BioRad). The gene expression levels are presented as ΔCt (in $\log_2$ scale) normalized (*Mech Dev* 113, 91-94 (2002)) with the average Ct values of Arbp and Ppia 14. To discriminate endogenous transcripts from exogenous ones, both the oligo-dT primer (Invitrogen) and gene-specific primers of interest were used for RT to reduce the RT bias due to differences in the distance between RT priming sites and amplified regions. The amplification efficiency of the newly designed primer sets was determined with pGEM-T-Easy plasmids harbouring the corresponding amplicons as templates. To verify both the endogenous and exogenous expression levels, samples were tested with CDS primers concurrently (data not shown). The primer sequences are listed in Table 4 (*Biol Reprod* 75, 705-716 (2006); *Nucleic Acids Res* 34, e42 (2006)).

TABLE 4

Quantitative RT-PCR

| | |
|---|---|
| Blimp1_F | AGCATGACCTGACATTGACACC (SEQ ID NO: 47) |
| Blimp1_R | CTCAACACTCTCATGTAAGAGGC (SEQ ID NO: 48) |
| Prdm14_F | ACAGCCAAGCAATTTGCACTAC (SEQ ID NO: 49) |
| Prdm14_R | TTACCTGGCATTTTCATTGCTC (SEQ ID NO: 50) |
| Tfap2c_F | GGGCTTTTCTCTCTTGGCTGGT (SEQ ID NO: 51) |
| Tfap2c_R | TCCACACGTCACCCACACAA (SEQ ID NO: 52) |
| Nanos3_F | CACTACGGCCTAGGAGCTTGG (SEQ ID NO: 53) |
| Nanos3_R | TGATCGCTGACAAGACTGTGGC (SEQ ID NO: 54) |
| stella_F | AGGCTCGAAGGAAATGAGTTTG (SEQ ID NO: 55) |
| stella_R | TCCTAATTCTTCCCGATTTTCG (SEQ ID NO: 56) |
| Pou5f1_F | GATGCTGTGAGCCAAGGCAAG (SEQ ID NO: 57) |
| Pou5f1_R | GGCTCCTGATCAACAGCATCAC (SEQ ID NO: 58) |
| Sox2_F | CATGAGAGCAAGTACTGGCAAG (SEQ ID NO: 59) |
| Sox2_R | CCAACGATATCAACCTGCATGG (SEQ ID NO: 60) |
| Nanog_F | CTTTCACCTATTAAGGTGCTTGC (SEQ ID NO: 61) |
| Nanog_R | TGGCATCGGTTCATCATGGTAC (SEQ ID NO: 62) |
| Dnmt3a_F | GACTCGCGTGCAATAACCTTAG (SEQ ID NO: 63) |
| Dnmt3a_R | GGTCACTTTCCCTCACTCTGG (SEQ ID NO: 64) |
| Dnmt3b_F | CTCGCAAGGTGTGGGCTTTTGTAAC (SEQ ID NO: 65) |
| Dnmt3b_R | CTGGGCATCTGTCATCTTTGCACC (SEQ ID NO: 66) |
| Hoxa1_F | GTGACTAGTCTTCTGCATGTCG (SEQ ID NO: 67) |
| Hoxa1_R | TCTGCTCTGGACCACATCACTC (SEQ ID NO: 68) |
| Hoxb1_F | GATCCTACAGGTCTTGGGACC (SEQ ID NO: 69) |
| Hoxb1_R | AGCTCAAAGGCACTGAACTGAG (SEQ ID NO: 70) |
| T_F | ATCAGAGTCCTTTGCTAGGTAG (SEQ ID NO: 71) |
| T_R | GTTACAATCTTCTGGCTATGC (SEQ ID NO: 72) |
| Gata6_F | CACAGTCCCCGTTCTTTTACTG (SEQ ID NO: 73) |
| Gata6_R | GTGGTACAGGCGTCAAGAGTG (SEQ ID NO: 74) |
| Arbp_F | CAAAGCTGAAGCAAAGGAAGAG (SEQ ID NO: 75) |
| Arbp_R | AATTAAGCAGGCTGACTTGGTTG (SEQ ID NO: 76) |
| Ppia_F | TTACCCATCAAACCATTCCTTCTG (SEQ ID NO: 77) |
| Ppia_R | AACCCAAAGAACTTCAGTGAGAGC (SEQ ID NO: 78) |

9. LacZ Staining

Cell aggregates at 12 hrs were trypsinized and fixed with 2% paraformaldehyde and 0.2% glutaraldehyde. Fixed cells were spread with Cytospin4 (Thermo Scientific) and stained with LacZ staining solution overnight (Nature 458, 766-770 (2009)).

10. Flow Cytometric Analysis and Cell Sorting

The sample preparations from cell aggregates were performed essentially as described previously (Cell 146, 519-532 (2011)). Fluorescent-activated cell sorting (FACS) was performed with a FACSAria or FACSAriaIII (BD) cell sorter. BV and SC fluorescence was detected with FITC and AmCyan Horizon V500 channel, respectively. Data were analyzed with FACSDiva (BD) or Flowjo (Tree Star Inc.) software.

11. Immunofluorescent Staining

BV-positive cells from BP14A-induced d4 aggregates were sorted with the gate shown in FIG. 9c, mixed with EpiLCs at a ratio of 1:1 and spread onto MAS-coated glass slides. Immunofluorescent staining was performed as reported previously (Cell 146, 519-532 (2011)). The primary antibodies (Abs) used in this study were as follows: anti-GFP (rat, monoclonal Ab (MAb); Nacalai Tesque), anti-DNMT3B (mouse, MAb; Imgenex), anti-H3K27me3 (rabbit, polyclonal Ab (pAb); Millipore), and anti-H3K9me2 (rabbit, pAb). Secondary antibodies were as follows: Alexa Fluor 568 anti-rabbit IgG, Alexa Fluor 488 anti-rat IgG, and Alexa Fluor 647 anti-mouse IgG (all three from Invitrogen). Images were captured with a confocal laser scan microscope (Olympus FV1000).

12. Bisulfite Sequencing

Genomic DNA was isolated and bisulfite treatment was conducted with an EpiTect Bisulfite Kit (QIAGEN) according to the manufacturer's protocol. The differentially methylated regions of Snrpn and H19 were amplified by PCR as previously reported (Genomics 79, 530-538). Sequences were determined and analyzed with QUMA (http://quma.cdb.riken.jp/top/index.html) (Nucleic Acids Res 36, W170-175 (2008)).

13. cDNA Amplification and Microarray Analysis

The cells surrounded with red rectangles in FIG. 9a were sorted by FACS. Note that the background level was different in sorting of CK-PGCLCs and TF-PGCLCs in D2. Total RNA isolation, reverse transcription and cDNA amplification were conducted as previously described (Cell 146, 519-532 (2011); Nucleic Acids Res 34, e42 (2006)). Samples were analyzed with a GeneChip Mouse Genome 430_2.0 Array (Affimetrix). Data were normalized with dChip and are shown in log 2 scale (Proc Natl Acad Sci USA 98, 31-36 (2001)). Probe selection criteria for analysis were as follows: (1) maximum expression score≥8, (2) maximum differential expression level≥2, (3) the highest average expression level among multiple probes for a gene, if any. Published data (GSE30056 (GSM744095-GSM744096, GSM744101-GSM744104)) were included in the analysis (Cell 146, 519-532 (2011)). We selected 4,479 probes and performed principal component analysis (PCA) with R (version 2.15.1) (R_Development_Core_Team. R, R Foundatin for Statistical Computing, 2012). For the differential gene expression analysis, we averaged biological duplicates or quadruplicates and selected "core PGC genes" (FIG. 9b, upper) and "somatic mesodermal genes" (Supplementary FIG. 9b, lower) according to the following criteria. "core PGC genes" were i) upregulated in BP14A-induced d2 more than 4-fold compared with both EpiLCs and the parental clone with Dox d2; ii) not downregulated in E9.5 PGCs (the differential expression level was less than 2-fold greater compared with that of BP14A-induced d2). "somatic mesodermal genes" exhibited at least 4-fold up-regulation in PGCLC d2 as compared with both EpiLCs and BP14A-induced d2. Representative genes are specified.

14. Seminiferous Tubule Injection

After the designated cell populations were sorted by FACS, 1×10⁴ cells/testis were injected into the neonatal testes of W/W$^v$ mice (7 dpp) basically as previously described (*Development* 132, 117122 (2005)). Anti-mouse CD4 antibody (50 mg/dose, clone GK1.5; eBioscience or Biolegend) was injected intraperitoneally at day 0, 2, or 4 for immunosuppression as necessary (*Biol Reprod* 68, 167-173 (2003)). The transplanted testes were analyzed 10 weeks after injection. For hematoxylin and eosin staining, testis samples were fixed with Bouin's solution, embedded in paraffin, and sectioned.

15. Intracytoplasmic Sperm Injection (ICSI)

ICSI was performed basically as reported previously (*Biol Reprod* 52, 709-720 (1995)). Briefly, seminiferous tubules with speimatogenesis colonies were gently minced and a spermatogenic cell suspension was prepared. Spermatozoa were injected into oocytes recovered from BDF1 mice. After in vitro embryo culture, 2-cell-stage embryos were transferred into the oviducts of E0.5 pseudopregnant mice (ICR). Pups were delivered by Caesarean section at E18.5. The primer sequences used for genotyping PCR are described in Table 3.

Results

Figure 5:
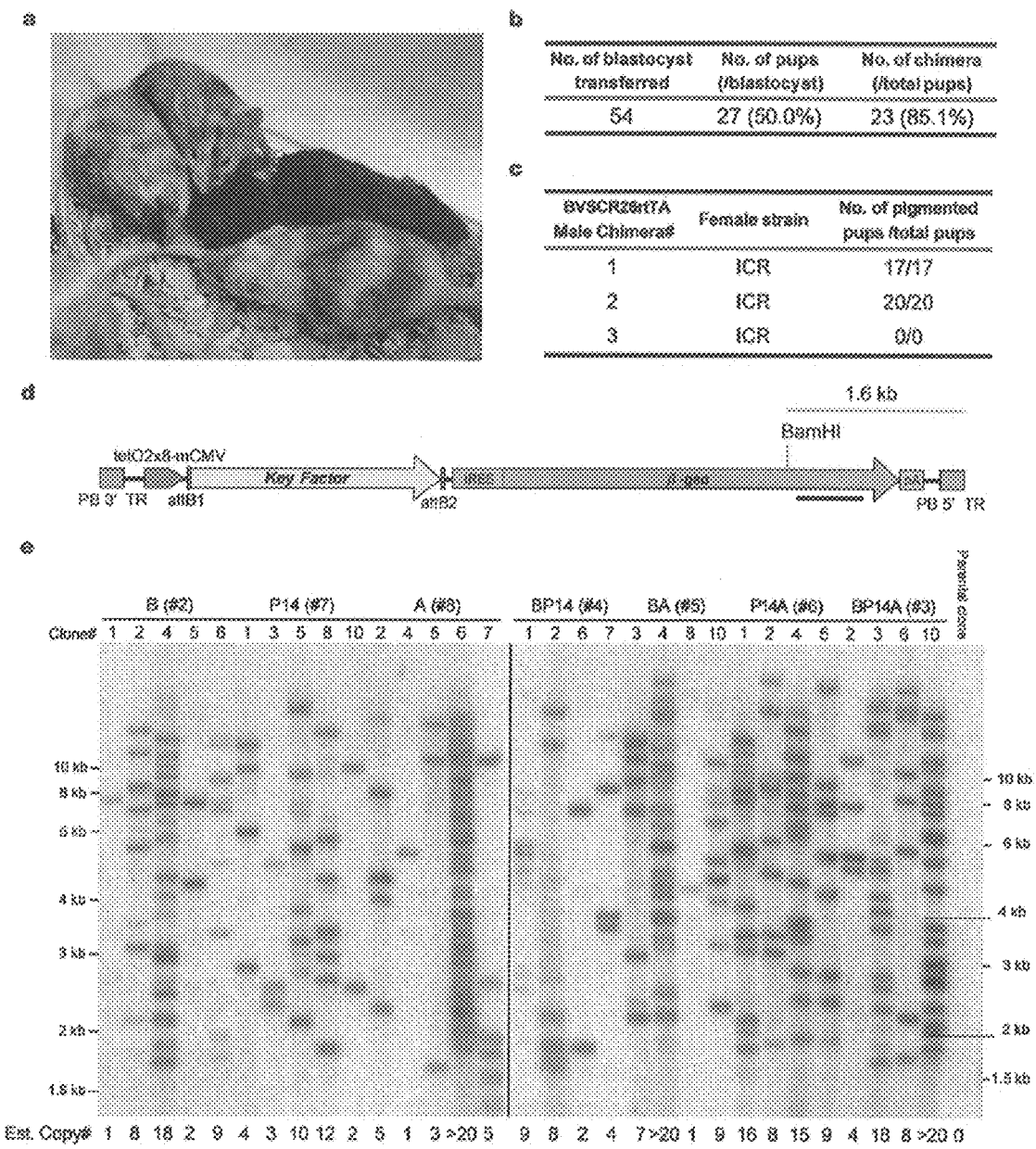
FIG. 5 shows generation of BVSCR26rtTA ESCs expressing key transcription factors under the control of tetracycline.

We derived ESCs expressing mVenus and ECFP under the control of Blimp1 and stella (also known as Dppa3/Pgc7) regulatory elements (BVSC), respectively (*Reproduction* 136, 503-514 (2008)), and reverse tetracycline transactivator (rtTA) under the control of the constitutively active Rosa26 locus (*Cell* 121, 465-477 (2005)) (BVSCR26rtTA ESCs) (FIG. 1a). During mouse development, Blimp1 expression signifies the onset of PGC specification, whereas stella begins expression in the established PGCs, and the BVSC expression is a faithful indicator for PGC specification and development both in vivo and in vitro (*Cell* 146, 519-532 (2011); *Science* 338, 971-975 (2012); *Reproduction* 136, 503-514 (2008)). We constructed piggyback transposon-based vectors expressing Blimp1, Prdm14 or Tfap2c under the control of tetracycline regulatory elements (TREs) and infected the BVSCR26rtTA ESCs karyotype) (FIG. 5a-c) with these vectors to isolate BVSCR26rtTA ESCs bearing transgenes for all three TFs (BVSCR26rtTA BP14A cells), two of the three TFs (BVSCR26rtTA BP14, BA and P14A cells), or one of the three TFs (BVSCR26rtTA B, P14, and A cells) (FIGS. 1a, 5d and 5e).

Figure 6:
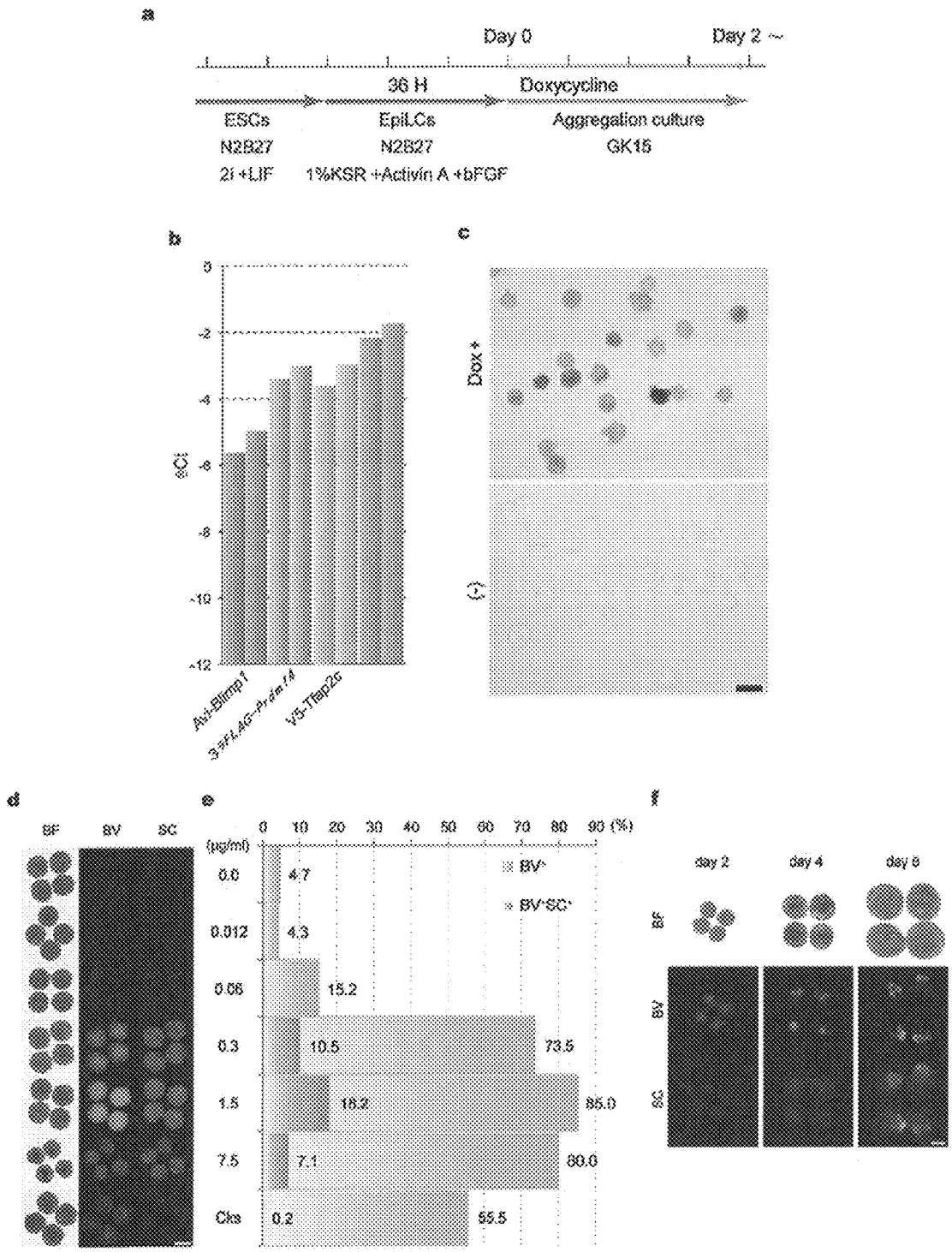
FIG. 6 shows a Dox-dose-dependent induction of BVSC in floating aggregates of EpiLCs induced from BVSCR26rtTA BP14A ESCs.

We first examined whether simultaneous forced expression of the three TFs induces EpiLCs into the germ cell fate. We induced BVSCR26rtTA BP14A cells (hereafter BP14A cells, Line 3-3) into EpiLCs, and then generated floating aggregates of ~2,000 EpiLCs in the absence of relevant cytokines with or without doxycycline (Dox, 1.5 µg/ml), a tetracycline analogue (FIG. 6a). The floating aggregates of EpiLCs without Dox did not show BVSC expression over the six-day period (FIG. 1b). In contrast, remarkably, those with Dox exhibited robust BVSC expression as early as day 2 (d2) of the Dox treatment (FIG. 1b). We confirmed that Dox induces exogenous TFs rapidly and at a high level in nearly all EpiLCs (FIG. 6b, c).

Fluorescence activated cell sorting (FACS) revealed that at d2 of Dox treatment, more than ~80% and ~30% of the cells expressed BV and SC, respectively (FIG. 1c), and the efficiency of BVSC induction was dependent on the dosage of Dox (FIG. 6d, e). Notably, the BVSC induction by Dox was much more efficient and faster than that by the cytokines: Most typically, the cytokines (BMP4, LIF, BMP8A, SCF, EGF) induce strong BV and SC around day 2 and 4, respectively (*Cell* 146, 519-532 (2011); *Science* 338, 971-975 (2012)) (FIG. 6f).

The BVSC-positive cells induced by Dox showed proliferation and persisted until day 4, but decreased thereafter (FIG. 1b). The other BP14A lines (Lines 3-6, 3-10) showed similar BVSC induction by Dox (FIG. 7a, c).

These findings demonstrate that the three TFs, BLIMP1, PRDM14 and TFAP2C, induced by Dox are sufficient for rapid and robust activation of the BVSC transgenes in EpiLCs.

We next set out to examine the expression of genes relevant for PGC specification in TF (BP14A)-induced BV-positive cells during the course of 96 hrs by Q-PCR.

Figure 8:
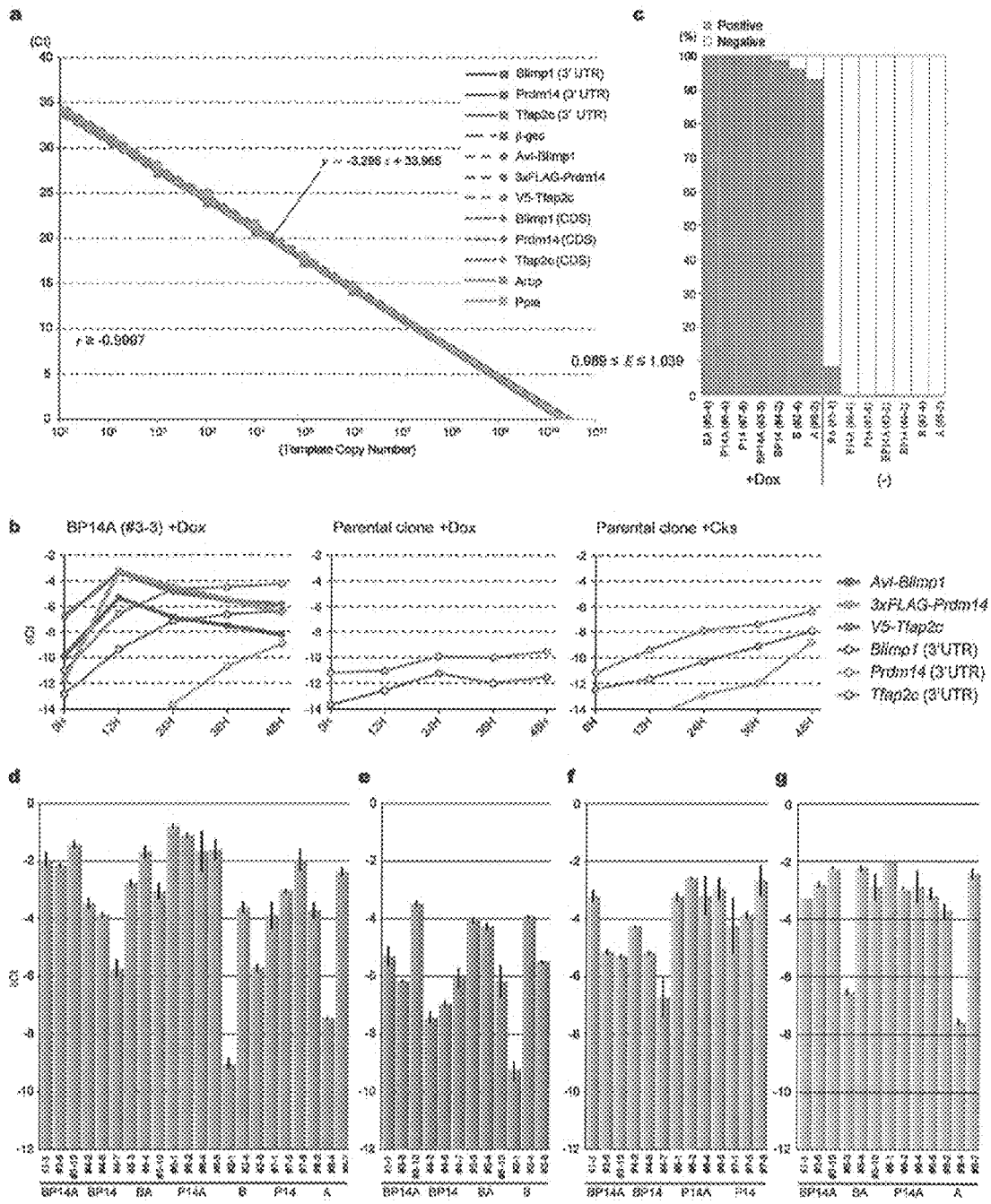
FIG. 8 shows quantification of the exogenous TF transcript levels induced by Dox.

We first confirmed that robust induction of exogenous TFs precedes endogenous Blimp1, Prdm14, and Tfap2c activation in induced whole-cell aggregates (FIG. 8a, b). We found that, as in the case of cytokine-induced BV-positive cells, TF-induced BV-positive cells showed up-regulation of key genes for PGC specification (Blimp1, Prdm14, Tfap2c, Nanos3, stella, Pou5f1, Sox2, Nanog) and down-regulation of key epigenetic modifiers (Dnmt3a and Dnmt3b) (FIG. 1d). Interestingly, we noted that in contrast to cytokine-induced BV-positive cells that exhibited transient up-regulation followed by repression of key mesodermal genes such as Hoxa1, Hoxb1 and T (Brachyury) (*Cell* 146, 519-532 (2011)), which was also seen during PGC specification in vivo (*Nature* 418, 293-300 (2002); *Biol Reprod* 75, 705-716 (2006); *Genes Dev* 22, 1617-1635 (2008)), TF-induced BV-positive cells did not show transient up-regulation of these genes, but rather continued to express them at low levels, or not at all (FIG. 1d).

These findings suggest that the TF (BP14A)-induced BV-positive cells acquire a transcriptional program similar to PGCs, but they lack transient acquisition of a mesodermal program, which is evident both during PGC specification in vivo and PGCLC induction by cytokines (see below).

We next analyzed whether forced expression of two of the three TFs or forced expression of one of the three TFs would induce BVSC in floating aggregates of EpiLCs (We evaluated at least three independent lines for each combination of TFs and for each TF).

We found that P14A, and to a lesser extent, BP14 and BA, and, strikingly, Prdm14 alone, activated BVSC, although all at lower efficiencies compared to the three TFs (FIG. 7a-c). We noted that the BA-induced aggregates (two out of three lines) looked somewhat fragile and remained small (FIG. 7a), and that forced expression of Blimp1 or Tfap2c alone did not activate BVSC (FIG. 7a-c).

We confirmed that all the lines show essentially uniform induction of exogenous TF(s) upon Dox treatment (FIG. 8c-g). It should be noted that we were not able to isolate BVSCR26rtTA B cells that express exogenous Blimp1 upon Dox treatment at levels as high as those of exogenous Prdm14 in BVSCR26rtTA P14 cells (FIG. 8d).

The two TFs (P14A, BP14, BA)- and single TF (Prdm14)-induced BV-positive cells exhibited gene expression dynamics very similar to those of the three TF (BP14A)-induced BV-positive cells (FIG. 7d), suggesting that once the key transcriptional circuitry for PGC specification is activated, the induced cells acquire similar transcriptional profiles.

We then determined the relationship between the rate of BVSC induction and the level of exogenous TF expression. As shown in FIG. 1e (data based on FIGS. 7c and 8d), BP14A induced BVSC much more efficiently than P14A or BA or P14 at similar whole exogenous TF transcript levels, indicating that Blimp1, Prdm14, and Tfap2c show a synergistic effect on the activation of PGC-like transcriptional profiles in EpiLCs.

To exclude the possibility that the TFs activate cytokine signaling, particularly BMP4 signaling, which in turn induces EpiLCs into a PGC-like state, we induced BP14A in EpiLCs with or without an inhibitor for BMP4 signaling [LDN193189, an inhibitor for activin receptor-like kinase 2/3 (ALK2/3)].

Figure 2:
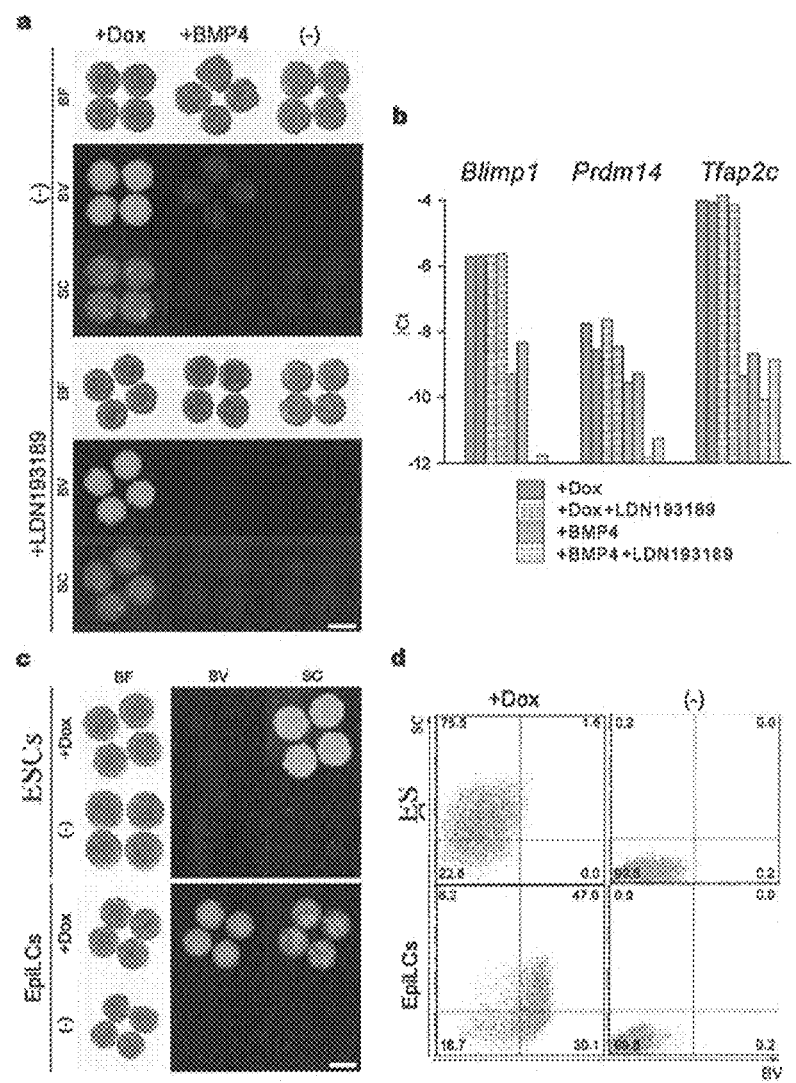
FIG. 2 shows an induction of a PGC-like state by TFs does not involve BMP4 signalling but requires an appropriate epigenetic background.

As shown in FIG. 2a, while LDN193189 efficiently blocked BV induction in EpiLCs by BMP4, it had no effect on BVSC induction by BP14A. Q-PCR analysis confirmed that LDN193189 inhibited Blimp1 and Prdm14 induction by BMP4 but not that by BP14A (FIG. 2b), demonstrating that induction of a PGC-like state by TFs results from direct activation of a PGC program by TFs.

We then examined whether induction of a PGC-like state by TFs requires an EpiLC state as an epigenetic background. While BP14A induced EpiLCs robustly into a PGC-like state, BP14A induction in ESCs resulted in a somewhat peculiar phenotype: intense SC activation with no BV (FIG. 2c, d).

We therefore conclude that a proper epigenetic background is essential for robust induction of a PGC-like state by TFs.

To characterize more fully the properties of the TF-induced PGC-like cells (hereafter referred to as TF-PGCLCs), we next determined the global transcription profiles of TF-PGCLCs [BV-positive cells induced by BP14A (d2 and d4), BP14 (d2), P14A (d2), P14 (d2)] by microarray analysis and compared them with those of PGCs in vivo [PGCs at embryonic day (E) 9.5] and cytokine-induced d2, d4, and d6 PGCLCs (hereafter referred to as Ck-PGCLCs) (FIG. 9a) (Cell 146, 519-532 (2011)).

Principal component analysis (PCA) revealed that all the TF-PGCLCs, irrespective of the TF combinations or of the induction period, bear similar transcriptomes, which are also similar to the transcriptomes of d4 and d6 Ck-PGCLCs and, to a lesser extent, of E9.5 PGCs (FIG. 3a), corroborating the idea that the exogenous TFs, at varying efficiencies depending on their combinations, activate endogenous key transcription circuitry for PGC specification, which creates a similar PGC-like state.

Figure 3:
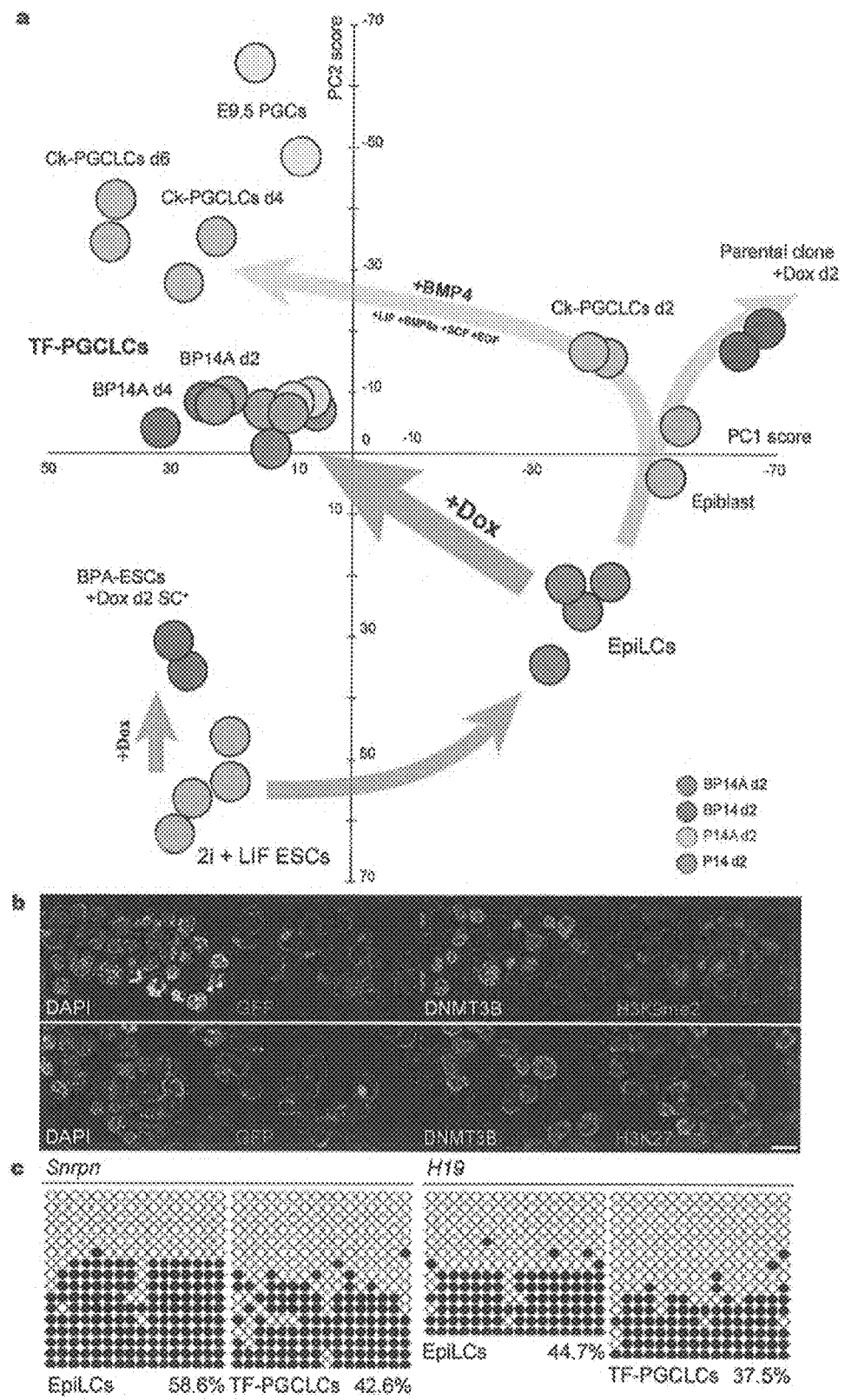
FIG. 3 shows global transcription profiles during PGCLC induction by TFs or by cytokines and epigenetic properties of TF-PGCLCs.

Consistent with the requirement of an appropriate epigenome for the TF-induced PGC-like state (FIG. 2c, d), the transcriptomes of the SC-positive cells induced by BP14A in ESCs were clearly different from those of TF/Ck-PGCLCs and PGCs, and were closer to those of ESCs (FIG. 3a). Notably, d2 Ck-PGCLCs showed a considerably different global transcription profile from those of TF-PGCLCs, d4 and d6 Ck-PGCLCs, and E9.5 PGCs, but a more similar profile to that of E5.75 epiblasts, indicating that d2 Ck-PGCLCs represent a transient state toward the acquisition of a PGC-like state from the EpiLC/epiblast states (FIG. 3a).

We looked at individual genes up-regulated in d2 TF (BP14A)-PGCLCs in comparison to those in EpiLCs/control EpiLCs without exogenous TFs but treated with Dox and found that genes such as Blimp1 (endogenous), Prdm14 (endogenous), Tfap2c (endogenous), stella, Sox2, Klf2, Tcl1, Esrrb, E1f3, Kit, Lifr, Nr5a2, Gjb3, Tdh, Spnb3, Pyg1, Mbp, Mtap7, Npnt, and AU015386 showed robust up-regulation: All these genes ("core PGC genes") were also up-regulated in d4 and d6 Ck-PGCLCs and in E9.5 PGCs (FIG. 9b).

We then examined the genes that showed up-regulation in d2 Ck-PGCLCs but not in d2 TF-PGCLCs in comparison to those in EpiLCs and this analysis revealed that the genes Hoxa1, Hoxb1, Hoxb2, Evx1, T(Brachyury), Cdx1, Cdx2, Hand1, Snai1, Mesp1, Id1, Msx1, Msx2, Nkx1.2, Isl1, Mixl1, Rspo3, Wnt5a, Fgf8 and Bmp4, all of which ("somatic mesodermal genes") show transient up-regulation in PGC precursors at around E6.75 to E7.25 and represent a somatic mesodermal program (Genes Dev 22, 1617-1635 (2008)), were transiently up-regulated in d2 Ck-PGCLCs but not in d2 TF-PGCLCs, and these genes were also down-regulated in d4 and d6 Ck-PGCLCs as well as in E9.5 PGCs (FIG. 9b).

Collectively, these findings provide evidence on a genome-wide scale that PGC specification by BMP4 activates both a key PGC program and somatic mesodermal program, the latter of which is eventually repressed by the former, and that the direct activation of key TFs confers EpiLCs with the key PGC program but not the somatic mesodermal program.

We next evaluated the epigenetic profiles of TF-PGCLCs. Immunofluorescence analysis revealed that, compared to EpiLCs that were exclusively positive for DNMT3B, BV-positive d4 TF-PGCLCs were negative/extremely weak for DNMT3B and showed a reduced level of Histone H3 Lysine 9 di-methylation (H3K9me2) and an elevated level of H3K27 tri-methylation (H3K27me3) (FIG. 3b, FIG. 9c). Analysis of the imprinting state by bisulfite sequencing showed that BV-positive d4 TF-PGCLCs retained the imprints on the paternally imprinted H19 and on the maternally imprinted Snrpn (FIG. 3c).

These findings suggest that the BV-positive d4 TF-PGCLCs acquire an epigenome similar to d6 Ck-PGCLCs and to migrating PGCs at E8.5-E9.5 (Cell 146, 519-532 (2011); Development 134, 2627-2638 (2007)).

Upon Dox withdrawal, the TF-PGCLCs should shut off exogenous TFs, but continue their endogenous transcription program, and may therefore serve as precursors for proper spermatogenesis.

To explore this possibility, we induced TF-PGCLCs by BP14A, purified the BV-positive cells (at d3, d4, and d6) (FIG. 4a), and transplanted them into seminiferous tubules of neonatal W/W$^v$ mice that lacked endogenous germ cells (Cell 146, 519-532 (2011); Development 132, 117-122 (2005)). Ten weeks after transplantation, we isolated the transplanted testes and examined for the presence of the seminiferous tubules with spermatogenesis. Strikingly, the testes transplanted with the TF-PGCLCs, particularly those sorted at d3 and d4, contained numerous tubules with signs of spermatogenesis (FIG. 4b, k): These tubules indeed contained abundant spermatozoa with proper morphology (FIG. 4c, d).

Figure 4:
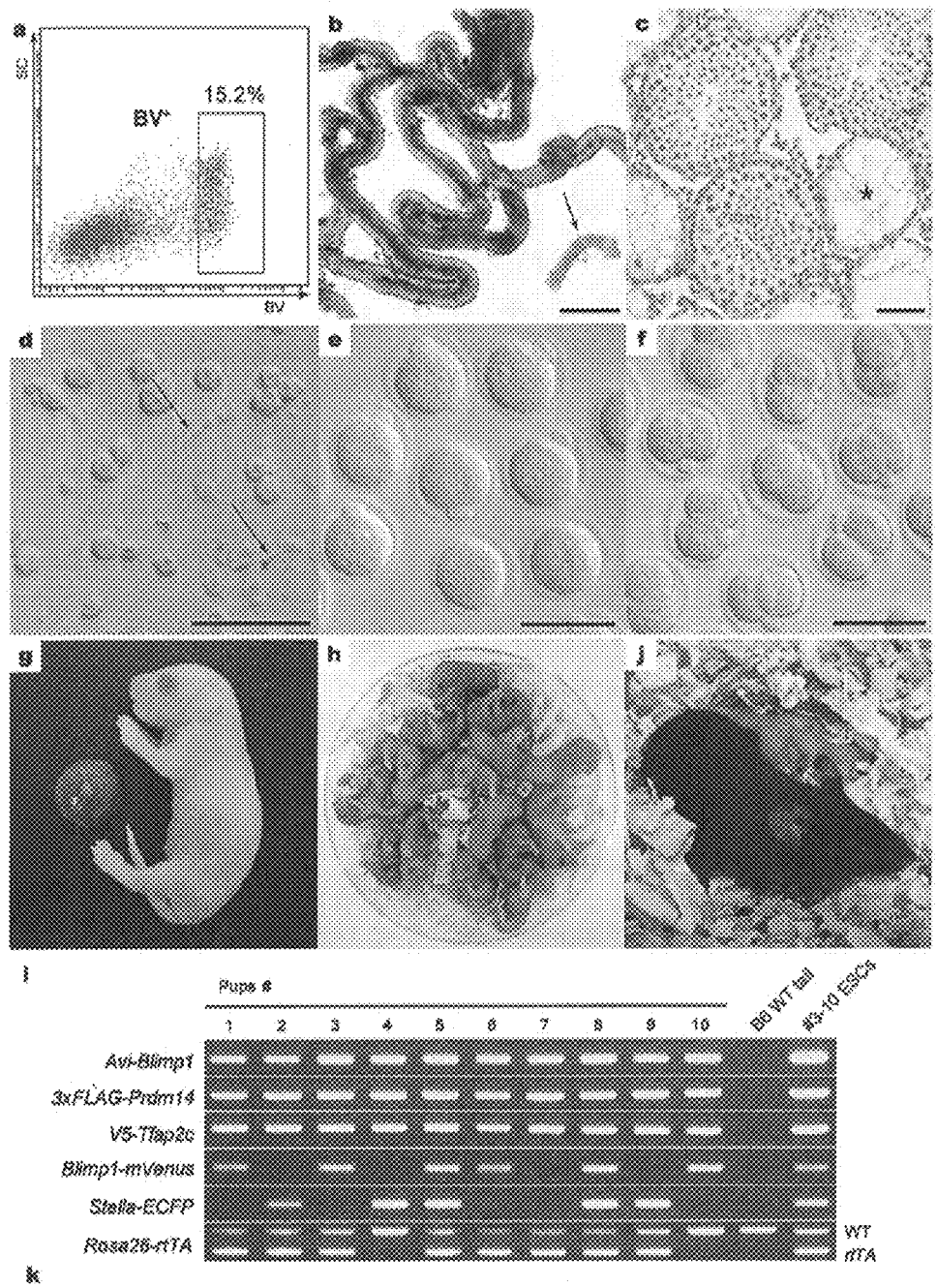
FIG. 4 shows a spermatogenesis and fertile offspring from TF (BP14A)-PGCLCs.
Figure 10:
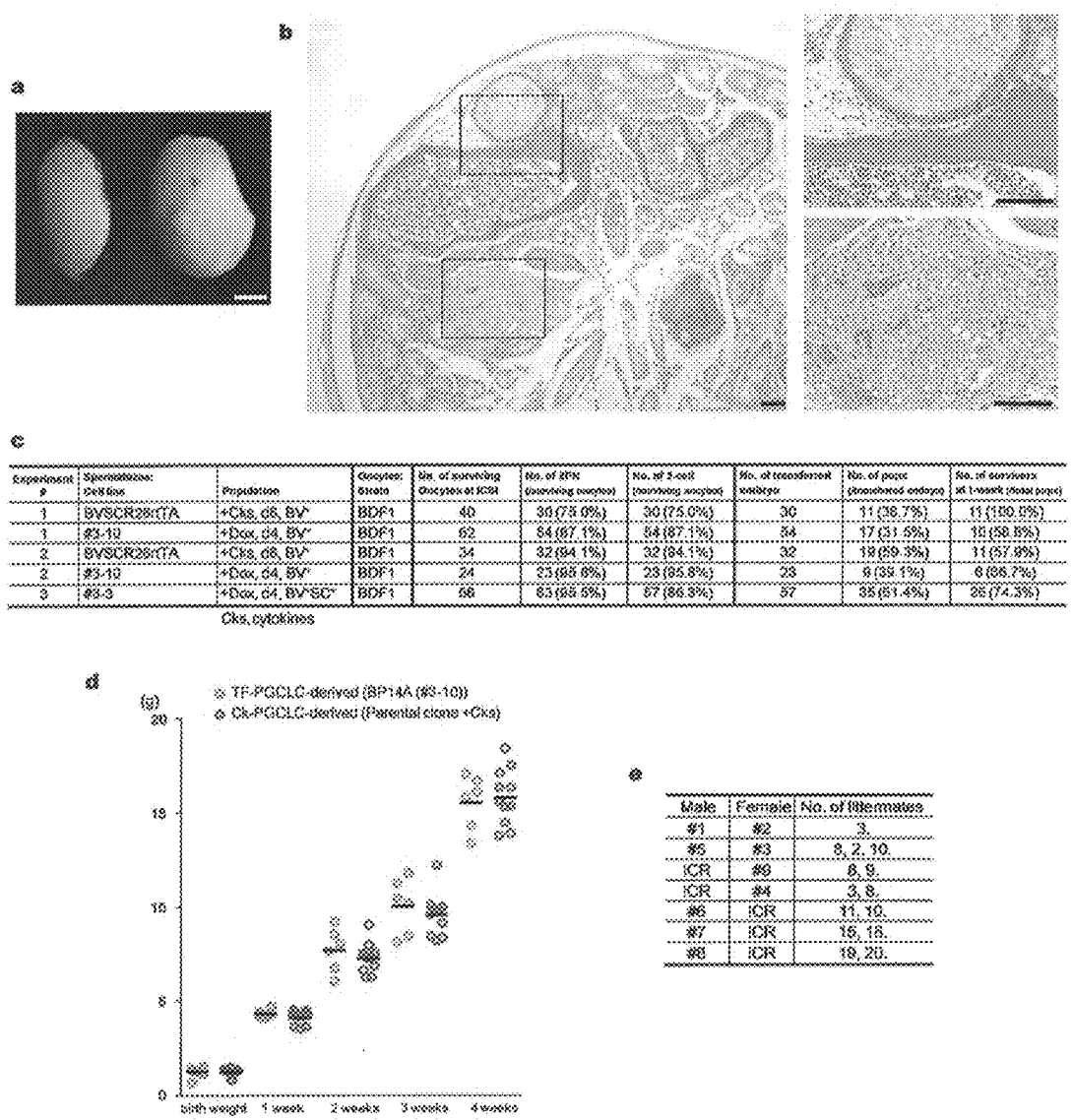
FIG. 10 shows development of embryos and growth of offspring derived from TF (BP14A)-PGCLC-derived spermatozoa.

Histological examination revealed that the spermatogenesis originated by TF-PGCLCs proceeded in a normal fashion (FIG. 4c). The control Ck-PGCLCs also contributed to proper spermatogenesis (FIG. 4k). In contrast, the SC-positive cells induced by activation of BP14A in ESCs did not contribute to spermatogenesis, but instead formed many foci of teratomas in six out of eight transplanted testes (FIG. 4k, FIG. 10a, b). We fertilized wild-type oocytes with TF-PGCLC-derived spermatozoa by intracytoplasmic sperm injection (ICSI) (Biol Reprod 52, 709-720 (1995)).

The resultant zygotes developed in an apparently normal fashion into 2-cell embryos (FIG. 4e, f, FIG. 10c). We transferred these embryos into oviducts of foster mothers and, 19 days later, obtained healthy offspring with grossly normal placenta (FIG. 4g, h). These offspring indeed bore transgenes for the exogenous TFs and the BVSCR26rtTA (FIG. 4i), but nonetheless grew up normally into fertile adults (FIG. 4j, FIG. 10d, e).

We conclude that the TF-PGCLCs function as bona fide precursors for the spermatogenesis and healthy offspring.

We have demonstrated that the three TFs examined herein, BLIMP1, PRDM14, and TFAP2C, activate a key PGC program in a synergistic fashion on an appropriate epigenetic background. The synergistic action of the three TFs indicates their mutual regulation. We have also shown that PRDM14 is a minimum requirement for this activation and that neither BLIMP1 alone nor TFAP2C alone is sufficient to activate the PGC program by itself.

The system we have presented not only offers an opportunity to clarify the precise mechanism of epigenetic reprogramming in PGCs (genome-wide DNA demethylation and histone modification changes (*Development* 139, 15-31 (2012)), but also points to the importance of conducting mechanistic studies to determine how the key TFs work on an appropriate epigenetic background. It should also be feasible to explore TF-based regulation of further critical processes of germ cell development. The TF-based control of germ cell development may also be applicable to mammals other than mice, including humans.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

This application is based on patent application No. 61/771,619 filed in U.S.A., the contents of which are hereby incorporated by reference.

The invention claimed is:

1. A method of producing a primordial germ cell-like cell (PGCLC) from an isolated epiblast or epiblast-like cell (EpiLC), which comprises allowing the epiblast or EpiLC to express exogenous transcription factor(s) selected from the group consisting of:
   (i) Blimp1, Prdm14 and Tfap2c;
   (ii) Blimp1 and Prdm14;
   (iii) Blimp1 and Tfap2c;
   (iv) Prdm14 and Tfap2c; and
   (v) Prdm14;
thereby inducing the epiblast or EpiLC into a PGC state without acquiring transient mesodermal program, wherein the epiblast or EpiLC is induced into a PGCLC in the absence of BMP4.

2. The method according to claim 1, wherein nucleic acid(s) encoding the exogenous transcription factor(s) is/are introduced into the epiblast or EpiLC.

3. The method according to claim 1, wherein nucleic acid(s) encoding the exogenous transcription factor(s) has/have been introduced into the epiblast or EpiLC, in a form capable of being conditionally expressed, prior to the induction of the epiblast or EpiLC.

4. The method according to claim 3, wherein the epiblast or EpiLC is cultured under conditions which the nucleic acid(s) encoding the exogenous transcription factor(s) is/are expressed for 1 to 5 days.

5. The method according to claim 1, wherein the EpiLC is obtained by culturing a pluripotent stem cell (PSC) in the presence of activin A (ActA), optionally in the presence of further basic fibroblast growth factor (bFGF) and/or Knock-out™ Serum Replacement (KSR).

6. The method according to claim 5, wherein the PSC is an embryonic stem cell (ESC) or induced pluripotent stem cell (iPSC).

7. The method according to claim 1, wherein nucleic acid(s) encoding the exogenous transcription factor(s) is/are in a form capable of disappearing from the PGCLC.

8. The method according to claim 7, wherein the nucleic acid(s) is/are carried on vector(s) selected from the group consisting of plasmid, episomal vector, transposon, adenoviral vector and Sendai viral vector.

9. The method according to claim 1, wherein the EpiLC is derived from mouse or human.

10. A method of producing a PGCLC from a PSC, which comprises the following steps I) and II):
   I) the step for producing an EpiLC by culturing a PSC in the presence of ActA, optionally in the presence of further bFGF and/or KSR;
   II) the step for inducing the EpiLC obtained in the step I) into a PGCLC by the method according to claim 1.

11. The method according to claim 10, which further comprises:
   III) the step for selecting a Blimp1-positive cell from the cells obtained in the step II).

12. The method according to claim 1, wherein the epiblast or EpiLC is induced into a PGCLC in the absence of BMP4, LIF, SCF, BMP8b, and EGF.

13. The method according to claim 10, wherein the step II) is performed in the absence of BMP4, LIF, SCF, BMP8b, and EGF.

14. The method according to claim 1, wherein exogenous transcription factor(s) is/are selected from the group consisting of:
   (i) Blimp1, Prdm14 and Tfap2c;
   (iii) Blimp1 and Tfap2c;
   (iv) Prdm14 and Tfap2c; and
   (v) Prdm14.

15. The method according to claim 1, wherein exogenous transcription factor(s) is/are selected from the group consisting of:
   (i) Blimp1, Prdm14 and Tfap2c;
   (iii) Blimp1 and Tfap2c; and
   (iv) Prdm14 and Tfap2c.

16. The method according to claim 10, wherein exogenous transcription factor(s) is/are selected from the group consisting of:
   (i) Blimp1, Prdm14 and Tfap2c;
   (iii) Blimp1 and Tfap2c;
   (iv) Prdm14 and Tfap2c; and
   (v) Prdm14.

17. The method according to claim 10, wherein exogenous transcription factor(s) is/are selected from the group consisting of:
   (i) Blimp1, Prdm14 and Tfap2c;
   (iii) Blimp1 and Tfap2c; and
   (iv) Prdm14 and Tfap2c.

* * * * *

SEQUENCE LISTING

```
<160> NUMBER OF SEQ ID NOS: 78

<210> SEQ ID NO 1
<211> LENGTH: 5165
<212> TYPE: DNA
<213> ORGANISM: Homo sapiens
<220> FEATURE:
<221> NAME/KEY: CDS
<222> LOCATION: (235)..(2712)

<400> SEQUENCE: 1
gggaagccag acggttaaca cagacaaagt gctgccgtga cactcggccc tccagtgttg      60
cggagaggca agagcagcga ccgcggcacc tgtccgcccg gagctgggac gcgggcgccc     120
gggcggccgg acgaagcgag gagggaccgc cgaggtgcgc gtctgtgcgg ctcagcctgg     180
cgggggacgc ggggagaatg tggactgggt agagatgaac gagacttttc tcag atg      237
                                                                Met
                                                                  1 ttg gat att tgc ttg gaa aaa cgt gtg ggt acg acc ttg gct gcc ccc      285
Leu Asp Ile Cys Leu Glu Lys Arg Val Gly Thr Thr Leu Ala Ala Pro
          5                  10                  15 aag tgt aac tcc agc act gtg agg ttt cag gga ttg gca gag ggg acc      333
Lys Cys Asn Ser Ser Thr Val Arg Phe Gln Gly Leu Ala Glu Gly Thr
     20                  25                  30 aag ggg acc atg aaa atg gac atg gag gat gcg gat atg act ctg tgg      381
Lys Gly Thr Met Lys Met Asp Met Glu Asp Ala Asp Met Thr Leu Trp
 35                  40                  45 aca gag gct gag ttt gaa gag aag tgt aca tac att gtg aac gac cac      429
Thr Glu Ala Glu Phe Glu Glu Lys Cys Thr Tyr Ile Val Asn Asp His
 50                  55                  60                  65 ccc tgg gat tct ggt gct gat ggc ggt act tcg gtt cag gcg gag gca      477
Pro Trp Asp Ser Gly Ala Asp Gly Gly Thr Ser Val Gln Ala Glu Ala
                 70                  75                  80 tcc tta cca agg aat ctg ctt ttc aag tat gcc acc aac agt gaa gag      525
Ser Leu Pro Arg Asn Leu Leu Phe Lys Tyr Ala Thr Asn Ser Glu Glu
             85                  90                  95 gtt att gga gtg atg agt aaa gaa tac ata cca aag ggc aca cgt ttt      573
Val Ile Gly Val Met Ser Lys Glu Tyr Ile Pro Lys Gly Thr Arg Phe
        100                 105                 110
```

```
gga ccc cta ata ggt gaa atc tac acc aat gac aca gtt cct aag aac     621
Gly Pro Leu Ile Gly Glu Ile Tyr Thr Asn Asp Thr Val Pro Lys Asn
    115                 120                 125 gcc aac agg aaa tat ttt tgg agg atc tat tcc aga ggg gag ctt cac     669
Ala Asn Arg Lys Tyr Phe Trp Arg Ile Tyr Ser Arg Gly Glu Leu His
130                 135                 140                 145 cac ttc att gac ggc ttt aat gaa gag aaa agc aac tgg atg cgc tat     717
His Phe Ile Asp Gly Phe Asn Glu Glu Lys Ser Asn Trp Met Arg Tyr
                150                 155                 160 gtg aat cca gca cac tct ccc cgg gag caa aac ctg gct gcg tgt cag     765
Val Asn Pro Ala His Ser Pro Arg Glu Gln Asn Leu Ala Ala Cys Gln
        165                 170                 175 aac ggg atg aac atc tac ttc tac acc att aag ccc atc cct gcc aac     813
Asn Gly Met Asn Ile Tyr Phe Tyr Thr Ile Lys Pro Ile Pro Ala Asn
            180                 185                 190 cag gaa ctt ctt gtg tgg tat tgt cgg gac ttt gca gaa agg ctt cac     861
Gln Glu Leu Leu Val Trp Tyr Cys Arg Asp Phe Ala Glu Arg Leu His
    195                 200                 205 tac cct tat ccc gga gag ctg aca atg atg aat ctc aca caa aca cag     909
Tyr Pro Tyr Pro Gly Glu Leu Thr Met Met Asn Leu Thr Gln Thr Gln
210                 215                 220                 225 agc agt cta aag caa ccg agc act gag aaa aat gaa ctc tgc cca aag     957
Ser Ser Leu Lys Gln Pro Ser Thr Glu Lys Asn Glu Leu Cys Pro Lys
                230                 235                 240 aat gtc cca aag aga gag tac agc gtg aaa gaa atc cta aaa ttg gac    1005
Asn Val Pro Lys Arg Glu Tyr Ser Val Lys Glu Ile Leu Lys Leu Asp
        245                 250                 255 tcc aac ccc tcc aaa gga aag gac ctc tac cgt tct aac att tca ccc    1053
Ser Asn Pro Ser Lys Gly Lys Asp Leu Tyr Arg Ser Asn Ile Ser Pro
            260                 265                 270 ctc aca tca gaa aag gac ctc gat gac ttt aga aga cgt ggg agc ccc    1101
Leu Thr Ser Glu Lys Asp Leu Asp Asp Phe Arg Arg Arg Gly Ser Pro
    275                 280                 285 gaa atg ccc ttc tac cct cgg gtc gtt tac ccc atc cgg gcc cct ctg    1149
Glu Met Pro Phe Tyr Pro Arg Val Val Tyr Pro Ile Arg Ala Pro Leu
290                 295                 300                 305 cca gaa gac ttt ttg aaa gct tcc ctg gcc tac ggg atc gag aga ccc    1197
Pro Glu Asp Phe Leu Lys Ala Ser Leu Ala Tyr Gly Ile Glu Arg Pro
                310                 315                 320 acg tac atc act cgc tcc ccc att cca tcc tcc acc act cca agc ccc    1245
Thr Tyr Ile Thr Arg Ser Pro Ile Pro Ser Ser Thr Thr Pro Ser Pro
        325                 330                 335 tct gca aga agc agc ccc gac caa agc ctc aag agc tcc agc cct cac    1293
Ser Ala Arg Ser Ser Pro Asp Gln Ser Leu Lys Ser Ser Ser Pro His
            340                 345                 350 agc agc cct ggg aat acg gtg tcc cct gtg ggc ccc ggc tct caa gag    1341
Ser Ser Pro Gly Asn Thr Val Ser Pro Val Gly Pro Gly Ser Gln Glu
    355                 360                 365 cac cgg gac tcc tac gct tac ttg aac gcg tcc tac ggc acg gaa ggt    1389
His Arg Asp Ser Tyr Ala Tyr Leu Asn Ala Ser Tyr Gly Thr Glu Gly
370                 375                 380                 385 ttg ggc tcc tac cct ggc tac gca ccc ctg ccc cac ctc ccg cca gct    1437
Leu Gly Ser Tyr Pro Gly Tyr Ala Pro Leu Pro His Leu Pro Pro Ala
                390                 395                 400 ttc atc ccc tcg tac aac gct cac tac ccc aag ttc ctc ttg ccc ccc    1485
Phe Ile Pro Ser Tyr Asn Ala His Tyr Pro Lys Phe Leu Leu Pro Pro
        405                 410                 415 tac ggc atg aat tgt aat ggc ctg agc gct gtg agc agc atg aat ggc    1533
Tyr Gly Met Asn Cys Asn Gly Leu Ser Ala Val Ser Ser Met Asn Gly
            420                 425                 430
```

```
atc aac aac ttt ggc ctc ttc ccg agg ctg tgc cct gtc tac agc aat    1581
Ile Asn Asn Phe Gly Leu Phe Pro Arg Leu Cys Pro Val Tyr Ser Asn
435             440                 445 ctc ctc ggt ggg ggc agc ctg ccc cac ccc atg ctc aac ccc act tct    1629
Leu Leu Gly Gly Gly Ser Leu Pro His Pro Met Leu Asn Pro Thr Ser
450             455                 460                 465 ctc ccg agc tcg ctg ccc tca gat gga gcc cgg agg ttg ctc cag ccg    1677
Leu Pro Ser Ser Leu Pro Ser Asp Gly Ala Arg Arg Leu Leu Gln Pro
            470                 475                 480 gag cat ccc agg gag gtg ctt gtc ccg gcg ccc cac agt gcc ttc tcc    1725
Glu His Pro Arg Glu Val Leu Val Pro Ala Pro His Ser Ala Phe Ser
                485                 490                 495 ttt acc ggg gcc gcc gcc agc atg aag gac aag gcc tgt agc ccc aca    1773
Phe Thr Gly Ala Ala Ala Ser Met Lys Asp Lys Ala Cys Ser Pro Thr
        500                 505                 510 agc ggg tct ccc acg gcg gga aca gcc gcc acg gca gaa cat gtg gtg    1821
Ser Gly Ser Pro Thr Ala Gly Thr Ala Ala Thr Ala Glu His Val Val
515                 520                 525 cag ccc aaa gct acc tca gca gcg atg gca gcc ccc agc agc gac gaa    1869
Gln Pro Lys Ala Thr Ser Ala Ala Met Ala Ala Pro Ser Ser Asp Glu
530             535                 540                 545 gcc atg aat ctc att aaa aac aaa aga aac atg acc ggc tac aag acc    1917
Ala Met Asn Leu Ile Lys Asn Lys Arg Asn Met Thr Gly Tyr Lys Thr
            550                 555                 560 ctt ccc tac ccg ctg aag aag cag aac ggc aag atc aag tac gaa tgc    1965
Leu Pro Tyr Pro Leu Lys Lys Gln Asn Gly Lys Ile Lys Tyr Glu Cys
                565                 570                 575 aac gtt tgc gcc aag act ttc ggc cag ctc tcc aat ctg aag gtc cac    2013
Asn Val Cys Ala Lys Thr Phe Gly Gln Leu Ser Asn Leu Lys Val His
        580                 585                 590 ctg aga gtg cac agt gga gaa cgg cct ttc aaa tgt cag act tgc aac    2061
Leu Arg Val His Ser Gly Glu Arg Pro Phe Lys Cys Gln Thr Cys Asn
595                 600                 605 aag ggc ttt act cag ctc gcc cac ctg cag aaa cac tac ctg gta cac    2109
Lys Gly Phe Thr Gln Leu Ala His Leu Gln Lys His Tyr Leu Val His
610             615                 620                 625 acg gga gaa aag cca cat gaa tgc cag gtc tgc cac aag aga ttt agc    2157
Thr Gly Glu Lys Pro His Glu Cys Gln Val Cys His Lys Arg Phe Ser
            630                 635                 640 agc acc agc aat ctc aag acc cac ctg cga ctc cat tct gga gag aaa    2205
Ser Thr Ser Asn Leu Lys Thr His Leu Arg Leu His Ser Gly Glu Lys
                645                 650                 655 cca tac caa tgc aag gtg tgc cct gcc aag ttc acc cag ttt gtg cac    2253
Pro Tyr Gln Cys Lys Val Cys Pro Ala Lys Phe Thr Gln Phe Val His
        660                 665                 670 ctg aaa ctg cac aag cgt ctg cac acc cgg gag cgg ccc cac aag tgc    2301
Leu Lys Leu His Lys Arg Leu His Thr Arg Glu Arg Pro His Lys Cys
675                 680                 685 tcc cag tgc cac aag aac tac atc cat ctc tgt agc ctc aag gtt cac    2349
Ser Gln Cys His Lys Asn Tyr Ile His Leu Cys Ser Leu Lys Val His
690             695                 700                 705 ctg aaa ggg aac tgc gct gcg gcc ccg gcg cct ggg ctg ccc ttg gaa    2397
Leu Lys Gly Asn Cys Ala Ala Ala Pro Ala Pro Gly Leu Pro Leu Glu
            710                 715                 720 gat ctg acc cga atc aat gaa gaa atc gag aag ttt gac atc agt gac    2445
Asp Leu Thr Arg Ile Asn Glu Glu Ile Glu Lys Phe Asp Ile Ser Asp
                725                 730                 735 aat gct gac cgg ctc gag gac gtg gag gat gac atc agt gtg atc tct    2493
Asn Ala Asp Arg Leu Glu Asp Val Glu Asp Asp Ile Ser Val Ile Ser
```

-continued

|  |  |
|---|---|
| 740 745 750<br>gta gtg gag aag gaa att ctg gcc gtg gtc aga aaa gag aaa gaa gaa<br>Val Val Glu Lys Glu Ile Leu Ala Val Val Arg Lys Glu Lys Glu Glu<br>755 760 765 | 2541 |
| act ggc ctg aaa gtg tct ttg caa aga aac atg ggg aat gga ctc ctc<br>Thr Gly Leu Lys Val Ser Leu Gln Arg Asn Met Gly Asn Gly Leu Leu<br>770 775 780 785 | 2589 |
| tcc tca ggg tgc agc ctt tat gag tca tca gat cta ccc ctc atg aag<br>Ser Ser Gly Cys Ser Leu Tyr Glu Ser Ser Asp Leu Pro Leu Met Lys<br>790 795 800 | 2637 |
| ttg cct ccc agc aac cca cta cct ctg gta cct gta aag gtc aaa caa<br>Leu Pro Pro Ser Asn Pro Leu Pro Leu Val Pro Val Lys Val Lys Gln<br>805 810 815 | 2685 |
| gaa aca gtt gaa cca atg gat cct taa gattttcaga aaacacttat<br>Glu Thr Val Glu Pro Met Asp Pro<br>820 825 | 2732 |
| tttgtttctt aagttatgac ttggtgagtc agggtgcctg taggaagtgg cttgtacata | 2792 |
| atcccagctc tgcaaagctc tctcgacagc aaatggtttc ccctcacctc tggaattaaa | 2852 |
| gaaggaactc caaagttact gaaatctcag ggcatgaaca aggcaaaggc catatatata | 2912 |
| tatatatata tatctgtata catattatat atacttattt acacctgtgt ctatatattt | 2972 |
| gcccctgtgt attttgaata tttgtgtgga catgtttgca tagccttccc attactaaga | 3032 |
| ctattaccta gtcataatta ttttttcaat gataatcctt cataatttat tatacaattt | 3092 |
| atcattcaga aagcaataat taaaaaagtt tacaatgact ggaaagattc cttgtaattt | 3152 |
| gagtataaat gtattttttgt cttgtggcca ttctttgtag ataatttctg cacatctgta | 3212 |
| taagtaccta agatttagtt aaacaaatat atgacttcag tcaacctctc tctctaataa | 3272 |
| tggtttgaaa atgaggtttg ggtaattgcc aatgttggac agttgatgtg ttcattcctg | 3332 |
| ggatcctatc atttgaacag cattgtacat aacttggggg tatgtgtgca ggattaccca | 3392 |
| agaataactt aagtagaaga aacaagaaag ggaatcttgt atattttttgt tgatagttca | 3452 |
| tgtttttccc ccagccacaa ttttaccgga agggtgacag gaaggcttta ccaacctgtc | 3512 |
| tctccctcca aaagagcaga atcctcccac cgccctgccc tccccaccga gtcctgtggc | 3572 |
| cattcagagc ggccacatga cttttgcatc cattgtatta tcagaaaatg tgaagaagaa | 3632 |
| aaaaatgcca tgttttaaaa ccactgcgaa aatttcccca aagcataggt ggctttgtgt | 3692 |
| gtgtgcgatt tgggggcttg agtctgggtg gtgttttgtt gttggttttt gttgcttttt | 3752 |
| tttttttttt tttttttaatg tcaaaattgc acaaacatgg tgctctacca ggaaggattc | 3812 |
| gaggtagata ggctcaggcc cactttaaa aacaaacaca caaacaacaa aaaacgggta | 3872 |
| ttctagtcat cttgggggtaa aagcgggtaa tgaacattcc tatccccaac acatcaattg | 3932 |
| tatttttttct gtaaaactca gatttttcctc agtatttgtg ttttttacatt ttatggttaa | 3992 |
| tttaatggaa gatgaaaggg cattgcaaag ttgttcaaca acagttaccct cattgagtgt | 4052 |
| gtccagtagt gcaggaaatg atgtcttatc taatgatttg cttctctaga ggagaaaccg | 4112 |
| agtaaatgtg ctccagcaag atagactttg tgttattcta tctttttattc tgctaagccc | 4172 |
| aaagattaca tgttggtgtt caaagtgtag caaaaaatga tgtatattta taaatctatt | 4232 |
| tataccacta tatcatatgt atatatatttt ataaccactt aaattgtgag ccaagccatg | 4292 |
| taaaagatct acttttttcta agggcaaaaa aaaaaaaaaa aaaaaagaa cactcctttc | 4352 |
| tgagactttc cttaatactt ggtgacctca caatcacgtc ggtatgattg ggcacccttg | 4412 |
| cctactgtaa gagaccctaa aaccttggtg cagtggtggg gaccacaaaa caaccaggga | 4472 |

-continued

```
ggaagagata catcattttt tagtattaag gaccatctaa gacagctcta ttttttttt     4532
gccactttat gattatgtgg tcacacccaa gtcacagaaa taaaaaactg actttaccgc    4592
tgcaatttt  ctgttttcct ccttactaaa tactgataca ttactccaat ctattttata    4652
attatatttg acattttgtt cacatcaact aatgttcacc tgtagaagag aacaaatttc    4712
gaataatcca gggaaaccca agagccttac tggtcttctg taacttccaa gactgacagc    4772
tttttatgta tcagtgtttg ataaacacag tccttaactg aaggtaaacc aaagcatcac    4832
gttgacatta gaccaaatac ttttgattcc caactactcg tttgttcttt tctcctttt     4892
gtgctttccc atagtgagaa ttttataaa  gacttcttgc ttctctcacc atccatcctt    4952
ctcttttctg cctcttacat gtgaatgttg agcccacaat caacagtggt tttattttt     5012
cctctactca aagttaaaac tgaccaaagt tactggcttt ttactttgct agaacaacaa    5072
actatcttat gtttacatac tggtttacaa tgttatttat gtgcaaattg tcaaaatgta    5132
aattaaaatat aaatgttcat gctttaccaa aat                                5165
```

<210> SEQ ID NO 2
<211> LENGTH: 825
<212> TYPE: PRT
<213> ORGANISM: Homo sapiens

<400> SEQUENCE: 2

```
Met Leu Asp Ile Cys Leu Glu Lys Arg Val Gly Thr Thr Leu Ala Ala
1               5                   10                  15

Pro Lys Cys Asn Ser Ser Thr Val Arg Phe Gln Gly Leu Ala Glu Gly
            20                  25                  30

Thr Lys Gly Thr Met Lys Met Asp Met Glu Asp Ala Asp Met Thr Leu
        35                  40                  45

Trp Thr Glu Ala Glu Phe Glu Glu Lys Cys Thr Tyr Ile Val Asn Asp
    50                  55                  60

His Pro Trp Asp Ser Gly Ala Asp Gly Gly Thr Ser Val Gln Ala Glu
65                  70                  75                  80

Ala Ser Leu Pro Arg Asn Leu Leu Phe Lys Tyr Ala Thr Asn Ser Glu
                85                  90                  95

Glu Val Ile Gly Val Met Ser Lys Tyr Ile Pro Lys Gly Thr Arg
            100                 105                 110

Phe Gly Pro Leu Ile Gly Glu Ile Tyr Thr Asn Asp Thr Val Pro Lys
        115                 120                 125

Asn Ala Asn Arg Lys Tyr Phe Trp Arg Ile Tyr Ser Arg Gly Glu Leu
    130                 135                 140

His His Phe Ile Asp Gly Phe Asn Glu Glu Lys Ser Asn Trp Met Arg
145                 150                 155                 160

Tyr Val Asn Pro Ala His Ser Pro Arg Glu Gln Asn Leu Ala Ala Cys
                165                 170                 175

Gln Asn Gly Met Asn Ile Tyr Phe Tyr Thr Ile Lys Pro Ile Pro Ala
            180                 185                 190

Asn Gln Glu Leu Leu Val Trp Tyr Cys Arg Asp Phe Ala Glu Arg Leu
        195                 200                 205

His Tyr Pro Tyr Pro Gly Glu Leu Thr Met Met Asn Leu Thr Gln Thr
    210                 215                 220

Gln Ser Ser Leu Lys Gln Pro Ser Thr Glu Lys Asn Glu Leu Cys Pro
225                 230                 235                 240

Lys Asn Val Pro Lys Arg Glu Tyr Ser Val Lys Glu Ile Leu Lys Leu
```

```
                245                 250                 255
Asp Ser Asn Pro Ser Lys Gly Lys Asp Leu Tyr Arg Ser Asn Ile Ser
            260                 265                 270

Pro Leu Thr Ser Glu Lys Asp Leu Asp Asp Phe Arg Arg Arg Gly Ser
        275                 280                 285

Pro Glu Met Pro Phe Tyr Pro Arg Val Val Tyr Pro Ile Arg Ala Pro
    290                 295                 300

Leu Pro Glu Asp Phe Leu Lys Ala Ser Leu Ala Tyr Gly Ile Glu Arg
305                 310                 315                 320

Pro Thr Tyr Ile Thr Arg Ser Pro Ile Pro Ser Ser Thr Thr Pro Ser
                325                 330                 335

Pro Ser Ala Arg Ser Ser Pro Asp Gln Ser Leu Lys Ser Ser Ser Pro
            340                 345                 350

His Ser Ser Pro Gly Asn Thr Val Ser Pro Val Gly Pro Gly Ser Gln
        355                 360                 365

Glu His Arg Asp Ser Tyr Ala Tyr Leu Asn Ala Ser Tyr Gly Thr Glu
    370                 375                 380

Gly Leu Gly Ser Tyr Pro Gly Tyr Ala Pro Leu Pro His Leu Pro Pro
385                 390                 395                 400

Ala Phe Ile Pro Ser Tyr Asn Ala His Tyr Pro Lys Phe Leu Leu Pro
                405                 410                 415

Pro Tyr Gly Met Asn Cys Asn Gly Leu Ser Ala Val Ser Ser Met Asn
            420                 425                 430

Gly Ile Asn Asn Phe Gly Leu Phe Pro Arg Leu Cys Pro Val Tyr Ser
        435                 440                 445

Asn Leu Leu Gly Gly Gly Ser Leu Pro His Pro Met Leu Asn Pro Thr
    450                 455                 460

Ser Leu Pro Ser Ser Leu Pro Ser Asp Gly Ala Arg Arg Leu Leu Gln
465                 470                 475                 480

Pro Glu His Pro Arg Glu Val Leu Val Pro Ala Pro His Ser Ala Phe
                485                 490                 495

Ser Phe Thr Gly Ala Ala Ala Ser Met Lys Asp Lys Ala Cys Ser Pro
            500                 505                 510

Thr Ser Gly Ser Pro Thr Ala Gly Thr Ala Thr Ala Glu His Val
        515                 520                 525

Val Gln Pro Lys Ala Thr Ser Ala Ala Met Ala Ala Pro Ser Ser Asp
    530                 535                 540

Glu Ala Met Asn Leu Ile Lys Asn Lys Arg Asn Met Thr Gly Tyr Lys
545                 550                 555                 560

Thr Leu Pro Tyr Pro Leu Lys Lys Gln Asn Gly Lys Ile Lys Tyr Glu
                565                 570                 575

Cys Asn Val Cys Ala Lys Thr Phe Gly Gln Leu Ser Asn Leu Lys Val
            580                 585                 590

His Leu Arg Val His Ser Gly Glu Arg Pro Phe Lys Cys Gln Thr Cys
        595                 600                 605

Asn Lys Gly Phe Thr Gln Leu Ala His Leu Gln Lys His Tyr Leu Val
    610                 615                 620

His Thr Gly Glu Lys Pro His Glu Cys Gln Val Cys His Lys Arg Phe
625                 630                 635                 640

Ser Ser Thr Ser Asn Leu Lys Thr His Leu Arg Leu His Ser Gly Glu
                645                 650                 655

Lys Pro Tyr Gln Cys Lys Val Cys Pro Ala Lys Phe Thr Gln Phe Val
            660                 665                 670
```

```
His Leu Lys Leu His Lys Arg Leu His Thr Arg Glu Arg Pro His Lys
        675                 680                 685
Cys Ser Gln Cys His Lys Asn Tyr Ile His Leu Cys Ser Leu Lys Val
    690                 695                 700
His Leu Lys Gly Asn Cys Ala Ala Pro Ala Pro Gly Leu Pro Leu
705                 710                 715                 720
Glu Asp Leu Thr Arg Ile Asn Glu Glu Ile Glu Lys Phe Asp Ile Ser
                725                 730                 735
Asp Asn Ala Asp Arg Leu Glu Asp Val Glu Asp Ile Ser Val Ile
            740                 745                 750
Ser Val Val Glu Lys Glu Ile Leu Ala Val Val Arg Lys Glu Lys Glu
        755                 760                 765
Glu Thr Gly Leu Lys Val Ser Leu Gln Arg Asn Met Gly Asn Gly Leu
    770                 775                 780
Leu Ser Ser Gly Cys Ser Leu Tyr Glu Ser Ser Asp Leu Pro Leu Met
785                 790                 795                 800
Lys Leu Pro Pro Ser Asn Pro Leu Pro Leu Val Pro Val Lys Val Lys
                805                 810                 815
Gln Glu Thr Val Glu Pro Met Asp Pro
            820                 825

<210> SEQ ID NO 3
<211> LENGTH: 5281
<212> TYPE: DNA
<213> ORGANISM: Mus musculus
<220> FEATURE:
<221> NAME/KEY: CDS
<222> LOCATION: (221)..(2791)

<400> SEQUENCE: 3
gggggaagag tagtcagtcg ctcgctcact cgctcgctcg cacagacact gctgcagtga      60
cactcggccc tccagtgtcg cggagacgca agagcagcgc gcagcacctg tccgcccgga     120
gcgagcccgg cccgcggccg tagaaaagga gggaccgccg aggtgcgcgt cagtactgct     180
cagcccggca gggacgcggg aggatgtgga ctgggtggac atg aga gag gct tat      235
                                              Met Arg Glu Ala Tyr
                                                1               5 ctc aga tgt tgg atc ttc tct tgg aaa aac gtg tgg gta cga cct tgc      283
Leu Arg Cys Trp Ile Phe Ser Trp Lys Asn Val Trp Val Arg Pro Cys
                10                  15                  20 caa agg ctg cat ttt aaa acc gtg ctt ctt caa ggc agt cta ctt tac      331
Gln Arg Leu His Phe Lys Thr Val Leu Leu Gln Gly Ser Leu Leu Tyr
        25                  30                  35 acg gct ttg gac tct tac tca act gta caa gct gcc ccc aag tct agc      379
Thr Ala Leu Asp Ser Tyr Ser Thr Val Gln Ala Ala Pro Lys Ser Ser
    40                  45                  50 tcc ggc tcc gtg aag ttt caa gga ctg gca gag act ggg atc atg aaa      427
Ser Gly Ser Val Lys Phe Gln Gly Leu Ala Glu Thr Gly Ile Met Lys
55                  60                  65 atg gac atg gag gac gct gat atg act ttg tgg aca gag gcc gag ttt      475
Met Asp Met Glu Asp Ala Asp Met Thr Leu Trp Thr Glu Ala Glu Phe
70                  75                  80                  85 gaa gag aag tgt aca tac ata gtg aac gac cac ccc tgg gat tcc ggc      523
Glu Glu Lys Cys Thr Tyr Ile Val Asn Asp His Pro Trp Asp Ser Gly
                90                  95                 100 gct gac ggg ggt act tct gtt caa gcc gag gca tcc tta cca agg aac      571
Ala Asp Gly Gly Thr Ser Val Gln Ala Glu Ala Ser Leu Pro Arg Asn
        105                 110                 115
```

-continued

| | | |
|---|---|---|
| ctg ctt ttc aag tat gct gcc aac aac agc aaa gag gtt att ggc gtg<br>Leu Leu Phe Lys Tyr Ala Ala Asn Asn Ser Lys Glu Val Ile Gly Val<br>120                  125                  130 | 619 |
| gta agt aag gag tac ata ccg aag gga aca cgc ttt gga ccc ctc atc<br>Val Ser Lys Glu Tyr Ile Pro Lys Gly Thr Arg Phe Gly Pro Leu Ile<br>    135                140                145 | 667 |
| ggt gaa gtc tac act aat gac aca gtt ccc aag aat gcc aac agg aag<br>Gly Glu Val Tyr Thr Asn Asp Thr Val Pro Lys Asn Ala Asn Arg Lys<br>150                  155                160              165 | 715 |
| tat ttt tgg cgg atc tat tcc aga gag gag ttc cac cac ttc att gat<br>Tyr Phe Trp Arg Ile Tyr Ser Arg Glu Glu Phe His His Phe Ile Asp<br>              170                175                180 | 763 |
| ggc ttt aat gag gag aaa agc aac tgg atg cgc tac gtg aat cca gct<br>Gly Phe Asn Glu Glu Lys Ser Asn Trp Met Arg Tyr Val Asn Pro Ala<br>                   185                190              195 | 811 |
| cac tct gcc cgg gag caa aac ctg gct gcc tgt cag aac ggg atg aac<br>His Ser Ala Arg Glu Gln Asn Leu Ala Ala Cys Gln Asn Gly Met Asn<br>            200                205                210 | 859 |
| atc tac ttc tac act att aag cct atc cct gcc aac cag gaa ctt ctt<br>Ile Tyr Phe Tyr Thr Ile Lys Pro Ile Pro Ala Asn Gln Glu Leu Leu<br>215                  220                225 | 907 |
| gtg tgg tat tgt cgg gac ttt gcg gag agg ctc cac tac cct tat cct<br>Val Trp Tyr Cys Arg Asp Phe Ala Glu Arg Leu His Tyr Pro Tyr Pro<br>230                  235                240              245 | 955 |
| gga gag ctc aca gtg ata aat ctc aca caa acg gaa agc aac cca aag<br>Gly Glu Leu Thr Val Ile Asn Leu Thr Gln Thr Glu Ser Asn Pro Lys<br>            250                255                260 | 1003 |
| caa tac agt agt gag aaa aat gaa ctc tac cca aag agt gtc ccc aag<br>Gln Tyr Ser Ser Glu Lys Asn Glu Leu Tyr Pro Lys Ser Val Pro Lys<br>                  265                270              275 | 1051 |
| aga gag tac agc gtg aaa gaa att cta aaa ctg gac tcc aat ccc tcc<br>Arg Glu Tyr Ser Val Lys Glu Ile Leu Lys Leu Asp Ser Asn Pro Ser<br>            280                285                290 | 1099 |
| aaa agg aag gac atc tac cgt tcc aac att tca ccc ttc act tta gaa<br>Lys Arg Lys Asp Ile Tyr Arg Ser Asn Ile Ser Pro Phe Thr Leu Glu<br>295                  300                305 | 1147 |
| aag gac atg gat ggc ttt cgg aaa aat ggg agc ccc gac atg ccc ttc<br>Lys Asp Met Asp Gly Phe Arg Lys Asn Gly Ser Pro Asp Met Pro Phe<br>310                  315                320              325 | 1195 |
| tac cct cgg gtg gtt tat cct atc cgg gca cct ctg cca gaa gac ttt<br>Tyr Pro Arg Val Val Tyr Pro Ile Arg Ala Pro Leu Pro Glu Asp Phe<br>            330                335                340 | 1243 |
| ttg aaa gcg tcc ctg gcc tat ggg atg gag aga ccc acc tac ata act<br>Leu Lys Ala Ser Leu Ala Tyr Gly Met Glu Arg Pro Thr Tyr Ile Thr<br>                  345                350              355 | 1291 |
| cac agt ccc ctt ccg tct tcc aca act cca agt ccc cct gcg agc agc<br>His Ser Pro Leu Pro Ser Ser Thr Thr Pro Ser Pro Pro Ala Ser Ser<br>            360                365                370 | 1339 |
| agc ccg gag cag agc ctt aag agc tcc agc ccc cac agc agc ccg gga<br>Ser Pro Glu Gln Ser Leu Lys Ser Ser Ser Pro His Ser Ser Pro Gly<br>375                  380                385 | 1387 |
| aac acg gtg tca ccc ctg gcg cca ggc ctc cca gaa cac cgg gac tcc<br>Asn Thr Val Ser Pro Leu Ala Pro Gly Leu Pro Glu His Arg Asp Ser<br>390                  395                400              405 | 1435 |
| tac tcc tac ttg aat gtt tcc tat ggt tcc gag ggc ctg ggc tcc tac<br>Tyr Ser Tyr Leu Asn Val Ser Tyr Gly Ser Glu Gly Leu Gly Ser Tyr<br>            410                415              420 | 1483 |
| cct ggc tat gca cct gcc ccc cac ctc cca cca gct ttc att cct tct<br>Pro Gly Tyr Ala Pro Ala Pro His Leu Pro Pro Ala Phe Ile Pro Ser | 1531 |

-continued

```
             425                 430                 435
tac aat gct cac tac ccc aag ttc ctg ttg cca ccg tac ggc att agt       1579
Tyr Asn Ala His Tyr Pro Lys Phe Leu Leu Pro Pro Tyr Gly Ile Ser
        440                 445                 450 tcc aat ggc ttg agc acc atg aac aac atc aat ggt atc aac aac ttc       1627
Ser Asn Gly Leu Ser Thr Met Asn Asn Ile Asn Gly Ile Asn Asn Phe
455                 460                 465 agc ctc ttc cct agg ttg tat ccc gtc tac agt aac ctc ctt agt ggc       1675
Ser Leu Phe Pro Arg Leu Tyr Pro Val Tyr Ser Asn Leu Leu Ser Gly
470                 475                 480                 485 agc agc ctg cct cat ccc atg ctc aat cca gct tcc cta ccg agt tcc       1723
Ser Ser Leu Pro His Pro Met Leu Asn Pro Ala Ser Leu Pro Ser Ser
                490                 495                 500 ctg cct acc gat gga gcc cgg agg ctg ctt cca ccg gag cac ccc aaa       1771
Leu Pro Thr Asp Gly Ala Arg Arg Leu Leu Pro Pro Glu His Pro Lys
            505                 510                 515 gag gtg ctt atc cca gca ccc cac agt gcc ttc tcc ctt acc ggg gct       1819
Glu Val Leu Ile Pro Ala Pro His Ser Ala Phe Ser Leu Thr Gly Ala
        520                 525                 530 gca gcc agc atg aag gac gag agt agt ccc ccc agc gga tct cca acg       1867
Ala Ala Ser Met Lys Asp Glu Ser Ser Pro Pro Ser Gly Ser Pro Thr
535                 540                 545 gcg gga act gca gcc acg tca gaa cac gtg gta caa ccc aaa gct acc       1915
Ala Gly Thr Ala Ala Thr Ser Glu His Val Val Gln Pro Lys Ala Thr
550                 555                 560                 565 tca tca gtg atg gcg gcc ccc agc act gac gga gcc atg aat ctc att       1963
Ser Ser Val Met Ala Ala Pro Ser Thr Asp Gly Ala Met Asn Leu Ile
                570                 575                 580 aaa aac aaa cga aac atg act ggt tac aag act ctt cct tac cct ctg       2011
Lys Asn Lys Arg Asn Met Thr Gly Tyr Lys Thr Leu Pro Tyr Pro Leu
            585                 590                 595 aag aaa cag aat ggc aag atc aag tat gag tgc aat gtc tgt gcc aag       2059
Lys Lys Gln Asn Gly Lys Ile Lys Tyr Glu Cys Asn Val Cys Ala Lys
        600                 605                 610 acg ttc ggt cag ctc tcc aac ctg aag gtc cac ctg aga gtg cac agt       2107
Thr Phe Gly Gln Leu Ser Asn Leu Lys Val His Leu Arg Val His Ser
615                 620                 625 gga gaa cgg cct ttc aag tgc cag acc tgc aac aag ggt ttt act cag       2155
Gly Glu Arg Pro Phe Lys Cys Gln Thr Cys Asn Lys Gly Phe Thr Gln
630                 635                 640                 645 ctc gcc cac ctg cag aaa cac tac ttg gta cac aca gga gag aag cca       2203
Leu Ala His Leu Gln Lys His Tyr Leu Val His Thr Gly Glu Lys Pro
                650                 655                 660 cat gag tgc cag gtc tgc cac aag aga ttt agc agc aca agc aat ctc       2251
His Glu Cys Gln Val Cys His Lys Arg Phe Ser Ser Thr Ser Asn Leu
            665                 670                 675 aag acc cac ctt cga ttg cat tct gga gaa aaa cct tac caa tgt aag       2299
Lys Thr His Leu Arg Leu His Ser Gly Glu Lys Pro Tyr Gln Cys Lys
        680                 685                 690 gtg tgc cct gcc aag ttt acg caa ttt gtg cac ctg aag ctg cac aag       2347
Val Cys Pro Ala Lys Phe Thr Gln Phe Val His Leu Lys Leu His Lys
695                 700                 705 cga ctg cat acc cgg gag cgg cct cac aag tgt gcc cag tgt cac aag       2395
Arg Leu His Thr Arg Glu Arg Pro His Lys Cys Ala Gln Cys His Lys
710                 715                 720                 725 agc tac atc cat ctc tgc agc ctc aag gtc cac ctg aag ggc aac tgc       2443
Ser Tyr Ile His Leu Cys Ser Leu Lys Val His Leu Lys Gly Asn Cys
                730                 735                 740 cct gcg ggc cca gct gct ggg ctg cct ttg gag gat ctg acc cga atc       2491
```

```
                Pro Ala Gly Pro Ala Ala Gly Leu Pro Leu Glu Asp Leu Thr Arg Ile
                            745                 750                 755 aat gaa gaa att gag agg ttc gac atc agc gac aat gca gac cgt ctt          2539
Asn Glu Glu Ile Glu Arg Phe Asp Ile Ser Asp Asn Ala Asp Arg Leu
        760                 765                 770 gag gac atg gag gac agt gtc gat gtg acc tcc atg gtg gag aag gag          2587
Glu Asp Met Glu Asp Ser Val Asp Val Thr Ser Met Val Glu Lys Glu
    775                 780                 785 att cta gct gtg gtc aga aaa gag aaa gaa gaa acc agt ctg aaa gtg          2635
Ile Leu Ala Val Val Arg Lys Glu Lys Glu Glu Thr Ser Leu Lys Val
790                 795                 800                 805 tct ttg caa aga aac atg ggg aac ggc ctc ctc tcc tca ggg tgc agc          2683
Ser Leu Gln Arg Asn Met Gly Asn Gly Leu Leu Ser Ser Gly Cys Ser
                810                 815                 820 ctc tat gag tca tcg gac ctg tcc ctc atg aag ttg cct cac agc aac          2731
Leu Tyr Glu Ser Ser Asp Leu Ser Leu Met Lys Leu Pro His Ser Asn
            825                 830                 835 cca cta cct ctg gtg cct gta aag gtc aaa caa gaa aca gtt gaa ccg          2779
Pro Leu Pro Leu Val Pro Val Lys Val Lys Gln Glu Thr Val Glu Pro
        840                 845                 850 atg gat cct taa gattttcaga aataagtgt ttcgtgttgc ttcttagggt               2831
Met Asp Pro
    855 atggcttggt gaatcagggt gcctttagca aattgcttgt acatgactcc agatctgcaa        2891 agctccgctg gcaccgggtg cttccctgca cctctctgga attaaagaag gactccaatg        2951 ttaccaaaat ctcagggcat aaatgaggca aagactcact atatacat atatacatat          3011 atacatatta taaatatata tatacttatt tacagccatg tctatatatt tgaacctgtg        3071 tattttgaat atttgtgtgg atatgtttgc atagcgcctt cctattacta aaactattgc        3131 ctagccataa ttatttttc aatgataatt cttcataatt tattatacag tttatctttc         3191 aaaaagcaat aattaaagaa gtttacaatg actggaaaga ttctttgtaa tttgagtata        3251 aatgttgtat ctttgtcctg tggccattct ttgtagataa tttctgcaca tctgtttaaa        3311 tgcctgagac ttagaagata gctctgtgat ttcaggcaac cttttctctat gataatgctt       3371 taaaatgagg ttttgatatt gccaaagtca tgtggttggt gtgttaactc agaagatcac        3431 acaatctgag tgacattctc taagttgggg atacatgtgc agaattgctc agcaataatt        3491 tgaggggaag gaagaagaaa aatatttat gtttcagaat gatggtttgg ttttcctcct         3551 cctagtcaca attttaccaa acagtgacag gaaggctttg ccaacctgtc tcccaatgtc        3611 acatgaccat tctgagtggc catatgactt tggcatccct gggtgttatc tgaaaatgtg        3671 aagaagataa aaaagccgtg ttcagaagat ctgtcgtaaa gcacagatgt tgtgtgtgtg        3731 tgtgtgtggg ttgggggtt tgagtctggc tgtcattttg ctgttggctt gttttttgttt        3791 ttttaatatc aaaattgcac aaagctggtg ccctaccaag aaggatttga tatagaaagg        3851 ctcaggccac acttaaaata caagcaagca aagagaacag aaaaaaataa aagtaaaaac        3911 gggtattctt atcatcttag gttaagcggg taatgaacat tcctgtcccc aacgcatcaa        3971 ctgtattgta tctgtaaaac tcagcttttc tcagtatttg tgttttttgca ttgtataatt       4031 aacttaatta aagatgaaag ggcattgcaa agtgttcaa caattacctc attgagtgta         4091 tccagtagga gtgcaggaat taatgtcgta tctcatgagt tgctacccag ctgagcgtgt        4151 gtgcttccaa atggtaggct gggtggttcg gtcctgtatt tcctaagcc caaaggttac         4211 ctgttggtgt tcaaggtgta ataaagaatg ctgtatattt atgaacctat ttataccagt        4271
```

-continued

```
ataccatgtg tatatatgat atatttataa ccacttaaat tgtgagccaa gccatgtaaa    4331
agaacctatt tttcctaaga gcaaaaagaa tctctctgaa gttttgctta aaactccatg    4391
acctcgctat gactttggtg cttgggcacc accctgccta ctaccagaga gcagagcacc    4451
tcagtgcaga ggtgagggtg tgtagcatct tgggatggat agaaacacca caccatccag    4511
tcgcatttga tggccttgct acatgtgtgt cagttgggtc acagaataaa aatcattttt    4571
ctatttctgc tctcctcttc ctcttcctct tcttcttcct ctttctctcc ctcctctaga    4631
accctgactc atgctcactg ctcagtctga tgcttacctt agagttttgt atatatagat    4691
caacttacaa agagggaaaa cttcagatcc tctgggggaa acccaagagc cttactgacc    4751
tgttgctgtg actagctaga tgggtttctc tttaccttcc aaggatcaaa accagagatt    4811
ccacacatgc tagcaagcaa gcaagctgtc actgggctgc agccccaaca agactgacat    4871
ttctggatgc atctgtattt gagaaaaata ctcacttaat tgtaggttaa ccaaagcatg    4931
acctgacatt gacaccaaat acaaatacga tttctttgca gtgaacttgg gttgttttcc    4991
tcctgtgctt ttcttgtgtt gggaggattt ttacaaggac aattgctttt cttgccatct    5051
gtcttcctct taggcctctt acatgagagt gttgagccca caatgaacag tggttggttg    5111
gttggttggt tggtttgttt gtttgttttt tcctcagagt taaaactgac caaagttatt    5171 ggcttttttac tttgctagaa caacaaacta tcttatgttt acgtactggt ttacattgtt    5231
atttatgtgc aaattgtcaa aatgtaaatt aaaatataaa tgttcatgct               5281
```

<210> SEQ ID NO 4
<211> LENGTH: 856
<212> TYPE: PRT
<213> ORGANISM: Mus musculus

<400> SEQUENCE: 4

```
Met Arg Glu Ala Tyr Leu Arg Cys Trp Ile Phe Ser Trp Lys Asn Val
1               5                   10                  15

Trp Val Arg Pro Cys Gln Arg Leu His Phe Lys Thr Val Leu Leu Gln
            20                  25                  30

Gly Ser Leu Leu Tyr Thr Ala Leu Asp Ser Tyr Ser Thr Val Gln Ala
        35                  40                  45

Ala Pro Lys Ser Ser Ser Gly Ser Val Lys Phe Gln Gly Leu Ala Glu
    50                  55                  60

Thr Gly Ile Met Lys Met Asp Met Glu Asp Ala Asp Met Thr Leu Trp
65                  70                  75                  80

Thr Glu Ala Glu Phe Glu Glu Lys Cys Thr Tyr Ile Val Asn Asp His
                85                  90                  95

Pro Trp Asp Ser Gly Ala Asp Gly Gly Thr Ser Val Gln Ala Glu Ala
            100                 105                 110

Ser Leu Pro Arg Asn Leu Leu Phe Lys Tyr Ala Ala Asn Asn Ser Lys
        115                 120                 125

Glu Val Ile Gly Val Val Ser Lys Glu Tyr Ile Pro Lys Gly Thr Arg
    130                 135                 140

Phe Gly Pro Leu Ile Gly Glu Val Tyr Thr Asn Asp Thr Val Pro Lys
145                 150                 155                 160

Asn Ala Asn Arg Lys Tyr Phe Trp Arg Ile Tyr Ser Arg Glu Glu Phe
                165                 170                 175

His His Phe Ile Asp Gly Phe Asn Glu Glu Lys Ser Asn Trp Met Arg
            180                 185                 190

Tyr Val Asn Pro Ala His Ser Ala Arg Glu Gln Asn Leu Ala Ala Cys
```

```
                195                 200                 205
Gln Asn Gly Met Asn Ile Tyr Phe Tyr Thr Ile Lys Pro Ile Pro Ala
210                 215                 220

Asn Gln Glu Leu Leu Val Trp Tyr Cys Arg Asp Phe Ala Glu Arg Leu
225                 230                 235                 240

His Tyr Pro Tyr Pro Gly Glu Leu Thr Val Ile Asn Leu Thr Gln Thr
                245                 250                 255

Glu Ser Asn Pro Lys Gln Tyr Ser Ser Glu Lys Asn Glu Leu Tyr Pro
                260                 265                 270

Lys Ser Val Pro Lys Arg Glu Tyr Ser Val Lys Glu Ile Leu Lys Leu
            275                 280                 285

Asp Ser Asn Pro Ser Lys Arg Lys Asp Ile Tyr Arg Ser Asn Ile Ser
290                 295                 300

Pro Phe Thr Leu Glu Lys Asp Met Asp Gly Phe Arg Lys Asn Gly Ser
305                 310                 315                 320

Pro Asp Met Pro Phe Tyr Pro Arg Val Val Tyr Pro Ile Arg Ala Pro
                325                 330                 335

Leu Pro Glu Asp Phe Leu Lys Ala Ser Leu Ala Tyr Gly Met Glu Arg
                340                 345                 350

Pro Thr Tyr Ile Thr His Ser Pro Leu Pro Ser Ser Thr Thr Pro Ser
            355                 360                 365

Pro Pro Ala Ser Ser Ser Pro Glu Gln Ser Leu Lys Ser Ser Ser Pro
370                 375                 380

His Ser Ser Pro Gly Asn Thr Val Ser Pro Leu Ala Pro Gly Leu Pro
385                 390                 395                 400

Glu His Arg Asp Ser Tyr Ser Tyr Leu Asn Val Ser Tyr Gly Ser Glu
                405                 410                 415

Gly Leu Gly Ser Tyr Pro Gly Tyr Ala Pro Ala Pro His Leu Pro Pro
                420                 425                 430

Ala Phe Ile Pro Ser Tyr Asn Ala His Tyr Pro Lys Phe Leu Leu Pro
            435                 440                 445

Pro Tyr Gly Ile Ser Ser Asn Gly Leu Ser Thr Met Asn Asn Ile Asn
450                 455                 460

Gly Ile Asn Asn Phe Ser Leu Phe Pro Arg Leu Tyr Pro Val Tyr Ser
465                 470                 475                 480

Asn Leu Leu Ser Gly Ser Ser Leu Pro His Pro Met Leu Asn Pro Ala
                485                 490                 495

Ser Leu Pro Ser Ser Leu Pro Thr Asp Gly Ala Arg Arg Leu Leu Pro
                500                 505                 510

Pro Glu His Pro Lys Glu Val Leu Ile Pro Ala Pro His Ser Ala Phe
            515                 520                 525

Ser Leu Thr Gly Ala Ala Ala Ser Met Lys Asp Glu Ser Ser Pro Pro
530                 535                 540

Ser Gly Ser Pro Thr Ala Gly Thr Ala Ala Thr Ser Glu His Val Val
545                 550                 555                 560

Gln Pro Lys Ala Thr Ser Ser Val Met Ala Ala Pro Ser Thr Asp Gly
                565                 570                 575

Ala Met Asn Leu Ile Lys Asn Lys Arg Asn Met Thr Gly Tyr Lys Thr
                580                 585                 590

Leu Pro Tyr Pro Leu Lys Lys Gln Asn Gly Lys Ile Lys Tyr Glu Cys
            595                 600                 605

Asn Val Cys Ala Lys Thr Phe Gly Gln Leu Ser Asn Leu Lys Val His
610                 615                 620
```

```
Leu Arg Val His Ser Gly Glu Arg Pro Phe Lys Cys Gln Thr Cys Asn
625                 630                 635                 640

Lys Gly Phe Thr Gln Leu Ala His Leu Gln Lys His Tyr Leu Val His
            645                 650                 655

Thr Gly Glu Lys Pro His Glu Cys Gln Val Cys His Lys Arg Phe Ser
        660                 665                 670

Ser Thr Ser Asn Leu Lys Thr His Leu Arg Leu His Ser Gly Glu Lys
    675                 680                 685

Pro Tyr Gln Cys Lys Val Cys Pro Ala Lys Phe Thr Gln Phe Val His
690                 695                 700

Leu Lys Leu His Lys Arg Leu His Thr Arg Glu Arg Pro His Lys Cys
705                 710                 715                 720

Ala Gln Cys His Lys Ser Tyr Ile His Leu Cys Ser Leu Lys Val His
                725                 730                 735

Leu Lys Gly Asn Cys Pro Ala Gly Pro Ala Ala Gly Leu Pro Leu Glu
            740                 745                 750

Asp Leu Thr Arg Ile Asn Glu Glu Ile Glu Arg Phe Asp Ile Ser Asp
        755                 760                 765

Asn Ala Asp Arg Leu Glu Asp Met Glu Asp Ser Val Asp Val Thr Ser
    770                 775                 780

Met Val Glu Lys Glu Ile Leu Ala Val Val Arg Lys Glu Lys Glu Glu
785                 790                 795                 800

Thr Ser Leu Lys Val Ser Leu Gln Arg Asn Met Gly Asn Gly Leu Leu
                805                 810                 815

Ser Ser Gly Cys Ser Leu Tyr Glu Ser Ser Asp Leu Ser Leu Met Lys
            820                 825                 830

Leu Pro His Ser Asn Pro Leu Pro Leu Val Pro Val Lys Val Lys Gln
        835                 840                 845

Glu Thr Val Glu Pro Met Asp Pro
    850                 855

<210> SEQ ID NO 5
<211> LENGTH: 2344
<212> TYPE: DNA
<213> ORGANISM: Homo sapiens
<220> FEATURE:
<221> NAME/KEY: CDS
<222> LOCATION: (203)..(1918)

<400> SEQUENCE: 5
aattccctac cctcgacctg tcgatgcccc gcggccccgc ccgccctctt aagcctggct      60
cagccctcag ggcccgcccg aagtctaccg agcccgagtg gcctaccgag cccgagtggc     120
cccgcagcgt ccaggaggcg cccgctccgc ggtggcgctc ttggaggtgg tgtcggagag     180
ccgccgagcg tgcggtcccg gg atg gct cta ccc cgg cca agt gag gcc gtg     232
                           Met Ala Leu Pro Arg Pro Ser Glu Ala Val
                             1               5                  10 cct cag gac aag gtg tgc tac ccg ccg gag agc agc ccg cag aac ctg     280
Pro Gln Asp Lys Val Cys Tyr Pro Pro Glu Ser Ser Pro Gln Asn Leu
                15                  20                  25 gcc gcg tac tac acg cct ttc ccg tcc tat gga cac tac aga aac agc     328
Ala Ala Tyr Tyr Thr Pro Phe Pro Ser Tyr Gly His Tyr Arg Asn Ser
            30                  35                  40 ctg gcc acc gtg gag gaa gac ttc caa cct ttc cgg cag ctg gag gcc     376
Leu Ala Thr Val Glu Glu Asp Phe Gln Pro Phe Arg Gln Leu Glu Ala
        45                  50                  55
```

-continued

| | | |
|---|---|---|
| gca gcg tct gct gcc ccc gcc atg ccc ccc ttc ccc ttc cgg atg gcg<br>Ala Ala Ser Ala Ala Pro Ala Met Pro Pro Phe Pro Phe Arg Met Ala<br>60                                65                             70 | 424 |
| cct ccc ttg ctg agc ccg ggt ctg ggc cta cag agg gag cct ctc tac<br>Pro Pro Leu Leu Ser Pro Gly Leu Gly Leu Gln Arg Glu Pro Leu Tyr<br>75                                80                           85                           90 | 472 |
| gat ctg ccc tgg tac agc aag ctg cca ccg tgg tac cca att ccc cac<br>Asp Leu Pro Trp Tyr Ser Lys Leu Pro Pro Trp Tyr Pro Ile Pro His<br>                            95                             100                          105 | 520 |
| gtc ccc agg gaa gtg ccg ccc ttc ctg agc agc agc cac gag tac gcg<br>Val Pro Arg Glu Val Pro Pro Phe Leu Ser Ser Ser His Glu Tyr Ala<br>             110                             115                          120 | 568 |
| ggt gcc agc agt gaa gat ctg ggc cac caa atc att ggt ggc gac aac<br>Gly Ala Ser Ser Glu Asp Leu Gly His Gln Ile Ile Gly Gly Asp Asn<br>125                               130                           135 | 616 |
| gag agt ggc ccg tgt tgt gga cct gac act tta att cca ccg ccc cct<br>Glu Ser Gly Pro Cys Cys Gly Pro Asp Thr Leu Ile Pro Pro Pro Pro<br>       140                            145                          150 | 664 |
| gcg gat gct tct ctg tta cct gag ggg ctg agg acc tcc cag tta tta<br>Ala Asp Ala Ser Leu Leu Pro Glu Gly Leu Arg Thr Ser Gln Leu Leu<br>155                               160                           165                         170 | 712 |
| cct tgc tca ccc agc aag cag tca gag gat ggt ccc aaa ccc tcc aac<br>Pro Cys Ser Pro Ser Lys Gln Ser Glu Asp Gly Pro Lys Pro Ser Asn<br>               175                           180                          185 | 760 |
| caa gaa ggg aag tcc cct gct cgg ttc cag ttc acg gag gag gac ctg<br>Gln Glu Gly Lys Ser Pro Ala Arg Phe Gln Phe Thr Glu Glu Asp Leu<br>             190                           195                          200 | 808 |
| cac ttc gtt ctg tac ggg gtc act ccc agc ctg gag cac cca gcc agc<br>His Phe Val Leu Tyr Gly Val Thr Pro Ser Leu Glu His Pro Ala Ser<br>                   205                           210                          215 | 856 |
| ctg cac cat gcg att tca ggc ctc ctg gtc ccc cca gac agc tct gga<br>Leu His His Ala Ile Ser Gly Leu Leu Val Pro Pro Asp Ser Ser Gly<br>220                               225                           230 | 904 |
| tct gat tct ctt cct caa act ctg gat aaa gac tcc ctt caa ctt cca<br>Ser Asp Ser Leu Pro Gln Thr Leu Asp Lys Asp Ser Leu Gln Leu Pro<br>235                               240                           245                         250 | 952 |
| gaa ggt cta tgc ctc atg cag acg gtg ttt ggt gaa gtc cca cat ttt<br>Glu Gly Leu Cys Leu Met Gln Thr Val Phe Gly Glu Val Pro His Phe<br>                   255                           260                          265 | 1000 |
| ggt gtg ttc tgc agt agt ttt atc gcc aaa gga gtc agg ttt ggg ccc<br>Gly Val Phe Cys Ser Ser Phe Ile Ala Lys Gly Val Arg Phe Gly Pro<br>                   270                           275                          280 | 1048 |
| ttt caa ggt aaa gtg gtc aat gcc agt gaa gtg aag acc tac gga gac<br>Phe Gln Gly Lys Val Val Asn Ala Ser Glu Val Lys Thr Tyr Gly Asp<br>285                               290                           295 | 1096 |
| aat tct gtg atg tgg gag atc ttt gaa gat ggt cat ttg agc cac ttt<br>Asn Ser Val Met Trp Glu Ile Phe Glu Asp Gly His Leu Ser His Phe<br>       300                            305                          310 | 1144 |
| ata gat gga aaa gga ggt acg ggg aac tgg atg tcc tat gtc aac tgt<br>Ile Asp Gly Lys Gly Gly Thr Gly Asn Trp Met Ser Tyr Val Asn Cys<br>315                               320                           325                         330 | 1192 |
| gcc cgc ttc ccc aag gag cag aac cta gtt gct gtg cag tgt caa ggg<br>Ala Arg Phe Pro Lys Glu Gln Asn Leu Val Ala Val Gln Cys Gln Gly<br>                   335                           340                          345 | 1240 |
| cat ata ttt tat gag agc tgc aaa gag atc cat cag aac caa gag ctc<br>His Ile Phe Tyr Glu Ser Cys Lys Glu Ile His Gln Asn Gln Glu Leu<br>                   350                           355                          360 | 1288 |
| ctt gtg tgg tat gga gac tgc tat gag aaa ttt ctg gat att cct gtg<br>Leu Val Trp Tyr Gly Asp Cys Tyr Glu Lys Phe Leu Asp Ile Pro Val<br>365                               370                           375 | 1336 |

```
agc ctt cag gtc aca gag ccg ggg aag cag cca tct ggg ccc tct gaa    1384
Ser Leu Gln Val Thr Glu Pro Gly Lys Gln Pro Ser Gly Pro Ser Glu
    380                 385                 390 gag tct gca gaa ggc tac aga tgt gaa aga tgt ggg aag gta ttt acc    1432
Glu Ser Ala Glu Gly Tyr Arg Cys Glu Arg Cys Gly Lys Val Phe Thr
395                 400                 405                 410 tac aaa tat tac aga gat aag cac ctc aag tac acc ccc tgt gtg gac    1480
Tyr Lys Tyr Tyr Arg Asp Lys His Leu Lys Tyr Thr Pro Cys Val Asp
                415                 420                 425 aag ggc gat agg aaa ttt ccc tgt tct ctc tgc aaa cga tcc ttt gag    1528
Lys Gly Asp Arg Lys Phe Pro Cys Ser Leu Cys Lys Arg Ser Phe Glu
            430                 435                 440 aag cgg gac cgg ctt cgg atc cac att ctt cat gtt cat gag aag cac    1576
Lys Arg Asp Arg Leu Arg Ile His Ile Leu His Val His Glu Lys His
        445                 450                 455 cgg cct cac aag tgt tct aca tgt ggg aaa tgt ttc tct caa tct tcc    1624
Arg Pro His Lys Cys Ser Thr Cys Gly Lys Cys Phe Ser Gln Ser Ser
    460                 465                 470 agc cta aac aaa cac atg cga gtc cac tct gga gac aga cca tac cag    1672
Ser Leu Asn Lys His Met Arg Val His Ser Gly Asp Arg Pro Tyr Gln
475                 480                 485                 490 tgt gtg tat tgt act aag agg ttc aca gcc tcc agc ata ctc cgc aca    1720
Cys Val Tyr Cys Thr Lys Arg Phe Thr Ala Ser Ser Ile Leu Arg Thr
                495                 500                 505 cac atc agg cag cac tcc ggg gag aag ccc ttc aaa tgc aag tac tgt    1768
His Ile Arg Gln His Ser Gly Glu Lys Pro Phe Lys Cys Lys Tyr Cys
            510                 515                 520 ggt aaa tct ttt gca tcc cat gct gcc cat gac agc cat gtc cgg cgt    1816
Gly Lys Ser Phe Ala Ser His Ala Ala His Asp Ser His Val Arg Arg
        525                 530                 535 tca cac aag gag gat gat ggc tgc tca tgc agc atc tgt ggg aaa atc    1864
Ser His Lys Glu Asp Asp Gly Cys Ser Cys Ser Ile Cys Gly Lys Ile
    540                 545                 550 ttc tca gat caa gaa aca ttc tac tcc cac atg aag ttt cat gaa gac    1912
Phe Ser Asp Gln Glu Thr Phe Tyr Ser His Met Lys Phe His Glu Asp
555                 560                 565                 570 tac tag ccctgccagg cacaatgact cacgcctgta atcccagcac tttgggaggc    1968
Tyr agaggtgggt ggatcactca agtccaggag ttcgagacca gcctgggcaa catggtgaaa    2028
tcctgtctct accaaaaaaa tacaaaaatc agctgggggt ggtggcacat gcctgtggtt    2088
ccagccactc aggaggtcga ggtggcagga tggtttgagc acaggagacg gaggttgctg    2148
tgagctgaga tcgccccact gcttttcaac ctgggtgaca gaaccagacc ctgtctcaaa    2208
acaaaacaaa acaaaaaaaa tgagtagccc tcaagagtgt ggagacaatg taaaaacaag    2268
agattcggat tctctctatt tccttttatg ggttatagaa gtccctgcag ttggctgtgt    2328
gtggtggctc acgcct    2344

<210> SEQ ID NO 6
<211> LENGTH: 571
<212> TYPE: PRT
<213> ORGANISM: Homo sapiens

<400> SEQUENCE: 6

Met Ala Leu Pro Arg Pro Ser Glu Ala Val Pro Gln Asp Lys Val Cys
1               5                   10                  15

Tyr Pro Pro Glu Ser Ser Pro Gln Asn Leu Ala Ala Tyr Tyr Thr Pro
            20                  25                  30
```

```
Phe Pro Ser Tyr Gly His Tyr Arg Asn Ser Leu Ala Thr Val Glu Glu
            35                  40                  45

Asp Phe Gln Pro Phe Arg Gln Leu Glu Ala Ala Ser Ala Ala Pro
    50                  55                  60

Ala Met Pro Pro Phe Pro Phe Arg Met Ala Pro Pro Leu Leu Ser Pro
65                  70                  75                  80

Gly Leu Gly Leu Gln Arg Glu Pro Leu Tyr Asp Leu Pro Trp Tyr Ser
                85                  90                  95

Lys Leu Pro Pro Trp Tyr Pro Ile Pro His Val Pro Arg Glu Val Pro
                100                 105                 110

Pro Phe Leu Ser Ser His Glu Tyr Ala Gly Ala Ser Ser Glu Asp
        115                 120                 125

Leu Gly His Gln Ile Ile Gly Gly Asp Asn Glu Ser Gly Pro Cys Cys
    130                 135                 140

Gly Pro Asp Thr Leu Ile Pro Pro Pro Ala Asp Ala Ser Leu Leu
145                 150                 155                 160

Pro Glu Gly Leu Arg Thr Ser Gln Leu Leu Pro Cys Ser Pro Ser Lys
                165                 170                 175

Gln Ser Glu Asp Gly Pro Lys Pro Ser Asn Gln Glu Gly Lys Ser Pro
                180                 185                 190

Ala Arg Phe Gln Phe Thr Glu Glu Asp Leu His Phe Val Leu Tyr Gly
                195                 200                 205

Val Thr Pro Ser Leu Glu His Pro Ala Ser Leu His Ala Ile Ser
    210                 215                 220

Gly Leu Leu Val Pro Pro Asp Ser Ser Gly Ser Asp Ser Leu Pro Gln
225                 230                 235                 240

Thr Leu Asp Lys Asp Ser Leu Gln Leu Pro Glu Gly Leu Cys Leu Met
                245                 250                 255

Gln Thr Val Phe Gly Glu Val Pro His Phe Gly Val Phe Cys Ser Ser
                260                 265                 270

Phe Ile Ala Lys Gly Val Arg Phe Gly Pro Phe Gln Gly Lys Val Val
            275                 280                 285

Asn Ala Ser Glu Val Lys Thr Tyr Gly Asp Asn Ser Val Met Trp Glu
    290                 295                 300

Ile Phe Glu Asp Gly His Leu Ser His Phe Ile Asp Gly Lys Gly Gly
305                 310                 315                 320

Thr Gly Asn Trp Met Ser Tyr Val Asn Cys Ala Arg Phe Pro Lys Glu
                325                 330                 335

Gln Asn Leu Val Ala Val Gln Cys Gln Gly His Ile Phe Tyr Glu Ser
            340                 345                 350

Cys Lys Glu Ile His Gln Asn Gln Glu Leu Leu Val Trp Tyr Gly Asp
    355                 360                 365

Cys Tyr Glu Lys Phe Leu Asp Ile Pro Val Ser Leu Gln Val Thr Glu
    370                 375                 380

Pro Gly Lys Gln Pro Ser Gly Pro Ser Glu Glu Ser Ala Glu Gly Tyr
385                 390                 395                 400

Arg Cys Glu Arg Cys Gly Lys Val Phe Thr Tyr Lys Tyr Tyr Arg Asp
                405                 410                 415

Lys His Leu Lys Tyr Thr Pro Cys Val Asp Lys Gly Asp Arg Lys Phe
            420                 425                 430

Pro Cys Ser Leu Cys Lys Arg Ser Phe Glu Lys Arg Asp Arg Leu Arg
            435                 440                 445
```

```
Ile His Ile Leu His Val His Glu Lys His Arg Pro His Lys Cys Ser
            450                 455                 460
Thr Cys Gly Lys Cys Phe Ser Gln Ser Ser Leu Asn Lys His Met
465                 470                 475                 480
Arg Val His Ser Gly Asp Arg Pro Tyr Gln Cys Val Tyr Cys Thr Lys
                485                 490                 495
Arg Phe Thr Ala Ser Ser Ile Leu Arg Thr His Ile Arg Gln His Ser
                500                 505                 510
Gly Glu Lys Pro Phe Lys Cys Lys Tyr Cys Gly Lys Ser Phe Ala Ser
                515                 520                 525
His Ala Ala His Asp Ser His Val Arg Arg Ser His Lys Glu Asp Asp
                530                 535                 540
Gly Cys Ser Cys Ser Ile Cys Gly Lys Ile Phe Ser Asp Gln Glu Thr
545                 550                 555                 560
Phe Tyr Ser His Met Lys Phe His Glu Asp Tyr
                565                 570
```

```
<210> SEQ ID NO 7
<211> LENGTH: 2596
<212> TYPE: DNA
<213> ORGANISM: Mus musculus
<220> FEATURE:
<221> NAME/KEY: CDS
<222> LOCATION: (76)..(1764)

<400> SEQUENCE: 7
tcagaagtct agggtcccga gacccagcgg gtgccgccct agccttggcc tgagatccgc      60
aaaactcagc ttgcg atg gcc tta ccg ccc tct ggt gag acc cag tcc cag     111
                Met Ala Leu Pro Pro Ser Gly Glu Thr Gln Ser Gln
                  1               5                  10 gac aag gcg aac tac ctg ccc cag agc aac cct cac cac ctg act acc     159
Asp Lys Ala Asn Tyr Leu Pro Gln Ser Asn Pro His His Leu Thr Thr
             15                  20                  25 tac tac gcg cat gcc cca ggc tac agt cac ttt agg aac ctc gcc acc     207
Tyr Tyr Ala His Ala Pro Gly Tyr Ser His Phe Arg Asn Leu Ala Thr
 30                  35                  40 acc gag gag gag ttt caa cct tgg aaa ctg gca gct gca gtg ctt gag     255
Thr Glu Glu Glu Phe Gln Pro Trp Lys Leu Ala Ala Ala Val Leu Glu
 45                  50                  55                  60 tcc cag gcg atg gcc cct ctt gat gct ttt cgg atg act gct ccc ttg     303
Ser Gln Ala Met Ala Pro Leu Asp Ala Phe Arg Met Thr Ala Pro Leu
                 65                  70                  75 ttg aac ccg ggt ctg gct gtt cag agc gag ccg ctc tac aat ctg ccc     351
Leu Asn Pro Gly Leu Ala Val Gln Ser Glu Pro Leu Tyr Asn Leu Pro
             80                  85                  90 tgg tac aaa ttg tca cca tgg aac cga att cct caa ttc act ccc gaa     399
Trp Tyr Lys Leu Ser Pro Trp Asn Arg Ile Pro Gln Phe Thr Pro Glu
         95                 100                 105 gta cca cga ttt cta gac agc act gag cat agg agc agc ggt tcc agc     447
Val Pro Arg Phe Leu Asp Ser Thr Glu His Arg Ser Ser Gly Ser Ser
    110                 115                 120 aac caa aat ttg gtc ctc ggc ggc ggt ggc caa atc agt ggt cag         495
Asn Gln Asn Leu Val Leu Gly Gly Gly Gly Gln Ile Ser Gly Gln
125                 130                 135                 140 agg tgg gaa gct gaa aat tta ctt ctg cca tcc ccg gta att gct tcc     543
Arg Trp Glu Ala Glu Asn Leu Leu Leu Pro Ser Pro Val Ile Ala Ser
                145                 150                 155 cta cta cct gat gga att aag tcg tcc cag tca ata tct gtc ccc caa     591
Leu Leu Pro Asp Gly Ile Lys Ser Ser Gln Ser Ile Ser Val Pro Gln
```

-continued

```
                 160                 165                 170
acc ttg aat caa gag ggg aag ctg ccg ttt tgc ggc ttc aac ttc aca         639
Thr Leu Asn Gln Glu Gly Lys Leu Pro Phe Cys Gly Phe Asn Phe Thr
            175                 180                 185 gag gag gaa ctg agc ttc gtt ctg tat gga gcc atc gct agt ccg gag         687
Glu Glu Glu Leu Ser Phe Val Leu Tyr Gly Ala Ile Ala Ser Pro Glu
        190                 195                 200 cac cca acc gac tta cag cat gca att tca ggc atc ctg gtt ccc aca         735
His Pro Thr Asp Leu Gln His Ala Ile Ser Gly Ile Leu Val Pro Thr
205                 210                 215                 220 gag agt tct ggg tct aat cat ctt cat aaa acc ctg gac aaa gac tcc         783
Glu Ser Ser Gly Ser Asn His Leu His Lys Thr Leu Asp Lys Asp Ser
                225                 230                 235 ctc cag ctt ccg gaa ggt ctc tgc ctc atg cag acc tca ttt ggt gat         831
Leu Gln Leu Pro Glu Gly Leu Cys Leu Met Gln Thr Ser Phe Gly Asp
            240                 245                 250 gtg cca cac ttt ggc gtg ttc tgc agc gac ttc att gcc aaa gga gtg         879
Val Pro His Phe Gly Val Phe Cys Ser Asp Phe Ile Ala Lys Gly Val
        255                 260                 265 aga ttt gga ccc ttt cga ggt aga gtg gtc aat gcc agc gaa gtg aag         927
Arg Phe Gly Pro Phe Arg Gly Arg Val Val Asn Ala Ser Glu Val Lys
    270                 275                 280 gca cac agg gac aac tct cgg atg tgg gaa att ttt gaa gat ggt cac         975
Ala His Arg Asp Asn Ser Arg Met Trp Glu Ile Phe Glu Asp Gly His
285                 290                 295                 300 ctg agc cat ttt atc gac ggc aaa ggt tct ggg aac tgg atg tcc tat        1023
Leu Ser His Phe Ile Asp Gly Lys Gly Ser Gly Asn Trp Met Ser Tyr
                305                 310                 315 gtc aac tgt gct cgg ttc ccc aag gag cag aac ctg ctg gcc gtg cag        1071
Val Asn Cys Ala Arg Phe Pro Lys Glu Gln Asn Leu Leu Ala Val Gln
            320                 325                 330 cac caa ggg cag ata ttt tat gag agt tgt aga gac atc cag cgg aac        1119
His Gln Gly Gln Ile Phe Tyr Glu Ser Cys Arg Asp Ile Gln Arg Asn
        335                 340                 345 cag gaa ctg ctt gtg tgg tac gga aat ggc tat gag aag ttc ctg ggc        1167
Gln Glu Leu Leu Val Trp Tyr Gly Asn Gly Tyr Glu Lys Phe Leu Gly
    350                 355                 360 gtt ccc atg aac ctc cgt gtc act gag caa gga ggc cag cag ctg tct        1215
Val Pro Met Asn Leu Arg Val Thr Glu Gln Gly Gly Gln Gln Leu Ser
365                 370                 375                 380 gag tcc tct gaa gag tct gca gaa ggt tac aga tgt gaa cgc tgt gga        1263
Glu Ser Ser Glu Glu Ser Ala Glu Gly Tyr Arg Cys Glu Arg Cys Gly
                385                 390                 395 aag gtg ttt acc tac aaa tac tac aga gat aag cac ctg aag tac acg        1311
Lys Val Phe Thr Tyr Lys Tyr Tyr Arg Asp Lys His Leu Lys Tyr Thr
            400                 405                 410 ccc tgt gtg gac aag ggg gac agg aag ttt ccg tgt tct ctc tgc caa        1359
Pro Cys Val Asp Lys Gly Asp Arg Lys Phe Pro Cys Ser Leu Cys Gln
        415                 420                 425 aga tcc ttt gaa aag cgc gac cgc ctc cgg atc cat att ctt cac gtc        1407
Arg Ser Phe Glu Lys Arg Asp Arg Leu Arg Ile His Ile Leu His Val
    430                 435                 440 cat gag agg cac cgg ccc tac ctg tgt tgt tca acc tgt ggg aaa agt        1455
His Glu Arg His Arg Pro Tyr Leu Cys Cys Ser Thr Cys Gly Lys Ser
445                 450                 455                 460 ttt tct cag tct tcc agc ctg aac aag cac atg aga gtc cac tct gga        1503
Phe Ser Gln Ser Ser Ser Leu Asn Lys His Met Arg Val His Ser Gly
                465                 470                 475 gac agg cca tac cag tgc gtg tac tgt aca aag aag ttc act gcc tcc        1551
Asp Arg Pro Tyr Gln Cys Val Tyr Cys Thr Lys Lys Phe Thr Ala Ser
```

```
            Asp Arg Pro Tyr Gln Cys Val Tyr Cys Thr Lys Lys Phe Thr Ala Ser
                        480                 485                 490 agc ata ctc cga aca cac atc aga cag cac tca gga gag aag ccc ttc         1599
Ser Ile Leu Arg Thr His Ile Arg Gln His Ser Gly Glu Lys Pro Phe
            495                 500                 505 aag tgc aag cat tgt ggt aaa gcc ttt gca tct cat gct gcc cac gac         1647
Lys Cys Lys His Cys Gly Lys Ala Phe Ala Ser His Ala Ala His Asp
510                 515                 520 agc cac gtc cgg cgc tca cac aag gac aat ggc cgt agc tcc tgc gat         1695
Ser His Val Arg Arg Ser His Lys Asp Asn Gly Arg Ser Ser Cys Asp
525                 530                 535                 540 att tgt ggg aaa ggc ttc ctg gat caa gag gct ttc tat gcc cac atg         1743
Ile Cys Gly Lys Gly Phe Leu Asp Gln Glu Ala Phe Tyr Ala His Met
                545                 550                 555 agg ctt cat aaa acc tgc tag gtctttgaaa gcaaagccag ttacaaacca            1794
Arg Leu His Lys Thr Cys
                560 agaacgctga ctctcattcc tgctttgtct gtgtcgcgtg ggcatggttg aagtgttcag       1854 tgagaatctg gagaatggag tagttgatct gaagctccaa accttatgga atccattcag       1914 accaggagtg agaataaagt cctgggtctt gtgattaaag aagaaaaggt tcccctctc        1974 ctgtctgcct tgaacacccc gttatacggt gtctgtagcc agcgactatg tgcatgagtg       2034 ttcgccgcgg gcatgtttct gtgctgcatg cgtgtggagg cccaaggaag acatcagatc       2094 ctctggggct gtatttacgg atagttgtaa gccactgtgt gggtaccggg aattgaaccc       2154 aggtcctctg ctagtgctgc taggacttaa ctgctaaacc atctcaccag ctcctgcttt       2214 ctatttggtt ttggtggtgg tgttttggtc tctctctctt tctctcccac ccccaagctg       2274 gctttaaatt tgtcctatag ctgaaaatga ccttgaatta caggattaag ttaccacagc       2334 caagcaattt gcactaccta gagatttggt atgttataac taagtcttct gccgtgtatt       2394 agtgttccat cttaatttga gctcatttct ctcctcactg agcaatgaaa atgccaggta       2454 atacacctag tatcagaaag aatcatttcc agggcaggaa gactggcaat tcttgttgat       2514 gtctaacttt taccaacaga gaaggaaaat tatatctgaa taaagacagg ctgaaaataa       2574 acacttatgc tactctggtt tt                                                2596
```

<210> SEQ ID NO 8
<211> LENGTH: 562
<212> TYPE: PRT
<213> ORGANISM: Mus musculus

<400> SEQUENCE: 8

```
Met Ala Leu Pro Pro Ser Gly Glu Thr Gln Ser Gln Asp Lys Ala Asn
1               5                   10                  15

Tyr Leu Pro Gln Ser Asn Pro His His Leu Thr Thr Tyr Ala His
                20                  25                  30

Ala Pro Gly Tyr Ser His Phe Arg Asn Leu Ala Thr Glu Glu Glu
            35                  40                  45

Phe Gln Pro Trp Lys Leu Ala Ala Val Leu Glu Ser Gln Ala Met
    50                  55                  60

Ala Pro Leu Asp Ala Phe Arg Met Thr Ala Pro Leu Leu Asn Pro Gly
65                  70                  75                  80

Leu Ala Val Gln Ser Glu Pro Leu Tyr Asn Leu Pro Trp Tyr Lys Leu
                85                  90                  95

Ser Pro Trp Asn Arg Ile Pro Gln Phe Thr Pro Glu Val Pro Arg Phe
                100                 105                 110
```

```
Leu Asp Ser Thr Glu His Arg Ser Gly Ser Ser Asn Gln Asn Leu
        115                 120                 125

Val Leu Gly Gly Gly Gly Gln Ile Ser Gly Gln Arg Trp Glu Ala
    130                 135                 140

Glu Asn Leu Leu Leu Pro Ser Pro Val Ile Ala Ser Leu Leu Pro Asp
145                 150                 155                 160

Gly Ile Lys Ser Ser Gln Ser Ile Ser Val Pro Gln Thr Leu Asn Gln
                165                 170                 175

Glu Gly Lys Leu Pro Phe Cys Gly Phe Asn Phe Thr Glu Glu Leu
            180                 185                 190

Ser Phe Val Leu Tyr Gly Ala Ile Ala Ser Pro Glu His Pro Thr Asp
        195                 200                 205

Leu Gln His Ala Ile Ser Gly Ile Leu Val Pro Thr Glu Ser Ser Gly
    210                 215                 220

Ser Asn His Leu His Lys Thr Leu Asp Lys Asp Ser Leu Gln Leu Pro
225                 230                 235                 240

Glu Gly Leu Cys Leu Met Gln Thr Ser Phe Gly Asp Val Pro His Phe
                245                 250                 255

Gly Val Phe Cys Ser Asp Phe Ile Ala Lys Gly Val Arg Phe Gly Pro
            260                 265                 270

Phe Arg Gly Arg Val Val Asn Ala Ser Glu Val Lys Ala His Arg Asp
        275                 280                 285

Asn Ser Arg Met Trp Glu Ile Phe Glu Asp Gly His Leu Ser His Phe
    290                 295                 300

Ile Asp Gly Lys Gly Ser Gly Asn Trp Met Ser Tyr Val Asn Cys Ala
305                 310                 315                 320

Arg Phe Pro Lys Glu Gln Asn Leu Leu Ala Val Gln His Gln Gly Gln
                325                 330                 335

Ile Phe Tyr Glu Ser Cys Arg Asp Ile Gln Arg Asn Gln Glu Leu Leu
            340                 345                 350

Val Trp Tyr Gly Asn Gly Tyr Glu Lys Phe Leu Gly Val Pro Met Asn
        355                 360                 365

Leu Arg Val Thr Glu Gln Gly Gly Gln Gln Leu Ser Glu Ser Ser Glu
    370                 375                 380

Glu Ser Ala Glu Gly Tyr Arg Cys Glu Arg Cys Gly Lys Val Phe Thr
385                 390                 395                 400

Tyr Lys Tyr Tyr Arg Asp Lys His Leu Lys Tyr Thr Pro Cys Val Asp
                405                 410                 415

Lys Gly Asp Arg Lys Phe Pro Cys Ser Leu Cys Gln Arg Ser Phe Glu
            420                 425                 430

Lys Arg Asp Arg Leu Arg Ile His Ile Leu His Val His Glu Arg His
        435                 440                 445

Arg Pro Tyr Leu Cys Cys Ser Thr Cys Gly Lys Ser Phe Ser Gln Ser
    450                 455                 460

Ser Ser Leu Asn Lys His Met Arg Val His Ser Gly Asp Arg Pro Tyr
465                 470                 475                 480

Gln Cys Val Tyr Cys Thr Lys Lys Phe Thr Ala Ser Ser Ile Leu Arg
                485                 490                 495

Thr His Ile Arg Gln His Ser Gly Glu Lys Pro Phe Lys Cys Lys His
            500                 505                 510

Cys Gly Lys Ala Phe Ala Ser His Ala Ala His Asp Ser His Val Arg
        515                 520                 525
```

```
Arg Ser His Lys Asp Asn Gly Arg Ser Ser Cys Asp Ile Cys Gly Lys
    530                 535                 540

Gly Phe Leu Asp Gln Glu Ala Phe Tyr Ala His Met Arg Leu His Lys
545                 550                 555                 560

Thr Cys

<210> SEQ ID NO 9
<211> LENGTH: 2895
<212> TYPE: DNA
<213> ORGANISM: Homo sapiens
<220> FEATURE:
<221> NAME/KEY: CDS
<222> LOCATION: (244)..(1596)

<400> SEQUENCE: 9
cgccaggaca cactgttcgg gcgcggcttt ccccgtccgc ggagcggtct tgacactcgc        60
ggcggcagca tctacgctcg cagagccgcc gatgcgtgtc cagtgacccg gacagcaagg       120
cccgcgcgcg gcggggcgg cggcagacgc ctggtcaccg tgaccccgat tttggattta       180
ccgcttgggg gctgggggga tcctggattt aactggcgac tgttttgggg gacgccggac       240 gcc atg ttg tgg aaa ata acc gat aat gtc aag tac gaa gag gac tgc        288
    Met Leu Trp Lys Ile Thr Asp Asn Val Lys Tyr Glu Glu Asp Cys
    1               5                  10                  15 gag gat cgc cac gac ggg agc agc aat ggg aat ccg cgg gtc ccc cac        336
Glu Asp Arg His Asp Gly Ser Ser Asn Gly Asn Pro Arg Val Pro His
            20                  25                  30 ctc tcc tcc gcc ggg cag cac ctc tac agc ccc gcg cca ccc ctc tcc        384
Leu Ser Ser Ala Gly Gln His Leu Tyr Ser Pro Ala Pro Pro Leu Ser
        35                  40                  45 cac act gga gtc gcc gaa tat cag ccg cca ccc tac ttt ccc cct ccc        432
His Thr Gly Val Ala Glu Tyr Gln Pro Pro Pro Tyr Phe Pro Pro Pro
    50                  55                  60 tac cag cag ctg gcc tac tcc cag tcg gcc gac ccc tac tcg cat ctg        480
Tyr Gln Gln Leu Ala Tyr Ser Gln Ser Ala Asp Pro Tyr Ser His Leu
65                  70                  75 ggg gaa gcg tac gcc gcc gcc atc aac ccc ctg cac cag ccg gcg ccc        528
Gly Glu Ala Tyr Ala Ala Ala Ile Asn Pro Leu His Gln Pro Ala Pro
80                  85                  90                  95 aca ggc agc cag cag cag gcc tgg ccc ggc cgc cag agc cag gag gga        576
Thr Gly Ser Gln Gln Gln Ala Trp Pro Gly Arg Gln Ser Gln Glu Gly
            100                 105                 110 gcg ggg ctg ccc tcg cac cac ggg cgc ccg gcc gga cta ctg ccc cac        624
Ala Gly Leu Pro Ser His His Gly Arg Pro Ala Gly Leu Leu Pro His
        115                 120                 125 ctc tcc ggg ctg gag gcg ggc gcg gtg agc gcc cgc agg gat gcc tac        672
Leu Ser Gly Leu Glu Ala Gly Ala Val Ser Ala Arg Arg Asp Ala Tyr
    130                 135                 140 cgc cgc tcc gac ctg ctg ctg ccc cac gca cac gcc ctg gat gcc gcg        720
Arg Arg Ser Asp Leu Leu Leu Pro His Ala His Ala Leu Asp Ala Ala
145                 150                 155 ggc ctg gcc gag aac ctg ggg ctc cac gac atg cct cac cag atg gac        768
Gly Leu Ala Glu Asn Leu Gly Leu His Asp Met Pro His Gln Met Asp
160                 165                 170                 175 gag gtg cag aat gtc gac gac cag cac ctg ttg ctg cac gat cag aca        816
Glu Val Gln Asn Val Asp Asp Gln His Leu Leu Leu His Asp Gln Thr
            180                 185                 190 gtc att cgc aaa ggt ccc att tcc atg acc aag aac cct ctg aac ctc        864
Val Ile Arg Lys Gly Pro Ile Ser Met Thr Lys Asn Pro Leu Asn Leu
        195                 200                 205
```

```
ccc tgt cag aag gag ctg gtg ggg gcc gta atg aac ccc act gag gtc    912
Pro Cys Gln Lys Glu Leu Val Gly Ala Val Met Asn Pro Thr Glu Val
        210                 215                 220 ttc tgc tca gtc cct gga aga ttg tcg ctc ctc agc tct acg tct aaa    960
Phe Cys Ser Val Pro Gly Arg Leu Ser Leu Leu Ser Ser Thr Ser Lys
225                 230                 235 tac aaa gtg aca gtg gct gaa gta cag agg cga ctg tcc cca cct gaa   1008
Tyr Lys Val Thr Val Ala Glu Val Gln Arg Arg Leu Ser Pro Pro Glu
240                 245                 250                 255 tgc tta aat gcc tcg tta ctg gga ggt gtt ctc aga aga gcc aaa tcg   1056
Cys Leu Asn Ala Ser Leu Leu Gly Gly Val Leu Arg Arg Ala Lys Ser
                260                 265                 270 aaa aat gga ggc cgg tcc ttg cgg gag aag ttg gac aag att ggg ttg   1104
Lys Asn Gly Gly Arg Ser Leu Arg Glu Lys Leu Asp Lys Ile Gly Leu
            275                 280                 285 aat ctt ccg gcc ggg agg cgg aaa gcc gct cat gtg act ctc ctg aca   1152
Asn Leu Pro Ala Gly Arg Arg Lys Ala Ala His Val Thr Leu Leu Thr
        290                 295                 300 tcc tta gta gaa ggt gaa gct gtt cat ttg gct agg gac ttt gcc tat   1200
Ser Leu Val Glu Gly Glu Ala Val His Leu Ala Arg Asp Phe Ala Tyr
305                 310                 315 gtc tgt gaa gcc gaa ttt cct agt aaa cca gtg gca gaa tat tta acc   1248
Val Cys Glu Ala Glu Phe Pro Ser Lys Pro Val Ala Glu Tyr Leu Thr
320                 325                 330                 335 aga cct cat ctt gga gga cga aat gag atg gca gct agg aag aac atg   1296
Arg Pro His Leu Gly Gly Arg Asn Glu Met Ala Ala Arg Lys Asn Met
                340                 345                 350 cta ttg gcg gcc cag caa ctg tgt aaa gaa ttc aca gaa ctt ctc agc   1344
Leu Leu Ala Ala Gln Gln Leu Cys Lys Glu Phe Thr Glu Leu Leu Ser
            355                 360                 365 caa gac cgg aca ccc cat ggg acc agc agg ctc gcc cca gtc ttg gag   1392
Gln Asp Arg Thr Pro His Gly Thr Ser Arg Leu Ala Pro Val Leu Glu
        370                 375                 380 acg aac ata cag aac tgc ttg tct cat ttc agc ctg att acc cac ggg   1440
Thr Asn Ile Gln Asn Cys Leu Ser His Phe Ser Leu Ile Thr His Gly
385                 390                 395 ttt ggc agc cag gcc atc tgt gcc gcg gtg tct gcc ctg cag aac tac   1488
Phe Gly Ser Gln Ala Ile Cys Ala Ala Val Ser Ala Leu Gln Asn Tyr
400                 405                 410                 415 atc aaa gaa gcc ctg att gtc ata gac aaa tcc tac atg aac cct gga   1536
Ile Lys Glu Ala Leu Ile Val Ile Asp Lys Ser Tyr Met Asn Pro Gly
                420                 425                 430 gac cag agt cca gct gat tct aac aaa acc ctg gag aaa atg gag aaa   1584
Asp Gln Ser Pro Ala Asp Ser Asn Lys Thr Leu Glu Lys Met Glu Lys
            435                 440                 445 cac agg aaa taa aattggaacg aagaaaggtt aggagagtag ggaaggaaca       1636
His Arg Lys
        450 ggactgcaaa atccttctc caccgcacag actgggaacc cctcctggcc tggggaaga   1696 gtttgttacc tacctacta tttaaagagc cttcactggt tctgcatcac ccgcccctgg  1756 acttcttagt tgtttctcta gcgctgagct atctcctaac tttggaccta ttatcagaag 1816 gtgacaagta ctggctcttt attcattaag cttttttttt ttgaacccca ttctttcctt 1876 ctctgaaagt ggtgctataa gttttagaat cttttaaata cattccctgg gccaacagac 1936 ccacacactt agccattgaa atgtcaaatt gatgtgccct agatcaacag atcaacaata 1996 ccttttttt cagtgttaag gtaatggttg gttttgtgt ccgctaaata tttaccttga    2056 aaaaagaaa agtgtgtatc tagcttcttc agagatcaag tcctctggta ggaggcaaag   2116
```

```
gttctatctg cttagcaact agttaataag tggtatctga cacactctaa accccgtgtt    2176
caaacggggg ccttctggtt ttaggaaact tgtagaaacg aagcctgctg attgattttt    2236
ttctcctttt tttttttttt tttttttaac tttgaaagtt aactcttcaa atgggagact    2296
ctttgaaatg acatgttcct ttaaggtact gaagctttat ttgcatattt atttcagatg    2356
tttcgagtaa acttgaaaag ggtaggcacg aagcaatttg ttgctgcttg tcaccccaa     2416 gtccccgtgg aggttctgta ttttaagaaa cagtgcgttg agtgtacaga ttttatttat    2476
gcgtaattta atgggtctg  taaatactgg tgcacttctt acgactttt  tgagacatgg    2536 gatccaattt taatattaac ttttaatggt gatggggtaa tctataacac atcataaggt    2596
tttattcata tatacagg   gtattaagaa ttaagaggat gctgggctct gttcttggct    2656
tggaagattc tatttaattg aaactctctg ttcagaaagc aataactttg tctcgttcct    2716
gttgggctga accctaaggt gagtgtgcag tacagtgtgt gtgggtgaaa tggagatttg    2776
gaattgaact ctctgcctgt aaatgttccc caaataattg ttgtgtgtat gatacgtgta    2836
taataaaagt attcttgtta gaatctgaaa aaaaaaaaa  aaaaaaaaa  aaaaaaaa     2895
```

<210> SEQ ID NO 10
<211> LENGTH: 450
<212> TYPE: PRT
<213> ORGANISM: Homo sapiens

<400> SEQUENCE: 10

```
Met Leu Trp Lys Ile Thr Asp Asn Val Lys Tyr Glu Glu Asp Cys Glu
1               5                   10                  15

Asp Arg His Asp Gly Ser Ser Asn Gly Asn Pro Arg Val Pro His Leu
            20                  25                  30

Ser Ser Ala Gly Gln His Leu Tyr Ser Pro Ala Pro Pro Leu Ser His
        35                  40                  45

Thr Gly Val Ala Glu Tyr Gln Pro Pro Pro Tyr Phe Pro Pro Pro Tyr
    50                  55                  60

Gln Gln Leu Ala Tyr Ser Gln Ser Ala Asp Pro Tyr Ser His Leu Gly
65                  70                  75                  80

Glu Ala Tyr Ala Ala Ala Ile Asn Pro Leu His Gln Pro Ala Pro Thr
                85                  90                  95

Gly Ser Gln Gln Gln Ala Trp Pro Gly Arg Gln Ser Gln Glu Gly Ala
            100                 105                 110

Gly Leu Pro Ser His His Gly Arg Pro Ala Gly Leu Leu Pro His Leu
        115                 120                 125

Ser Gly Leu Glu Ala Gly Ala Val Ser Ala Arg Arg Asp Ala Tyr Arg
    130                 135                 140

Arg Ser Asp Leu Leu Leu Pro His Ala His Ala Leu Asp Ala Ala Gly
145                 150                 155                 160

Leu Ala Glu Asn Leu Gly Leu His Asp Met Pro His Gln Met Asp Glu
                165                 170                 175

Val Gln Asn Val Asp Asp Gln His Leu Leu His Asp Gln Thr Val
            180                 185                 190

Ile Arg Lys Gly Pro Ile Ser Met Thr Lys Asn Pro Leu Asn Leu Pro
        195                 200                 205

Cys Gln Lys Glu Leu Val Gly Ala Val Met Asn Pro Thr Glu Val Phe
    210                 215                 220

Cys Ser Val Pro Gly Arg Leu Ser Leu Leu Ser Ser Thr Ser Lys Tyr
225                 230                 235                 240
```

```
Lys Val Thr Val Ala Glu Val Gln Arg Arg Leu Ser Pro Pro Glu Cys
            245                 250                 255

Leu Asn Ala Ser Leu Leu Gly Gly Val Leu Arg Arg Ala Lys Ser Lys
        260                 265                 270

Asn Gly Gly Arg Ser Leu Arg Glu Lys Leu Asp Lys Ile Gly Leu Asn
    275                 280                 285

Leu Pro Ala Gly Arg Arg Lys Ala Ala His Val Thr Leu Leu Thr Ser
290                 295                 300

Leu Val Glu Gly Glu Ala Val His Leu Ala Arg Asp Phe Ala Tyr Val
305                 310                 315                 320

Cys Glu Ala Glu Phe Pro Ser Lys Pro Val Ala Glu Tyr Leu Thr Arg
                325                 330                 335

Pro His Leu Gly Gly Arg Asn Glu Met Ala Ala Arg Lys Asn Met Leu
            340                 345                 350

Leu Ala Ala Gln Gln Leu Cys Lys Glu Phe Thr Glu Leu Leu Ser Gln
        355                 360                 365

Asp Arg Thr Pro His Gly Thr Ser Arg Leu Ala Pro Val Leu Glu Thr
    370                 375                 380

Asn Ile Gln Asn Cys Leu Ser His Phe Ser Leu Ile Thr His Gly Phe
385                 390                 395                 400

Gly Ser Gln Ala Ile Cys Ala Ala Val Ser Ala Leu Gln Asn Tyr Ile
                405                 410                 415

Lys Glu Ala Leu Ile Val Ile Asp Lys Ser Tyr Met Asn Pro Gly Asp
            420                 425                 430

Gln Ser Pro Ala Asp Ser Asn Lys Thr Leu Glu Lys Met Glu Lys His
        435                 440                 445

Arg Lys
    450

<210> SEQ ID NO 11
<211> LENGTH: 2804
<212> TYPE: DNA
<213> ORGANISM: Mus musculus
<220> FEATURE:
<221> NAME/KEY: CDS
<222> LOCATION: (222)..(1571)

<400> SEQUENCE: 11
gcttctccgg tccacggctg cggcctctac acacccacgg cgaccacatc tctgtgcaca    60
gccaccgatg cgcgtccagt gactgggaca gcaaggccgg cgcgcgcggc ggggcggcg   120 gcagacgcct ggccaccgtg accccgattg tggatttacc gctcgggggg tggggggagc   180
ctggatttaa ctggcgacta ttttggggga cgccggacgc c atg ttg tgg aaa ata   236
                                             Met Leu Trp Lys Ile
                                               1               5 aca gat aat gtc aag tat gaa gag gat tgc gag gat cgc cac gac tcg   284
Thr Asp Asn Val Lys Tyr Glu Glu Asp Cys Glu Asp Arg His Asp Ser
             10                  15                  20 agc agt aat ggc aac cct cgc atc cct cac ctc tcc tct ccg gga caa   332
Ser Ser Asn Gly Asn Pro Arg Ile Pro His Leu Ser Ser Pro Gly Gln
         25                  30                  35 cat ctc tac agt ccc gcg ccg cct ctc tcg cac acc ggg gtt gca gag   380
His Leu Tyr Ser Pro Ala Pro Pro Leu Ser His Thr Gly Val Ala Glu
     40                  45                  50 tac cag ccg cct cct tac ttc ccg ccg cct tac cag cag gtg gta tac   428
Tyr Gln Pro Pro Pro Tyr Phe Pro Pro Pro Tyr Gln Gln Val Val Tyr
 55                  60                  65
```

-continued

| | |
|---|---|
| tcg cag tcc gcc gac cat tac tcg cat ctg gga gag gct tac gct gcc<br>Ser Gln Ser Ala Asp His Tyr Ser His Leu Gly Glu Ala Tyr Ala Ala<br>70                        75                        80                      85 | 476 |
| gcc atg aac ccc ctg cac cag cct gcg gcc acc ggc agc cag caa cag<br>Ala Met Asn Pro Leu His Gln Pro Ala Ala Thr Gly Ser Gln Gln Gln<br>                    90                        95                        100 | 524 |
| gcc tgg ccg ggt cga cag agt cag gag ggc tct agc ctg gcc tcg cac<br>Ala Trp Pro Gly Arg Gln Ser Gln Glu Gly Ser Ser Leu Ala Ser His<br>                    105                      110                      115 | 572 |
| cac agc cgc tct gca agt cta ata ccc cat att tca ggg ctg gag ggg<br>His Ser Arg Ser Ala Ser Leu Ile Pro His Ile Ser Gly Leu Glu Gly<br>        120                      125                      130 | 620 |
| ggc tcg gtg agc gcc cgg cgg gaa gtc tac cgc cgg tcc gac ctg ctg<br>Gly Ser Val Ser Ala Arg Arg Glu Val Tyr Arg Arg Ser Asp Leu Leu<br>135                        140                      145 | 668 |
| ctg cct cac gcg cac gcc ctg gaa gcc ggc ctg gct gag aac ctg ggg<br>Leu Pro His Ala His Ala Leu Glu Ala Gly Leu Ala Glu Asn Leu Gly<br>150                        155                      160                      165 | 716 |
| ctg cac gag atg gct cac ccc ata gag gag gtg cag aat gtg gac gac<br>Leu His Glu Met Ala His Pro Ile Glu Glu Val Gln Asn Val Asp Asp<br>                    170                      175                      180 | 764 |
| gcg cac ttg ctc cta cac gat cag act gtc att cgc aaa gga ccc att<br>Ala His Leu Leu Leu His Asp Gln Thr Val Ile Arg Lys Gly Pro Ile<br>                  185                      190                      195 | 812 |
| tcg atg acc aag aac cct ttg ggg ctc cct tgc cag aag gac ctg gtg<br>Ser Met Thr Lys Asn Pro Leu Gly Leu Pro Cys Gln Lys Asp Leu Val<br>        200                      205                      210 | 860 |
| gga gtg gtc atg aac ccc agt gag gtc ttc tgc tcg gtc cct gga aga<br>Gly Val Val Met Asn Pro Ser Glu Val Phe Cys Ser Val Pro Gly Arg<br>215                        220                      225 | 908 |
| ctg tcc ctg ctc agc tcc acg tcg aag tac aaa gta act gtg gct gag<br>Leu Ser Leu Leu Ser Ser Thr Ser Lys Tyr Lys Val Thr Val Ala Glu<br>230                        235                      240                      245 | 956 |
| gta cag agg cga ctg tca cca ccg gaa tgc cta aac gcc tcg ctc ctg<br>Val Gln Arg Arg Leu Ser Pro Pro Glu Cys Leu Asn Ala Ser Leu Leu<br>                  250                      255                      260 | 1004 |
| gga ggt gtg ctc aga aga gca aag tcc aaa aat gga ggc cgg tcc ttg<br>Gly Gly Val Leu Arg Arg Ala Lys Ser Lys Asn Gly Gly Arg Ser Leu<br>                  265                      270                      275 | 1052 |
| agg gag aag ttg gac aaa att gga ttg aac ctt ccg gcc ggg aga cgg<br>Arg Glu Lys Leu Asp Lys Ile Gly Leu Asn Leu Pro Ala Gly Arg Arg<br>        280                      285                      290 | 1100 |
| aaa gct gcc cac gtc act ctc ctc acg tct ctc gtg gaa ggt gaa gcc<br>Lys Ala Ala His Val Thr Leu Leu Thr Ser Leu Val Glu Gly Glu Ala<br>295                        300                      305 | 1148 |
| gtc cac cta gca cgg gac ttc gcc tat gtc tgc gaa gct gag ttc cct<br>Val His Leu Ala Arg Asp Phe Ala Tyr Val Cys Glu Ala Glu Phe Pro<br>310                        315                      320                      325 | 1196 |
| agt aaa gcg gtg gct gac tat tta acg aga cca cat ctt ggg gga cgg<br>Ser Lys Ala Val Ala Asp Tyr Leu Thr Arg Pro His Leu Gly Gly Arg<br>                  330                      335                      340 | 1244 |
| aat gag atg gcc acg cgg aag agt atg ttg ttg gct gca cag cag gtg<br>Asn Glu Met Ala Thr Arg Lys Ser Met Leu Leu Ala Ala Gln Gln Val<br>                    345                      350                      355 | 1292 |
| tgc aag gag ttc act gac ctt ctc cat caa gat cgg aca ccc aac ggg<br>Cys Lys Glu Phe Thr Asp Leu Leu His Gln Asp Arg Thr Pro Asn Gly<br>        360                      365                      370 | 1340 |
| aac aac agg ccc gcc cag gtc ttg gag ccg aac ata caa aac tgt ttg<br>Asn Asn Arg Pro Ala Gln Val Leu Glu Pro Asn Ile Gln Asn Cys Leu | 1388 |

```
                375                 380                 385
tct cat ttc agc ctg ata act cat ggc ttt ggc agc cag gcc atc tgt      1436
Ser His Phe Ser Leu Ile Thr His Gly Phe Gly Ser Gln Ala Ile Cys
390                 395                 400                 405 gcg gcg gtc tcc gca gtg cag aat tat atc aag gag gct cta atc gcc      1484
Ala Ala Val Ser Ala Val Gln Asn Tyr Ile Lys Glu Ala Leu Ile Ala
                410                 415                 420 atc gat aag tcc tac atg aac ccg ggg gac cag agt ccg gct gat tcc      1532
Ile Asp Lys Ser Tyr Met Asn Pro Gly Asp Gln Ser Pro Ala Asp Ser
            425                 430                 435 agc aag acg atg gag aaa atg gaa aag cac agg aag taa aatggctgca       1581
Ser Lys Thr Met Glu Lys Met Glu Lys His Arg Lys
        440                 445 aggaggccag agagcagaag gagaggaccc aggcccctcc actggggcag cccgggaagt    1641
gtccagagca gcagcagcag cagggaagca gttacaaccc gcccgcccac accgcactct    1701
ggacctgccc tcttggagtc tttgtgactt ttccatttaa ccctggacat gctatcctga    1761
agccacttgg tttggttctt ttattcatta aacatgtgtg ttttttgttt ttttttaaa     1821
tccgttccct ctcttgaaag gtgctacgag ttttagaacc ctttgtaaga actccctggg    1881
cagacaagaa actccacgct tagctgctaa cacagcaggt gcatgggagt cgtcagataa    1941
agggatcgat caatcataac ttatttcttt ttcagtgtta agataatagc tggcttttat    2001
gtccactaaa atatttatct aaaaaaaaat agtatttatc tagttttccc caccaccttg    2061
tcaatcacac cttctggtag gaggcagaag tcagagatgc tcttagcagg cagctactta    2121
ccagtggtat gtgacaggct tccagctact cattcaaaaa aggggtcccc tgttttaag    2181
gaacttgaaa gcaaagcctg ctgtttcttt cctgtttcct tcctctttta aaaaaatatt    2241
gaaagtttaa aattctttag ataataggat ttttaaatga tctgttcctt taaggtagag    2301
aagtttatt tgcatattta tttcagatct tgattttttt ttttccacaa aacttgaaga    2361
gggtaggcac acagcggcgc ctgccatccc taagtccccg aggaggctcc gtgctgagaa    2421
actgttgagt gtacagattt tatttatgca taatttaatg ggatctgtaa atacttctta    2481
tgactttttg agaaatggga ttcgatttta aaattacctt ttaatggtgg tgggtcatgt    2541
agcccctcta gcttttatgc gagtgcacac agggtattga aactgaagat gaagctgggc    2601
ttttctctct tggctggtca agtattattt gattggagct gtttaggaag caataggcat    2661
ctcatttctg cgggctgaac cggaagagaa tggagtttag tttgtgtggg tgacgtgtgg    2721
attgggactg gacctctaag cctgtccgtg ctccttaaat aattgttgtg tgtgatacct    2781
gtataataaa aaatattctc gat                                            2804
```

<210> SEQ ID NO 12
<211> LENGTH: 449
<212> TYPE: PRT
<213> ORGANISM: Mus musculus

<400> SEQUENCE: 12

```
Met Leu Trp Lys Ile Thr Asp Asn Val Lys Tyr Glu Glu Asp Cys Glu
1               5                   10                  15

Asp Arg His Asp Ser Ser Ser Asn Gly Asn Pro Arg Ile Pro His Leu
            20                  25                  30

Ser Ser Pro Gly Gln His Leu Tyr Ser Pro Ala Pro Leu Ser His
        35                  40                  45

Thr Gly Val Ala Glu Tyr Gln Pro Pro Tyr Phe Pro Pro Pro Tyr
    50                  55                  60
```

Gln Gln Val Val Tyr Ser Gln Ser Ala Asp His Tyr Ser His Leu Gly
65                  70                  75                  80

Glu Ala Tyr Ala Ala Ala Met Asn Pro Leu His Gln Pro Ala Ala Thr
                85                  90                  95

Gly Ser Gln Gln Gln Ala Trp Pro Gly Arg Gln Ser Gln Glu Gly Ser
            100                 105                 110

Ser Leu Ala Ser His His Ser Arg Ser Ala Ser Leu Ile Pro His Ile
        115                 120                 125

Ser Gly Leu Glu Gly Gly Ser Val Ser Ala Arg Arg Glu Val Tyr Arg
    130                 135                 140

Arg Ser Asp Leu Leu Pro His Ala His Ala Leu Glu Ala Gly Leu
145                 150                 155                 160

Ala Glu Asn Leu Gly Leu His Glu Met Ala His Pro Ile Glu Glu Val
                165                 170                 175

Gln Asn Val Asp Asp Ala His Leu Leu Leu His Asp Gln Thr Val Ile
            180                 185                 190

Arg Lys Gly Pro Ile Ser Met Thr Lys Asn Pro Leu Gly Leu Pro Cys
        195                 200                 205

Gln Lys Asp Leu Val Gly Val Val Met Asn Pro Ser Glu Val Phe Cys
210                 215                 220

Ser Val Pro Gly Arg Leu Ser Leu Leu Ser Ser Thr Ser Lys Tyr Lys
225                 230                 235                 240

Val Thr Val Ala Glu Val Gln Arg Arg Leu Ser Pro Pro Glu Cys Leu
                245                 250                 255

Asn Ala Ser Leu Leu Gly Gly Val Leu Arg Arg Ala Lys Ser Lys Asn
            260                 265                 270

Gly Gly Arg Ser Leu Arg Glu Lys Leu Asp Lys Ile Gly Leu Asn Leu
        275                 280                 285

Pro Ala Gly Arg Arg Lys Ala Ala His Val Thr Leu Leu Thr Ser Leu
    290                 295                 300

Val Glu Gly Glu Ala Val His Leu Ala Arg Asp Phe Ala Tyr Val Cys
305                 310                 315                 320

Glu Ala Glu Phe Pro Ser Lys Ala Val Ala Asp Tyr Leu Thr Arg Pro
                325                 330                 335

His Leu Gly Gly Arg Asn Glu Met Ala Thr Arg Lys Ser Met Leu Leu
            340                 345                 350

Ala Ala Gln Gln Val Cys Lys Glu Phe Thr Asp Leu Leu His Gln Asp
        355                 360                 365

Arg Thr Pro Asn Gly Asn Asn Arg Pro Ala Gln Val Leu Glu Pro Asn
    370                 375                 380

Ile Gln Asn Cys Leu Ser His Phe Ser Leu Ile Thr His Gly Phe Gly
385                 390                 395                 400

Ser Gln Ala Ile Cys Ala Ala Val Ser Ala Val Gln Asn Tyr Ile Lys
                405                 410                 415

Glu Ala Leu Ile Ala Ile Asp Lys Ser Tyr Met Asn Pro Gly Asp Gln
            420                 425                 430

Ser Pro Ala Asp Ser Ser Lys Thr Met Glu Lys Met Glu Lys His Arg
        435                 440                 445

Lys

<210> SEQ ID NO 13
<211> LENGTH: 72
<212> TYPE: DNA

```
<213> ORGANISM: Artificial Sequence
<220> FEATURE:
<223> OTHER INFORMATION: Synthetic PCR Primer

<400> SEQUENCE: 13
gtcgacgcca ccatgtccgg cctgaacgac atcttcggcg ctcagaaaat cgaatggcac      60
gaactcgaga tg                                                         72

<210> SEQ ID NO 14
<211> LENGTH: 144
<212> TYPE: DNA
<213> ORGANISM: Artificial Sequence
<220> FEATURE:
<223> OTHER INFORMATION: Synthetic PCR Primer

<400> SEQUENCE: 14
ggtaccgcca ccatggacta caaggaccac gacggagatt ataaggatca cgatatcgac      60
tataaggatg acgacgataa gctcgagtct ggtggcggtg gctcgggcgg aggtgggtcg     120
ggtggcggcg gatcaactag tatg                                           144

<210> SEQ ID NO 15
<211> LENGTH: 117
<212> TYPE: DNA
<213> ORGANISM: Artificial Sequence
<220> FEATURE:
<223> OTHER INFORMATION: Synthetic PCR Primer

<400> SEQUENCE: 15
ggatccgcca ccatgggcaa gcccatccct aaccctctgc tgggcctgga cagcacctct      60
ggtggcggtg gctcgggcgg aggtgggtcg ggtggcggcg gatcaagcgg ccgcatg        117

<210> SEQ ID NO 16
<211> LENGTH: 87
<212> TYPE: DNA
<213> ORGANISM: Artificial Sequence
<220> FEATURE:
<223> OTHER INFORMATION: Synthetic PCR Primer

<400> SEQUENCE: 16
gcggtcgacg ccaccatgtc cggcctgaac gacatcttcg gcgctcagaa aatcgaatgg      60
cacgaactcg agatgaaaat ggacatg                                         87

<210> SEQ ID NO 17
<211> LENGTH: 35
<212> TYPE: DNA
<213> ORGANISM: Artificial Sequence
<220> FEATURE:
<223> OTHER INFORMATION: Synthetic PCR Primer

<400> SEQUENCE: 17
gcggcggccg cctaaggatc catcggttca actgt                                 35

<210> SEQ ID NO 18
<211> LENGTH: 28
<212> TYPE: DNA
<213> ORGANISM: Artificial Sequence
<220> FEATURE:
<223> OTHER INFORMATION: Synthetic PCR Primer

<400> SEQUENCE: 18
aaagcggccg catgttgtgg aaaataac                                         28
```

```
<210> SEQ ID NO 19
<211> LENGTH: 26
<212> TYPE: DNA
<213> ORGANISM: Artificial Sequence
<220> FEATURE:
<223> OTHER INFORMATION: Synthetic PCR Primer

<400> SEQUENCE: 19
atagaattct tacttcctgt gcttttt                                              26

<210> SEQ ID NO 20
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 20
tggtgcctgt aaaggtcaaa c                                                    21

<210> SEQ ID NO 21
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 21
ggcggaatta gcttatcgac                                                      20

<210> SEQ ID NO 22
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 22
tcctggatca agaggctttc                                                      20

<210> SEQ ID NO 23
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 23
actagctaga gcggccatca c                                                    21

<210> SEQ ID NO 24
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 24
attccagcaa gacgatggag                                                      20

<210> SEQ ID NO 25
<211> LENGTH: 20
<212> TYPE: DNA
<213> ORGANISM: Artificial Sequence
<220> FEATURE:
<223> OTHER INFORMATION: Synthetic PCR Primer
```

```
<400> SEQUENCE: 25
ggcggaatta gcttatcgac                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 26
gcttgccgaa tatcatggtg                                              20

<210> SEQ ID NO 27
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 27
cttcagcaat atcacgggta gc                                           22

<210> SEQ ID NO 28
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 28
gcccacctgc agaaacacta c                                            21

<210> SEQ ID NO 29
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 29
ccagaatgca atcgaaggtg                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 30
cttccagcct gaacaagcac                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 31
ggagtatgct ggaggcagtg                                              20

<210> SEQ ID NO 32
<211> LENGTH: 20
```

<212> TYPE: DNA
<213> ORGANISM: Artificial Sequence
<220> FEATURE:
<223> OTHER INFORMATION: Synthetic PCR Primer

<400> SEQUENCE: 32
ccacgcggaa gagtatgttg					20

<210> SEQ ID NO 33
<211> LENGTH: 19
<212> TYPE: DNA
<213> ORGANISM: Artificial Sequence
<220> FEATURE:
<223> OTHER INFORMATION: Synthetic PCR Primer

<400> SEQUENCE: 33
gttgttcccg ttgggtgtc					19

<210> SEQ ID NO 34
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 34
aaatcgaatg gcacgaactc					20

<210> SEQ ID NO 35
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 35
gcatccagtt gcttttctcc					20

<210> SEQ ID NO 36
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 36
atcgactata aggatgacga c					21

<210> SEQ ID NO 37
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 37
gaggttccta aagtgactgt ag				22

<210> SEQ ID NO 38
<211> LENGTH: 24
<212> TYPE: DNA
<213> ORGANISM: Artificial Sequence
<220> FEATURE:
<223> OTHER INFORMATION: Synthetic PCR Primer

<400> SEQUENCE: 38

```
atgggcaagc ccatccctaa ccct                                              24

<210> SEQ ID NO 39
<211> LENGTH: 25
<212> TYPE: DNA
<213> ORGANISM: Artificial Sequence
<220> FEATURE:
<223> OTHER INFORMATION: Synthetic PCR Primer

<400> SEQUENCE: 39
aaggaggcgg ctggtactct gcaac                                             25

<210> SEQ ID NO 40
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 40
actcatctca gaagaggatc tg                                                22

<210> SEQ ID NO 41
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 41
cacagtcgag gctgatctcg                                                   20

<210> SEQ ID NO 42
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 42
cgagctagct tttgaggctt                                                   20

<210> SEQ ID NO 43
<211> LENGTH: 20
<212> TYPE: DNA
<213> ORGANISM: Synthetic Artificial Sequence
<220> FEATURE:
<223> OTHER INFORMATION: Synthetic PCR Primer

<400> SEQUENCE: 43
aacttgtggc cgtttacgtc                                                   20

<210> SEQ ID NO 44
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 44
aaagtcgctc tgagttgtta t                                                 21

<210> SEQ ID NO 45
<211> LENGTH: 21
<212> TYPE: DNA
<213> ORGANISM: Artificial Sequence
```

```
<220> FEATURE:
<223> OTHER INFORMATION: Synthetic PCR Primer

<400> SEQUENCE: 45
ggagcgggag aaatggatat g                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 46
gcgaagagtt tgtcctcaac c                                              21

<210> SEQ ID NO 47
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 47
agcatgacct gacattgaca cc                                             22

<210> SEQ ID NO 48
<211> LENGTH: 23
<212> TYPE: DNA
<213> ORGANISM: Artificial Sequence
<220> FEATURE:
<223> OTHER INFORMATION: Synthetic PCR Primer

<400> SEQUENCE: 48
ctcaacactc tcatgtaaga ggc                                            23

<210> SEQ ID NO 49
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 49
acagccaagc aatttgcact ac                                             22

<210> SEQ ID NO 50
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 50
ttacctggca ttttcattgc tc                                             22

<210> SEQ ID NO 51
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 51
gggcttttct ctcttggctg gt                                             22
```

```
<210> SEQ ID NO 52
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 52
tccacacgtc acccacacaa                                                   20

<210> SEQ ID NO 53
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 53
cactacggcc taggagcttg g                                                 21

<210> SEQ ID NO 54
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 54
tgatcgctga caagactgtg gc                                                22

<210> SEQ ID NO 55
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 55
aggctcgaag gaaatgagtt tg                                                22

<210> SEQ ID NO 56
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 56
tcctaattct tcccgatttt cg                                                22

<210> SEQ ID NO 57
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 57
gatgctgtga gccaaggcaa g                                                 21

<210> SEQ ID NO 58
<211> LENGTH: 22
<212> TYPE: DNA
<213> ORGANISM: Artificial Sequence
<220> FEATURE:
<223> OTHER INFORMATION: Synthetic PCR Primer
```

<400> SEQUENCE: 58
ggctcctgat caacagcatc ac                                          22

<210> SEQ ID NO 59
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 59
catgagagca agtactggca ag                                          22

<210> SEQ ID NO 60
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 60
ccaacgatat caacctgcat gg                                          22

<210> SEQ ID NO 61
<211> LENGTH: 23
<212> TYPE: DNA
<213> ORGANISM: Artificial Sequence
<220> FEATURE:
<223> OTHER INFORMATION: Synthetic PCR Primer

<400> SEQUENCE: 61
ctttcaccta ttaaggtgct tgc                                         23

<210> SEQ ID NO 62
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 62
tggcatcggt tcatcatggt ac                                          22

<210> SEQ ID NO 63
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 63
gactcgcgtg caataacctt ag                                          22

<210> SEQ ID NO 64
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 64
ggtcactttc cctcactctg g                                           21

<210> SEQ ID NO 65

```
<211> LENGTH: 25
<212> TYPE: DNA
<213> ORGANISM: Artificial Sequence
<220> FEATURE:
<223> OTHER INFORMATION: Synthetic PCR Primer

<400> SEQUENCE: 65
ctcgcaaggt gtgggctttt gtaac                                         25

<210> SEQ ID NO 66
<211> LENGTH: 24
<212> TYPE: DNA
<213> ORGANISM: Artificial Sequence
<220> FEATURE:
<223> OTHER INFORMATION: Synthetic PCR Primer

<400> SEQUENCE: 66
ctgggcatct gtcatctttg cacc                                          24

<210> SEQ ID NO 67
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 67
gtgactagtc ttctgcatgt cg                                            22

<210> SEQ ID NO 68
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 68
tctgctctgg accacatcac tc                                            22

<210> SEQ ID NO 69
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 69
gatcctacag gtcttgggac c                                             21

<210> SEQ ID NO 70
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 70
agctcaaagg cactgaactg ag                                            22

<210> SEQ ID NO 71
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 71
```
atcagagtcc tttgctaggt ag                                              22

<210> SEQ ID NO 72
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 72
gttacaatct tctggctatg c                                               21

<210> SEQ ID NO 73
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 73
cacagtcccc gttcttttac tg                                              22

<210> SEQ ID NO 74
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 74
gtggtacagg cgtcaagagt g                                               21

<210> SEQ ID NO 75
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 75
caaagctgaa gcaaaggaag ag                                              22

<210> SEQ ID NO 76
<211> LENGTH: 23
<212> TYPE: DNA
<213> ORGANISM: Artificial Sequence
<220> FEATURE:
<223> OTHER INFORMATION: Synthetic PCR Primer

<400> SEQUENCE: 76
aattaagcag gctgacttgg ttg                                             23

<210> SEQ ID NO 77
<211> LENGTH: 24
<212> TYPE: DNA
<213> ORGANISM: Artificial Sequence
<220> FEATURE:
<223> OTHER INFORMATION: Synthetic PCR Primer

<400> SEQUENCE: 77
ttacccatca aaccattcct tctg                                            24

<210> SEQ ID NO 78
<211> LENGTH: 24
<212> TYPE: DNA

```
<213> ORGANISM: Artificial Sequence
<220> FEATURE:
<223> OTHER INFORMATION: Synthetic PCR Primer

<400> SEQUENCE: 78
aacccaaaga acttcagtga gagc                                              24
```